US011965195B2

(12) United States Patent
Eichhorn et al.

(10) Patent No.: US 11,965,195 B2
(45) Date of Patent: Apr. 23, 2024

(54) ENZYME MEDIATED PROCESS

(71) Applicant: Givaudan SA, Vernier (CH)

(72) Inventors: Eric Eichhorn, Zürich (CH); Felix Flachsmann, Duebendorf (CH)

(73) Assignee: GIVAUDAN SA, Vernier (CH)

( * ) Notice: Subject to any disclaimer, the term of this patent is extended or adjusted under 35 U.S.C. 154(b) by 59 days.

(21) Appl. No.: 17/777,336

(22) PCT Filed: Dec. 3, 2020

(86) PCT No.: PCT/EP2020/084508

§ 371 (c)(1),
(2) Date: May 17, 2022

(87) PCT Pub. No.: WO2021/110858

PCT Pub. Date: Jun. 10, 2021

(65) Prior Publication Data

US 2023/0009254 A1 Jan. 12, 2023

(30) Foreign Application Priority Data

Dec. 4, 2019 (GB) .................................... 1917694

(51) Int. Cl.
*C12P 17/04* (2006.01)
*C07C 33/02* (2006.01)
*C07D 307/92* (2006.01)

(52) U.S. Cl.
CPC .............. *C12P 17/04* (2013.01); *C07C 33/02* (2013.01); *C07D 307/92* (2013.01); *C12Y 504/99017* (2013.01)

(58) Field of Classification Search
None
See application file for complete search history.

(56) References Cited

U.S. PATENT DOCUMENTS

2009/0131300 A1 5/2009 Boden et al.

FOREIGN PATENT DOCUMENTS

| | | | | |
|---|---|---|---|---|
| EP | 2060567 A1 | 5/2009 | | |
| WO | 2013156398 A1 | 10/2013 | | |
| WO | 2016170099 A1 | 10/2016 | | |
| WO | 2017182542 A1 | 10/2017 | | |
| WO | WO-2018157021 A1 * | 8/2018 | ............... | C12N 9/90 |

OTHER PUBLICATIONS

International Search Report for App. No. PCT/EP2020/084508 dated Mar. 16, 2021.
Written Opinion for App. No. PCT/EP2020/084508 dated Mar. 16, 2021.
Great Britain Search Report for App. No. 1917694.0 dated Jun. 5, 2020.
Eric Eichhorn, et al., Biocatalylic Process for (−)-Ambrox Production Using Squalene Hopene Cyclase, Advanced Synthesis & Catalysis, May 2, 2018, pp. 2339-2351, vol. 360, Wiley-VCH Verlag GmbH & Co.
Miriam Seitz, Characterization of the substrate specificity of squalene-hopene cyclases (SHCs), PhD Dissertation, Feb. 6, 2013.
I. B. Bersuker, et al., Structural and Electronic Origin of Ambergris Odor of Cyclic Compounds, Nouveau Journal de Chimie, Mar. 1985, pp. 211-218, vol. 9, CNRS—Gauthier-Villars.
A. S. Dimoglo, et al., Electronic-topological investigations of the relationship between chemical structure and ambergris odor, New Journal of Chemistry, Dec. 1995, pp. 1217-1226, vol. 19, CNRS—Gauthier-Villars.
P.F. Vlad, The Chemistry of Perfume Based on Labdane Diterpenoids, Russian Chemical Reviews, 1982, pp. 1129-1156, vol. 51, Issue 7.
Stefan Neumann, et al., Purification, Partial Characterization and Substrate Specificity of a Squalene Cyclase from Bacillus acidocaldarius, Biological Chemistry Hoppe-Seyler, Aug. 1986, pp. 723-729, vol. 367, Walter de Gruyter & Co., Berlin, New York.
D Ochs, et al., Cloning, expression, and sequencing of squalene-hopene cyclase, a key enzyme in triterpenoid metabolism, Journal of Bacteriology, Jan. 1992, pp. 298-302, vol. 174, Issue 1, American Society for Microbiology.
Ina G. Reipen, et al., Zymomonas mobilis squalene-hopene cyclase gene (shc): cloning, DNA sequence analysis, and expression in *Escherichia coli*, Microbiology, 1995, pp. 155-161, vol. 141, Great Britain.
Miriam Seitz, et al., Substrate specificity of a novel squalene-hopene cyclase from Zymomonas mobilis, Journal of Molecular Catalysis B: Enzymatic, Feb. 25, 2012, pp. 72-77, Issue 84, Elsevier.
D. L. J. Opdyke, et al., Monographs on fragrance raw materials (Part I), Food and Chemical Toxicology, Pergamon, Jan. 1, 1982, p. 695, vol. 20, Issue 6.
Seckler, et al., Characterization and partial purification of squalene-hopene cyclase fromBacillus acidocaldarius, Biochimica et Biophysica Acta (BBA)—General Subjects, May 2, 1986, pp. 356-363, vol. 881, Issue 3.

* cited by examiner

*Primary Examiner* — Robert J Yamasaki
*Assistant Examiner* — Charles Zoltan Constantine
(74) *Attorney, Agent, or Firm* — Curatolo Sidoti & Trillis Co., LPA; Floyd Trillis, III; Salvatore A. Sidoti

(57) ABSTRACT

An enzyme-mediated method for the production of 3a-ethyl-6,6,9a-trimethyldodecahydronaphtho[2,1-b]furan, the products of said method, and uses of said products.

16 Claims, 4 Drawing Sheets

Specification includes a Sequence Listing.

FIG. 2
ZmoSHC2
BjaSHC
OmoSHC
ApaSHC1
ZmoSHC1
AacSHC
TelSHC

Formula (IIa)

ENZYME MEDIATED PROCESS

CROSS REFERENCE TO RELATED APPLICATIONS

This application is a national stage application of International Application No. PCT/EP2020/084508, filed 3 Dec. 2020, which claims priority from Great Britain Patent Application No. 1917694.0, filed 4 Dec. 2019, both of which applications are incorporated herein by reference.

SEQUENCE LISTING

Attached to this Amendment is a Sequence Listing as filed in the International application. The Sequence Listing includes sequences for SEQ ID NOS: 1-23. Please add the Sequence Listing to the present application.

TECHNICAL FIELD

The present invention generally relates to 3a-ethyl-6,6,9a-trmethyldodecahydro-naphtho[2,1-b]furan and to a method of making 3a-ethyl-6,6,9a-trimethyldodecahydronaphtho[2,1-b]furan using squalene-hopene cyclase (SHC) enzyme or enzyme variant. The invention further relates to compositions comprising 3a-ethyl-6,6,9a-trimethyldodecahydronaphtho[2,1-b]furan and the various uses of 3a-ethyl-6,6,9a-trimethyldodecahydronaphtho[2,1-b]furan and compositions comprising 3a-ethyl-6,6,9a-trimethyldodecahydronaphtho[2,1-b]furan. The present invention also relates to consumer products comprising 3a-ethyl-6,6,9a-trimethyldodecahydronaphtho[2,1-b]furan and compositions comprising 3a-ethyl-6,6,9a-trimethyldodecahydronaphtho[2,1-b]furan.

BACKGROUND

There is an ongoing need in the fragrance industry to provide new compounds for use in fragrance compositions. (−)-Ambrox provides an ambery, dry, woody odour that is useful in fragrance compositions alone or in combination with other woody or ambery ingredients. It is therefore desirable to provide new compounds that may provide an ambery odour. US 2009/0131300, the contents of which are incorporated herein by reference, discloses a mixture of stereoisomers of structure I below, as well as the individual isomeric components:

Structure I

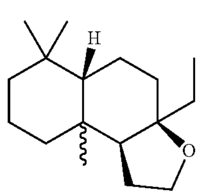

However, US 2009/0131300 teaches that the substituents on the tetrahydrofuranyl ring are cis-configured. In addition, the stereoisomers of structure I of US 2009/0131300 are synthesized in racemic form by a lengthy process involving 9 steps from ethyl-dihydro-ionone. It is therefore desirable to provide new compounds and compositions that provide an ambery odour and to provide new methods for making said compounds. It would not be obvious to make a compound of formula (I) as specified in the present claims in view of the teaching of US 2009/0131300 because US 2009/0131300 teaches that another isomer is preferred and there is no teaching at all with regard to specific enantiomers. The novel method disclosed herein provides access to specific enantiomers.

SUMMARY

In accordance with a first aspect of the present invention there is provided a method for making a compound of formula (I), Formula (I)

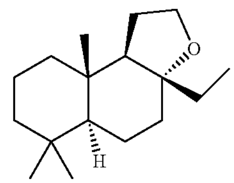

wherein the method comprises contacting a compound of formula (II) with a squalene-hopene cyclase (SHC) enzyme or enzyme variant.

Formula (II)

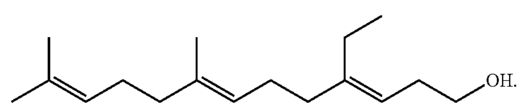

In certain embodiments, the method comprises contacting a compound of formula (IIa) with a squalene-hopene cyclase (SHC) enzyme or enzyme variant, Formula (IIa)

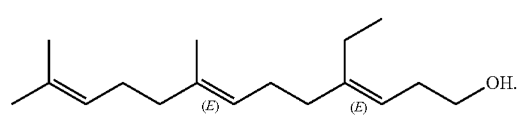

In certain embodiments, the method comprises contacting composition comprising a compound of formula (IIa) and a compound of formula (IIb) with a squalene-hopene cyclase SHC) enzyme or enzyme variant, Formula (IIa)

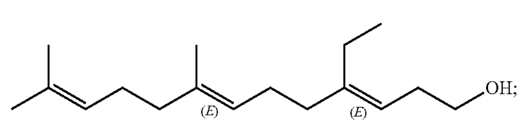

Formula (IIb)

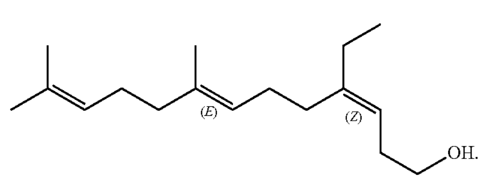

In certain embodiments, the weight ratio of the compound of formula (IIa) to the compound of formula (IIb) ranges from about 5:1 to about 15:1, for example from about 8:1 to about 10:1.

In accordance with a second aspect of the present invention there is provided a compound of formula (I), Formula (I)

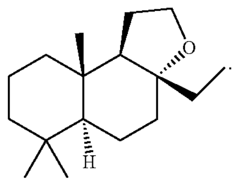

In accordance with a third aspect of the present invention there is provided a composition comprising, consisting essentially of, or consisting of a compound of formula (and a compound of formula (III), Formula (I)

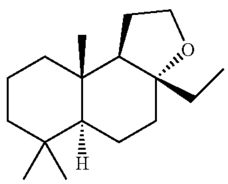

Formula (III)

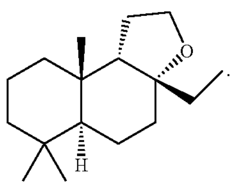

In accordance with a fourth aspect of the present invention there is provided a compound or composition obtainable by or obtained by the method of the first aspect of the present invention. The compound or composition may, for example, be as defined in the second or third aspect of the present invention respectively, including any embodiment thereof.

In accordance with a fifth aspect of the present invention there is provided a use of a compound or composition of the second, third, or fourth aspect of the present invention in or as a fragrance composition.

In accordance with a sixth aspect of the present invention there is provided a consumer product comprising a compound or composition of the second, third, or fourth aspect of the present invention.

In accordance with a seventh aspect of the present invention there is provided a compound of formula (II), Formula (II)

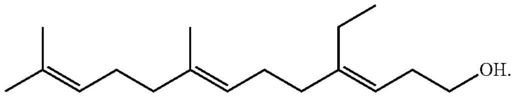

In accordance with an eighth aspect of the present invention there is provided a composition comprising, consisting essentially of, or consisting of a compound of formula (II). The composition of the eighth aspect of the present invention may, for example, comprise, consist essentially of, or consist of a compound of formula (IIa) alone, or of a compound of formula (IIa) and a compound of formula (IIb)

Formula (IIa)

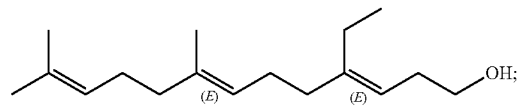

Formula (IIb)

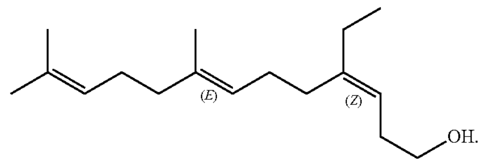

In certain embodiments, the weight ratio of the compound of formula (IIa) to the compound of formula (IIb) ranges from about 5:1 to about 15:1, for example from about 8:1 to about 10:1.

Certain embodiments of the present invention may provide one or more of the following advantages:

- provision of non-regular terpene chains (not following isoprene rule) in contrast to prior art which only discloses regular terpene chains;
- provision of new intermediates to produce 3a-ethyl-6,6,9a-trimethyldodecahydro-naphtho[2,1-b]furan;
- biocatalytic route to produce 3a-ethyl-6,6,9a-trimethyldodecahydronaphtho[2,1-b]furan;
- provision of an ultimately biodegradable product.

The details, examples and preferences provided in relation to any particular one or more of the stated aspects of the present invention will be further described herein and apply equally to all aspects of the present invention. Any combination of the embodiments, examples and preferences described herein in all possible variations thereof is encompassed by the present invention unless otherwise indicated herein, or otherwise clearly contradicted by context.

SUMMARY OF THE SEQUENCES

Figure 1:
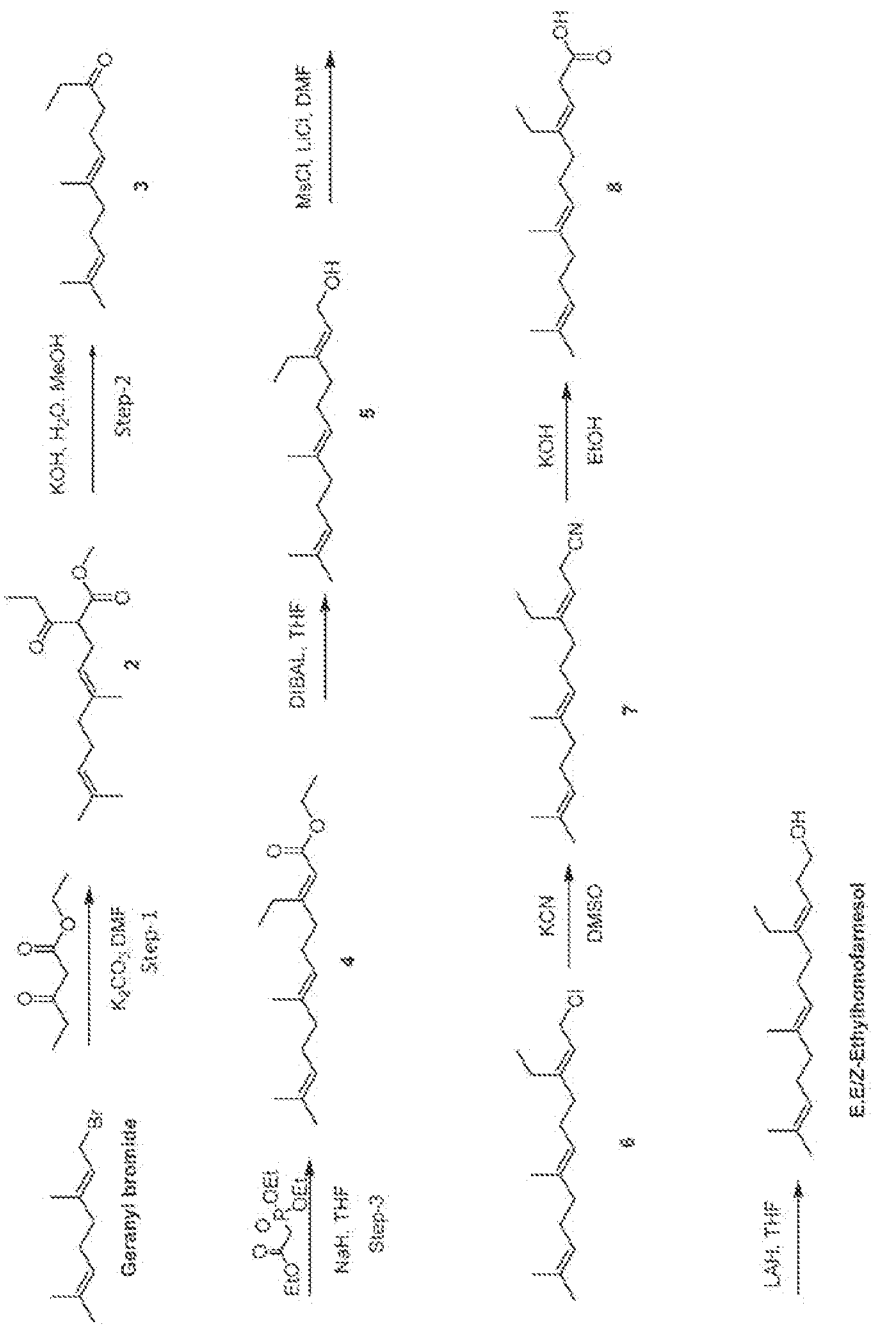
FIG. 1 shows the reaction scheme used to produce a mixture of E,E/Z-ethyl-homofarnesol (i.e. a mixture of compound of formula (IIa) and compound of formula (IIb)).

SEQ ID NO: 1 is the wild-type *Alicyclobacillus acidocaldarius* (Aac) SHC amino acid sequence.

SEQ ID NO: 2 corresponds to SEQ ID NO: 1 with the substitutions M132R, A224V, I432T, A557T and H431L and may be referred to as SHC enzyme variant #49 herein.

SEQ ID NO: 3 corresponds to SEQ ID NO: 1 with the substitutions M132R. A224V, I432T, A557T and R613S and may be referred to as SHC enzyme variant #65 herein.

SEQ ID NO: 4 corresponds to SEQ ID NO: 1 with the substitutions M132R, A224V, I432T, Y81H, A557T and R613S and may be referred to as SHC enzyme variant #66 herein.

SEQ ID NO: 5 corresponds to SEQ ID NO: 1 with the substitutions M132R, A224V, I432T, Y81H, H431L and A557T and may be referred to as SHC enzyme variant #110B8 herein.

SEQ ID NO: 6 is the nucleic acid sequence encoding the polypeptide of SEQ ID NO: 2 (SHC enzyme variant #49).

SEQ ID NO: 7 is the nucleic acid sequence encoding the polypeptide of SEQ ID NO: 3 (SHC enzyme variant #65).

SEQ ID NO: 8 is the nucleic acid sequence encoding the polypeptide of SEQ ID NO: 4 (SHC enzyme variant #66).

SEQ ID NO: 9 is the nucleic acid sequence encoding the polypeptide of SEQ ID NO: 5 (SHC enzyme variant #110B8).

SEQ ID NO: 10 may be referred to as 215G2SHC and corresponds to the wild-type AacSHC amino acid sequence with the mutations M132R, A224V and I432T.

SEQ ID NO: 11 is the wild-type amino acid sequence of ZmoSHC1.

SEQ ID NO: 12 is the wild-type amino acid sequence of ZmoSHC2.

SEQ ID NO: 13 is the wild-type amino acid sequence of BjpSHC/BjaSHC.

SEQ ID NO: 14 is the wild-type amino acid sequence of GmoSHC.

SEQ ID NO: 15 is the nucleotide sequence encoding the wild-type AacSHC.

SEQ ID NO: 16 is the nucleotide sequence encoding 215G2SHC.

SEQ ID NO: 17 corresponds to SEQ ID NO: 1 with the substitutions M132R, A224V, I432T, T90A and R613S and may be referred to as SHC enzyme variant #90C7 herein.

SEQ ID NO: 18 corresponds to SEQ ID NO: 1 with the substitutions M132R, A224V, I432T, A172T and M277K and may be referred to as SHC enzyme variant #115A7 herein.

SEQ ID NO: 19 is the wild-type amino acid sequence of TelSHC.

SEQ ID NO: 20 is the wild-type amino acid sequence of ApaSHC1.

SEQ ID NO: 21 is a GmoSHC variant.

SEQ ID NO: 22 is the nucleotide sequence encoding the polypeptide of SEQ ID NO: 17 (SHC enzyme variant #90C7).

SEQ ID NO: 23 is the nucleotide sequence encoding the polypeptide of SEQ ID NO: 18 (SHC enzyme variant #115A7).

DETAILED DESCRIPTION

The present invention is based, at least in part, on the surprising finding that (3aR,5aS,9aS,9bR)-3a-ethyl-6,6,9a-trimethyldodecahydronaphtho[2,1-b]furan, i.e. one enantiomer of formula (I), provides a strong odour. This is surprising in view of the teaching in US 2009/0131300 that another isomer is preferred. The present invention is further based on the surprising finding that squalene-hopene cyclase (SHC) enzyme or enzyme variant can be used to make the compound of formula (I) from a compound of formula (II) having a non-regular terpene chain.

Thus, there is provided herein a method of making a compound of formula (I),

Formula (I)

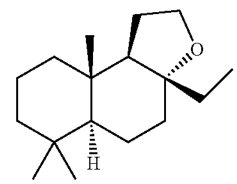

wherein the method comprises contacting a compound of formula (II) with a squalene-hopene cyclase (SHC) enzyme or enzyme variant.

Formula (II)

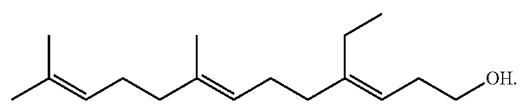

The compound of formula (I) is a new compound that has surprisingly been found to have a strong odour. Therefore, there is also provided herein a compound of formula (I). There is further provided herein the use of compound of formula (I) as fragrance, a composition comprising a compound of formula (I) and optionally a compound of formula (III).

The methods provided herein enzymatically convert a compound of formula (II) to a compound of formula (I) using an SHC enzyme or enzyme variant.

Compound of Formula (II)

The compound of formula (II) may, for example, be referred to as ethyl-homofarnesol. The compound of formula (II) may, for example, be a compound of formula (IIa) (having E,E-configuration) or a compound of formula (IIb) (having E,Z-configuration). The compounds of formula (IIa) and (IIb) are stereoisomers of the compound of formula (II). Other stereoisomers of the compound of formula (II) are compounds of formula (IIc) and (IId) shown below.

Formula (IIc)

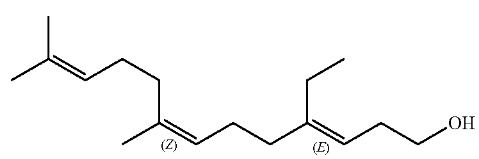

Formula (IId)

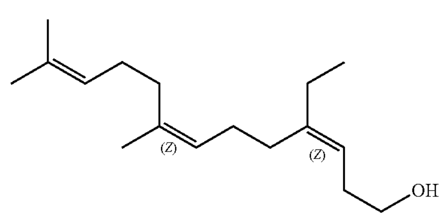

The compound of formula (II) may, for example, be a mixture of stereoisomers comprise, consist essentially of or consist of a compound of formula (IIa) and a compound of formula (IIb). The mixture may or may not, for example, comprise any other stereoisomers of formula (II).

In certain embodiments, the method comprises contacting a compound of formula (IIa) with a squalene-hopene cyclase (SHC) enzyme or enzyme variant, Formula (IIa)

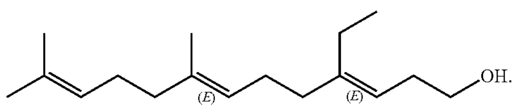

In certain embodiments, the method comprises contacting a compound of formula (IIa) with a squalene-hopene cyclase (SHC) enzyme or enzyme variant in the absence of any other stereoisomers of formula (II) (e.g. in the absence of a compound of formula (IIb)), Formula (IIb)

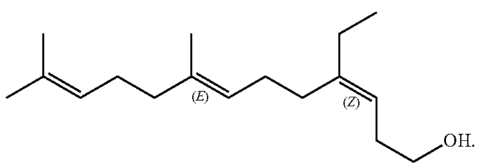

In other embodiments, the compound of formula (II) may, for example, be a mixture of stereoisomers of formula (II). In certain embodiments, the mixture comprises a compound of formula (IIa) and one or more other stereoisomers of formula (II). In certain embodiments, the mixture comprises a compound of formula (Jib) and one or more other stereoisomers of formula (ii).

In certain embodiments, the method comprises contacting a composition comprising, consisting essentially of, or consisting of a compound of formula (IIa) and a compound of formula (IIb) with an SHC enzyme or enzyme variant. In certain embodiments, the composition does not comprise any other stereoisomers of formula (II).

The weight ratio of the compound of formula (IIa) to total other stereoisomers of formula (II) may, for example, be equal to or greater than about 10:90. For example, the weight ratio of the compound of formula (IIa) to total other stereoisomers of formula (II) may be equal to or greater than about 20:80 or equal to or greater than about 30:70 or equal to or greater than about 40:60 or equal to or greater than about 50:50 or equal to or greater than about 60:40 or equal to or greater than about 70:30 or equal to or greater than about 80:20 or equal to or greater than about 90:10 or equal to or greater than about 95:5.

The weight ratio of the compound of formula (IIa) to total other stereoisomers of formula (II) may, for example, be equal to or less than about 99:1. For example, the weight ratio of the compound of formula (IIa) to total other stereoisomers of formula (II) may be equal to or less than about 95:5 or equal to or less than about 90:10 or equal to or less than about 85:15 or equal to or less than about 80:20.

For example, the weight ratio of the compound of formula (IIa) to total other stereoisomers of formula (II) may range from about 10:90 to about 99:1 or from about 10:90 to about 90:10 or from about 20:80 to about 80:20 or from about 50:50 to about 80:20 or from about 60:40 to about 80:20.

The weight ratio of the compound of formula (IIa) to the compound of formula (IIb) may, for example, be equal to or greater than about 10:90. For example, the weight ratio of the compound of formula (IIa) to the compound of formula (IIb) may be equal to or greater than about 20:80 or equal to or greater than about 30:70 or equal to or greater than about 40:60 or equal to or greater than about 50:50 or equal to or greater than about 60:40 or equal to or greater than about 70:30 or equal to or greater than about 80:20 or equal to or greater than about 90:10 or equal to or greater than about 95:5.

The weight ratio of the compound of formula (IIa) to the compound of formula (IIb) may, for example, be equal to or less than about 99:1. For example, the weight ratio of the compound of formula (IIa) to the compound of formula (IIb) may be equal to or less than about 96:5 or equal to or less than about 90:10 or equal to or less than about 85:15 or equal to or less than about 80:20.

The weight ratio of compound of formula (IIa) to compound of formula (IIb) may, for example, range from about 5:1 to about 15:1. For example, the weight ratio of compound of formula (IIa) to compound of formula (IIb) may range from about 6:1 to about 14:1 or from about 7:1 to about 13:1 or from about 8:1 to about 12:1 or from about 8:1 to about 11:1 or from about 8:1 to about 10:1. For example, the weight ratio of compound of formula (IIa) to compound of formula (IIb) may be about 9:1. Other stereoisomers of formula (II) include the compound of formula (IIc) and the compound of formula (IId), Formula (IIc)

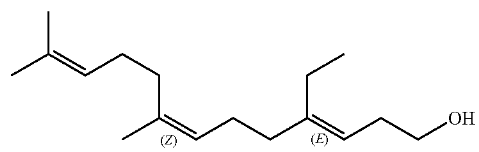

Formula (IId)

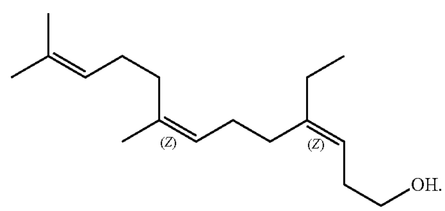

The amount of each stereoisomer in a mixture of stereoisomers may, for example, be identified by gas chromatography or NMR spectroscopy.

In certain embodiments, not all compounds of formula (II) are converted to a compound of formula (I) or a by-product of the reaction. Thus, in certain embodiments, the compositions described herein, for example the compositions obtained by or obtainable by the methods described herein, may comprise a compound of formula (I) and a compound of formula (II), for example one or more of a compound of formula (IIIa), (IIb), (IIc) and/or (IId). In particular, the compositions described herein may comprise a compound of formula (IIIa) and/or a compound of formula (IIb). In certain embodiments, any remaining compound of formula (II) in the compositions made by the methods described herein may be separated from the other reaction products such that the composition does not comprise a compound of formula (II).

In alternative embodiments, all compounds of formula (II) are converted to a compound of formula (I) or a compound of formula (III).

The number of stereoisomers of the compound of formula (II) present may influence the speed of the reaction. An SHC enzyme or enzyme variant may be capable of cyclizing a compound of formula (IIa) to a compound of formula (I) from a complex mixture of stereoisomers of the compound of formula (II). However, a lower conversion rate may be observed, which is consistent with the view that stereoisomers of formula (IIb), (IIc) and/or (IId) may compete with the compound of formula (IIa) for access to the SHC enzyme or enzyme variant and thus may act as competitive inhibitors for the conversion of the compound of formula (IIIa) to the compound of formula (I) and/or also act as alternative substrates. Accordingly, the compound of formula (II) substrate may comprise an isomeric mixture of 2-4 isomers, preferably two isomers. In one particular embodiment, the compound of formula (II) substrate comprises, consists essentially of or consists of an (IIa):(IIb) isomeric mixture.

A composition comprising a compound of formula (IIa) and a compound of formula (IIb) may, for example, be made by the method described in Example 1 below.

In a further particular embodiment, the compound of formula (II) substrate comprises, consists essentially of or consists of (IIa).

Compound of Formula (I) and Stereoisomers Thereof

The compound of formula (I) has the relative configuration shown in the structures provided herein which encompasses two enantiomers ((3aR,5aS,9aS,9bR)-3a-ethyl-6,6,9a-trimethyldodecahydronaphtho[2,1-b]furan and (3aS,5aR,9aR,9bS)-3a-ethyl-6,6,9a-trimethyldodecahydronaphtho[2,1-b]furan).

Formula (I)

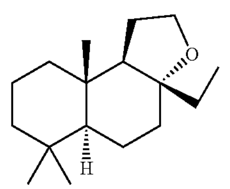

The compound of formula (I) contains a number of chiral carbon atoms and thus other stereoisomers may also exist, including enantiomers and diastereomers, for example a compound of formula (III) which encompasses two enantiomers (3aR,5aS,9aS,9bS)-3a-ethyl-6,6,9a-trimethyldodecahydronaphtho[2,1-b]furan and (3aS,5aR,9aR,9bR)-3a-ethyl-6,6,9a-trimethyldodecahydronaphtho[2,1-b]furan). In addition to the compound of formula (I), the products made by the methods described herein may include a compound of formula (III)

Formula (III)

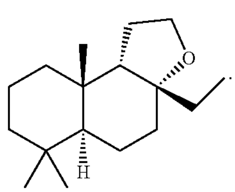

In certain embodiments, no other stereoisomers of the compound of formula (I) are made by the method or are present in the product of the method, e.g. in certain embodiments a compound of formula (III) is not made by the method or are present in the product of the method.

The methods described herein may, for example, make a compound of formula (I) and optionally a compound of formula (III)). Thus, the compositions described herein, for example the compositions obtained by or obtainable by the methods described herein may comprise a compound of formula (I) and optionally a compound of formula (III).

The weight ratio of the compound of formula (I) to the compound of formula (III) may, for example be equal to or greater than about 50:50. For example, the weight ratio of the compound of formula (I) to the compound of formula (III) may be equal to or greater than about 55:45 or equal to or greater than about 60:40 or equal to or greater than about 65.35 or equal to or greater than about 70:30 or equal to or greater than about 75:25 or equal to or greater than about 80:20 or equal to or greater than about 85:15 or equal to or greater than about 90:10 or equal to or greater than about 95:5 or equal to or greater than about 97:3 or equal to or greater than about 98:2 or equal to or greater than about 99:1.

In one embodiment, the mixture comprising a compound of formula (I) and other stereoisomers may comprise from about 50 wt % to about 100 wt % or from about 60 wt % to about 99 wt % or from about 70 wt % to about 98 wt % or from about 80 wt % to about 97 wt % or from about 90 wt % to about 97 wt % of the compound of formula (I) based on the total weight of the compound of formula (I) and other stereoisomers.

For example, the weight ratio of the compound of formula (I) to total other stereoisomers may be from about 50:50 to about 100:0 or from about 60.40 to about 99:1 or from about 70:30 to about 98:2 or from about 80:20 to about 97:3 or from about 90:10 to about 97:3.

In certain embodiments the compound of formula (I) is enantioenriched.

By "enantioenriched" we mean a mixture comprising (3aR,5aS,9aS,9bR)-3a-ethyl-6,6,9a-trimethyldodecahydronaphtho[2,1-b]furan and (3aS,5aR,9aR,9bS)-3a-ethyl-6,6,9a-trimethyldodecahydronaphtho[2,1-b]furan in a weight ratio from 55:45 to 100:0. For example, the weight ratio may be equal to or greater than about 60:40 or equal to or greater than about 65:35 or equal to or greater than about 70:30 or equal to or greater than about 75:25 or equal to or greater than about 80:20 or equal to or greater than about 85.15 or equal to or greater than about 90:10 or equal to or greater than about 95:5 or equal to or greater than about 97:3 or equal to or greater than about 98:2 or equal to or greater than about 99:1.

The amount of each stereoisomer in a mixture of stereoisomers may, for example, be identified by gas chromatography or NMR spectroscopy.

The term "isolated" as used herein refers to a cyclization product such as the compound of formula (I) which has been separated or purified from components which accompany it. The purity can be measured by any appropriate method, e.g. gas chromatography (GC), HPLC or NMR analysis.

Desirably, the amount of compound of formula (I) produced can be from about 1 mg/l to about 20,000 mg/l (20 g/l) or higher such as from about 20 g/l to about 200 g/l or from 100-200 g/l, preferably about 125 g/l or 150 g/l or about 188 g/l.

For example about 1 to about 100 mg/1, about 30 to about 100 mg/l, about 50 to about 200 mg/l, about 100 to about 500 mg/l, about 100 to about 1,000 mg/l, about 250 to about 5,000 mg/l, about 1,000 (1 g/l) to about 15.000 mg/l (15 g/l), or about 2,000 (2 g/l) to about 10,000 mg/l (10 g/l) or about 2,000 (2 g/l) to about 25,000 mg/l (25 g/l) or about 2,000 (2 g/l) to about 25,000 mg/l (25 g/l), 26.000 mg/l (26 g/l), 27,000 mg/l (27 g/l), 28,000 mg/l (28 g/l), 29,000 mg/l (29 g/l), 30,000 mg/l (30 g/l), 40 g/l, 50 g/l, 60 g/l, 70 g/l, 80 g/l, 90 g/l, 100 g/l, 110 g/l, 120 g/l, 125 g/l, 130 g/l, 140 g/l, 150 g/l, 160 g/l, 170 g/l, 1809/1, 190 g/l or 200 g/l or 300 g/l or 400 g/i or 500 g/l of compound of formula (I) may be produced.

Preferably a compound of formula (I) at a concentration of at least 100 g/l is produced within a period of time from 48 to 72 hours.

Preferably compound of formula (I) at a concentration of about 150 g/l is produced within a time period of from about 48 to 72 hours. Preferably compound of formula (I) at a concentration of about 200 g/l is produced within a time period of from about 48 to 72 hours.

Preferably compound of formula (I) at a concentration of about 250 g/1 is produced within a time period of from about 48 to 72 hours.

Products Obtained by the Methods Described Herein

There is also provided herein the products of the methods described herein. Thus, there is also provided herein a compound or a composition obtained by or obtainable by the method described herein, including all embodiments thereof.

Thus, there is provided herein a compound of formula (I) or a composition comprising a compound of formula (I).

There is also provided herein a composition comprising, consisting essentially of, or consisting of a compound of formula (I) and a compound of formula (III). Additionally or alternatively, the composition may further comprise any unreacted compound of formula (II).

The weight ratio of the compound of formula (I) to the compound of formula (III) in the compositions described herein may, for example, range from about 60:40 to about 99:1. For example, the weight ratio of the compound of formula (I) to the compound of formula (III) may range from about 65:35 to about 99:1 or from about 70:30 to about 99:1 or from about 75:25 to about 99:1 or from about 80:20 to about 99:1 or from about 85:15 to about 99:1 or from about 90:10 to about 99:1 or from about 95:5 to about 99:1. For example, the weight ratio of the compound of formula (I) to the compound of formula (III) may range from about 65:35 to about 98:2 or from about 70:30 to about 97:3 or from about 75:25 to about 96:4 or from about 80:20 to about 95:5 or from about 85:15 to about 90:10.

The weight ratio of the compound of formula (I) to the compound of formula (II) in the compositions described herein may, for example, range from about 90:10 to about 100:0. For example, the weight ratio of the compound of formula (I) to the compound of formula (II) in the compositions described herein may range from about 92:8 to about 100:0 or from about 94:6 to about 100:0 or from about 95:5 to about 100:0 or from about 96:4 to about 99.5:0.5 or from about 97:3 to about 99.0:1.0 or from about 98:2 to about 99.0:1.0.

Fragrance Compositions

There is further provided herein the use of the compounds and compositions described herein as or in a fragrance composition.

Thus, there is also provided herein a fragrance composition comprising a compound of formula (I). By "fragrance composition" is meant any composition comprising a compound of formula (I) and a base material.

As used herein, the "base material" includes all known fragrance ingredients selected from the extensive range of natural products, and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, diluents, and other auxiliary agents commonly used in the art.

Fragrance ingredients known to the art are readily available commercially from the major fragrance manufacturers. Non-limiting examples of such ingredients include:

- essential oils and extracts, e.g. castoreum, costus root oil, oak moss absolute, geranium oil, tree moss absolute, basil oil, fruit oils, such as bergamot oil and mandarine oil, myrtle oil, palmarose oil, patchouli oil, petitgrain oil, jasmine oil, rose oil, sandalwood oil, wormwood oil, lavender oil and/or ylang-ylang oil;
- alcohols, e.g. cinnamic alcohol ((E)-3-phenylprop-2-en-1-ol); cis-3-hexenol ((2)-hex-3-en-1-ol); citronella, (3,7-dimethyloct-6-en-1-ol); dihydro myrcenol (2,6-dimethyloct-7-en-2-ol); Ebanol™ ((E)-3-methyl-5-(2,2,3-trimethylcyclopent 3-en-1-yl)pent-4-en-2-ol); eugenol (4-ally)-2-methoxyphenol); ethyl linalool ((E)-3,7-dimethylnona-1,6-dien-3-ol); farnesol ((2E,62)-3,7,11-trimethyldodeca-2,6,10-trien-1-ol); geraniol ((E)-3,7-dimethylocta-2,6-dien-1-ol); Super Muguet™ ((E)-6-ethyl-3-methyloct-6-en-1-ol); linalool (3,7-dimethylocta-1,6-dien-3-ol); menthol (2-isopropyl-5-methylcyclohexanol); Nerol (3,7-dimethyl-2,6-octadien-1-ol); phenyl ethyl alcohol (2-phenylethanol); Rhodinol™ (3,7-dimethyloct-6-en-1-ol); Sandalore™ (3-methyl-5-(2,2,3-trimethylcyclopent-3-en-1-yl)pentan-2-ol); terpineol (2-(4-methylcyclohex-3-en-1-yl) propan-2-ol); or Timberol™ (1-(2,2,6-trimethylcyclohexyl)hexan-3-ol); 2,4,7-trimethylocta-2,6-dien-1-ol, and/or [1-methyl-2(5-methylhex-4-en-2-yl)cyclopropyl]-methanol;
- aldehydes and ketones, e.g. anisaldehyde (4-methoxybenzaldehyde); alpha amyl cinnamic aldehyde (2-benzylideneheptanal); Georgywood™ (1-(1,2,8,8-tetramethyl-1,2,3,4,5,6,7,8-octahydronaphthalen-2-yl) ethanone); Hydroxyciironellal (7-hydroxy-3,7-dimethyloctanal); Iso E Super (1-(2,3,8,8 tetramethyl-1,2,3,4,5,6,7,8-octahydronaphthalen-2-yl)ethanone); Isoraldeine ((E)-3-methyl-4-(2,6,6-trimethylcyclohex-2-en-1-yl)but-3-en-2-one); 3-(4-isobutyl-2-methylphenyl)propanal; maltol; methyl cedryl ketone; methylionone; verbenone; and/or vanillin;
- ether and acetals, e.g. Ambrox® (3a,6,6,9a-tetramethyl-2,4,5,5a,7,8,9,9b-octahydro-1H-benzo[e][1]benzofuran); geranyl methyl ether ((2E)-1-methoxy-3,7-dimethylocta-2,6-diene); rose oxide (4-methyl-2-(2-methylprop-1-en-1-yl)tetrahydro-2H-pyran); and or Spirambrene® (2',2',3,7,7-pentamethylspiro[bicyclo [4.1.0]heptane-2,5'-(1,3)dioxane]);
- macrocycles, e.g. Ambrettolide ((Z)-oxacycloheptadec-10-en-2-one); ethylene brassylate (1,4-dioxacycloheptadecane-5,17-dione); and/or Exaltolide™ (16-oxacyclohexadecan-1-one); and
- heterocycles, e.g. isobutylquinoline (2-isobutylquinoline).

As used herein, "carrier material" means a material which is practically neutral from an odorant point of view, i.e. a material that does not significantly alter the organoleptic properties of odorants.

By "diluents" is meant any diluent conventionally used in conjunction with odorants, such as diethyl phthalate (DEP), dipropylene glycol (DPG), isopropyl myristate (IPM), triethyl citrate (TEC) and alcohol (e.g. ethanol).

The term "auxiliary agent" refers to ingredients that might be employed in a fragrance composition for reasons not specifically related to the olfactive performance of said composition. For example, an auxiliary agent may be an ingredient that acts as an aid to processing a fragrance ingredient or ingredients, or a composition containing said ingredient(s), or it may improve handling or storage of a fragrance ingredient or composition containing same, such as anti-oxidant adjuvant. Said anti-oxidant may be selected, for example, from Tinogard® TT (BASF), Tinogard® Q (BASF), Tocopherol (including its isomers, CAS 59-02-9; 364-49-8; 18920-62-2; 121854-78-2), 2,6-bis(1,1-dimethylethyl)-4-methylphenol (BHT, CAS 128-37-0) and related phenols, hydroquinones (CAS 121-31-9).

It might also be an ingredient that provides additional benefits such as imparting colour or texture. It might also be an ingredient that imparts light resistance or chemical stability to one or more ingredients contained in a fragrance composition. A detailed description of the nature and type of auxiliary agent commonly used in fragrance compositions containing same cannot be exhaustive, but it has to be mentioned that said ingredients are well known to a person skilled in the art.

Various applications for the compound of formula (I) include but are not limited to a fine fragrance or a consumer product such as fabric care, toiletries, beauty care and leaning products, detergent products, and soap products.

There is also provided herein a consumer product comprising a compound or a composition or fragrance composition as described herein, including any embodiment thereof. The consumer product may, for example, be a cosmetic product (e.g. an eau de parfum or eau de toilette), a cleaning product, a detergent product, or a soap product Intermediates and Starting Materials There is also provided herein the intermediates and starting materials used in the methods described herein.

Thus, there is also provided herein a compound of formula (II),

Formula (II)

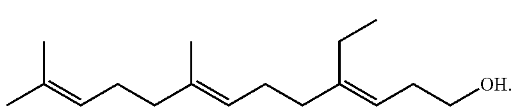

There is also provided herein a composition comprising, consisting essentially of, or consisting of a compound of formula (II). For example, the composition may comprise, consist essentially of, or consist of a compound of formula (IIa) and a compound of formula (IIb).

Formula (IIa)

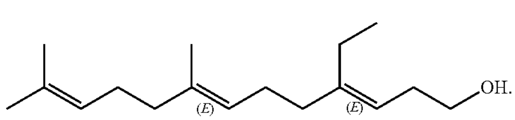

-continued

Formula (IIb)

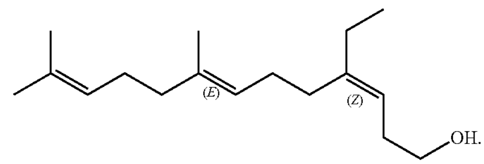

The weight ratio of the compound of formula (IIa) to the compound of formula (I*b*) may, for example, be equal to or greater than about 10:90. For example, the weight ratio of the compound of formula (IIa) to the compound of formula (IIb) may be equal to or greater than about 20:80 or equal to or greater than about 30:70 or equal to or greater than about 40:60 or equal to or greater than about 50:50 or equal to or greater than about 60:40 or equal to or greater than about 70:30 or equal to or greater than about 80.20 or equal to or greater than about 90:10 or equal to or greater than about 95:5.

The weight ratio of the compound of formula (IIa) to the compound of formula (IIb) may, for example, be equal to or less than about 99:1. For example, the weight ratio of the compound of formula (IIa) to the compound of formula (IIb) may be equal to or less than about 95:5 or equal to or less than about 90:10 or equal to or less than about 85:15 or equal to or less than about 80:20.

The weight ratio of compound of formula (IIa) to compound of formula (IIb) may, for example, range from about 5:1 to about 15:1. For example, the weight ratio of compound of formula (IIa) to compound of formula (IIb) may range from about 6:1 to about 14:1 or from about 7:1 to about 13:1 or from about 8:1 to about 12:1 or from about 8:1 to about 11:1 or from about 8:1 to about 10:1. For example, the weight ratio of compound of formula (IIa) to compound of formula (IIb) may be about 9:1.

The compound of formula (II) or composition comprising one or more compound(s) of formula (II) may, for example, be used to make a compound of formula (I), for example in accordance with the methods described herein using a SHC enzyme or enzyme variant.

The composition comprising a compound of formula (II) may, for example, further comprise one or more other materials. The one or more other materials may, for example, be a diluent, excipient, or carrier material.

SHC Enzyme or Enzyme Variant

The methods described herein use an SHC enzyme or enzyme variant to enzymatically convert a compound of formula (II) to a compound of formula (I).

As used herein, the term "SHC enzyme" means a wild-type (WT) Squalene Hopene Cyclase enzyme that is naturally occurring, for example, in a thermophilic bacterium such as *Alicyclobacillus acidocaldarius*.

As used herein, the term "variant" is to be understood as a polypeptide which differs in comparison to the polypeptide from which it is derived by one or more changes in the amino acid sequence. The polypeptide from which a variant is derived is also known as the parent or reference polypeptide. Typically a variant is constructed artificially, preferably by gene-technological means. Typically, the polypeptide from which the variant is derived is a wild-type protein or wild-type protein domain. However, the variants usable in the present disclosure may also be derived from homologs, orthologs, or paralogs of the parent polypeptide or from artificially constructed variants, provided that the variant exhibits at least one biological activity of the parent polypeptide. The changes in the amino acid sequence may be amino acid exchanges (substitutions), insertions, deletions, N-terminal truncations, or C-terminal truncations, or any combination of these changes, which may occur at one or several sites.

As used herein, the term "SHC enzyme variant" means an enzyme that is derived from a wild-type SHC enzyme but has one or more amino acid alterations compared to the wild-type SHC enzyme and is therefore not naturally occurring. The one or more amino acid alterations may, for example, modify (e.g. increase) the enzymatic activity for a substrate (e.g. compound of formula (II)).

A number of wild-type and variant SHC enzymes from a variety of bacteria are disclosed, for example, in the following documents: WO 2016/170099; WO 2018/157021; Neumann & Simon 1986, Biol Chem Hoppe-Seyler 367, 723-729; JP2009060799; Seckler & Poralla 1986, Biochem Biophys Act 356-363; Ochs et at 1990, J Bacteriol 174, 298-302; WO 2010/139719; U.S. Pat. No. 8,759,043; WO 2012/066059; Seitz et al 2012, J Molecular Catalysis 8; Enzymatic 84, 72-77; Eichhorn et al 2018, Adv Synth Catal 360, 2339-2351, and Seitz 2012 PhD thesis (http://elib.uni-stuttgart.de/handle/11682/1400), the contents of which are incorporated herein by reference). These SHC enzymes and variants may be used in the methods described herein.

Assays for determining and quantifying SHC enzyme and/or SHC enzyme variant activity are described herein and are known in the art. By way of example, SHC enzyme and/or SHC enzyme variant activity can be determined by incubating purified SHC enzyme or enzyme variant or extracts from host cells or a complete recombinant host organism that has produced the SHC enzyme or enzyme variant with an appropriate substrate under appropriate conditions and carrying out an analysis of the reaction products (e.g. by gas chromatography (GC) or HPLC analysis). Further details on SHC enzyme and/or SHC enzyme variant activity assays and analysis of the reaction products are provided in the Examples. These assays may include producing the SHC enzyme variant in recombinant host cells (e.g. *E. coli*).

As used herein, the term "activity" means the ability of an enzyme to react with a substrate to provide a desired product. The activity can be determined in what is known as an activity test for monitoring the formation of the desired product. The SHC enzyme derivatives of the present disclosure may be characterized by their ability to cyclize the compound of formula (II) to the compound of formula (I).

A "biological activity" as used herein, refers to any activity a polypeptide may exhibit, including without limitation: enzymatic activity; binding activity to another compound (e.g. binding to another polypeptide, in particular binding to a receptor, or binding to a nucleic acid); inhibitory activity (e.g. enzyme inhibitory activity); activating activity (e.g. enzyme-activating activity); or toxic effects. It is not required that the variant exhibits such an activity to the same extent as the parent or wild-type polypeptide. A variant is regarded as a variant within the context of the present application, if it exhibits the relevant activity to a degree of at least 10% of the activity of the parent polypeptide. Likewise, a variant is regarded as a variant within the context of the present application, if it exhibits the relevant biological activity to a degree of at least 10% of the activity of the parent polypeptide (as the terms derivative and variant are used interchangeably throughout the present disclosure). In other embodiments, the SHC enzyme variants used herein allows a better yield than the reference SHC enzyme (e.g. a wild-type SHC enzyme or a known SHC enzyme variant). The term "yield" refers to the gram of recoverable product per gram of feedstock (which can be calculated as a percent molar conversion rate). In additional embodiments, the SHC enzyme variants used herein may show a modified (e.g. increased) productivity relative to the reference SHC enzyme (e.g. wild-type AacSHC or 215G2SHC). The term "productivity" refers to the amount of recoverable product in grams per liter of reaction per hour of reaction time (i.e. time after the substrate was added).

In further embodiments, the SHC enzyme variants of the present disclosure show a modified yield compared with the reference SHC enzyme (e.g. wild-type AacSHC (SEQ ID NO: 1) or 215G2SHC (SEQ ID NO: 10) or wild-type ZmoSHC1 (SEQ ID NO: 11) or wild-type ZmoSHC2 (SEQ ID NO: 12) or wild-type BjpSHC (SEQ ID NO: 13) or wild-type GmoSHC (SEQ ID NO: 14) or wild-type TelSHC (SEQ ID NO: 19) or wild-type ApaSHC1 (SEQ ID NO: 20)). The term "target yield factor" refers to the ratio between the product concentration obtained and the concentration of the SHC variant enzyme (for example, purified SHC enzyme variant or whole cells, or an extract from the recombinant host cells producing the SHC enzyme variant) in the reaction medium. In various embodiments, the SHC enzyme variants of the present disclosure show a modified (e.g. increased) fold increase in enzymatic activity (e.g. a modified/increased cyclization of a compound of formula (II)) relative to the reference SHC protein (e.g. SEQ ID No. 1 or SEQ ID NO: 10 or SEQ ID NO: 11 or SEQ ID NO: 12 or SEQ ID NO: 13 or SEQ ID NO: 14 or SEQ ID NO: 19 or EQ ID NO: 20). This increase in activity may be at least by a factor of: 2, 3, 4, 8, 8, 10, 12, 14, 16, 18, 20, 25, 30, 35, 40, 45, 50, 55, 80, 65, 70, 75, 80, 85, 90, 95, and/or 100.

As used herein, the term "amino acid alteration" means an insertion of one or more amino acids between two amino acids, a deletion of one or more amino acids or a substitution (which may be conservative or non-conservative) of one or more amino acids with one or more different amino acids relative to the amino acid sequence of a reference amino acid sequence. Substitutions replace the amino acids of the reference sequence with the same number of amino acids in the variant sequence. Reference amino acid sequences may, for example, be a wild-type (WT) amino acid sequence (for example SEQ ID NO: 1 or SEQ ID NO: 11 or SEQ ID NO: 12 or SEQ ID NO: 13 or SEQ ID NO: 14 or SEQ ID NO: 19 or SEQ ID NO: 20) or may, for example, itself be a SHC enzyme variant sequence (for example the Aac 215G2SHC variant—SEQ ID NO: 10).

The amino acid alterations can be easily identified by a comparison of the amino acid sequences of the SHC enzyme variant with the amino acid sequence of the reference amino acid sequence.

Conservative amino acid substitutions may be made, for instance, on the basis of similarity in polarity, charge, size, solubility, hydrophobicity, hydrophilicity, and/or the amphipathic nature of the amino acid residues involved. The 20 naturally occurring amino acids as outlined above can be grouped into the following six standard amino acid groups:

(1) hydrophobic: Met, Ala, Val, Leu, Ile;
(2) neutral hydrophilic: Cys, Ser, Thr; Asn, Gln;
(3) acidic: Asp, Glu;
(4) basic: His, Lys, Arg;
(5) residues that influence chain orientation: Gly. Pro; and
(6) aromatic: Trp, Tyr, Phe.

Accordingly, as used herein, the term "conservative substitutions" means an exchange of an amino acid by another amino acid listed within the same group of the six standard amino acid groups shown above. For example, the exchange of Asp by Glu retains one negative charge in the so modified polypeptide. In addition, glycine and praline may be substituted for one another based on their ability to disrupt alpha-helices. Some preferred conservative substitutions within the above six groups are exchanges within the following sub-groups: (i) Ala, Val, Leu and Ile; (ii) Ser and Thr, (ii) Asn and Gln; (iv) Lys and Arg; and (v) Tyr and Phe. Given the known genetic code, and recombinant and synthetic DNA techniques, the skilled scientist readily can construct DNAs encoding the conservative amino acid variants.

As used herein, "non-conservative substitutions" or "non-conservative amino acid exchanges" are defined as exchanges of an amino acid by another amino acid listed in a different group of the six standard amino acid groups (1) to (6) as shown above. Typically the SHC enzyme variants described herein are prepared using non-conservative substitutions which alter the biological function of the disclosed SHC enzyme variants. For ease of reference, the one-letter amino acid symbols recommended by the IUPAC-IUB Biochemical Nomenclature Commission are indicated as follows. The three letter codes are also provided for reference purposes.

| One Letter Code | Three Letter Code | Amino Acid Name |
|---|---|---|
| A | Ala | Alanine |
| C | Cys | Cysteine |
| D | Asp | Aspartic Acid |
| E | Glu | Glutamic Acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Amino acid alterations such as amino acid substitutions may be introduced using known protocols of recombinant gene technology including PCR, gene cloning, site-directed mutagenesis of cDNA, transfection of host cells, and in vitro transcription which may be used to introduce such changes to the reference sequence resulting in an SHC enzyme variant. The enzyme variants can then be screened for SHC functional activity.

Suitable sources of SHC enzymes include, for example, *Alicyclobacillus acidocaldarius* (Mc), *Zymomonas mobilis* (Zmo), *Bradyrhizobium japonicum* (Bjp), *Gluconobacter morbifer* (Gmo), *Burkholderia ambifaria, Bacillus anthracis, Methylococcus capsulatus, Frankia alni, Acetobacter pasteurianus* (Apa), *Thermosynechococcus elongatus* (Tel). *Streptomyces coelicolor* (Sco), *Rhodopseudomonas palustris* (Rpa), *Teredinibacter turnerae* (Ttu), *Pelobacter carbinolicus* (Pca), and *Tetrahymena pyriformis* (see, for example WO 2010/139719, US 2012/01345477, WO 2012/086059, the contents of which are incorporated herein by reference).

In particular, the SHC enzyme (e.g. from which the SHC enzyme variant may be derived) may be the *Alicyclobacillus acidocaldarius* (Aac) SHC enzyme, the *Zymomonas mobilis* (Zmo) SHC enzyme, the *Bradyrhizobium japonicum* (Bjp or Bja) SHC enzyme or the *Gluconobacter morbifer* (Gmo) SHC enzyme. In particular, the SHC enzyme (e.g. from which the SHC enzyme variant may be derived) may be the *Alicyclobacillus acidocaldarius* (Aac) SHC enzyme.

For ease of reference, the designation "AacSHC" may be used to refer to the *Alicyclobacillus acidocaldarius* (Aac) SHC enzyme, "ZmoSHC" may be used to refer to the *Zymomonas mobilis* (Zmo) SHC enzyme, "BjpSHC" or "BjaSHC" may be used to refer to the *Bradyrhizobium japonicum* (Bjp or Bja) SHC enzyme and "GmoSHC" may be used to refer to the *Gluconobacter morbifer* (Gmo) SHC enzyme.

AacSHC, ZmoSHC and BjpSHC enzyme sequences are disclosed in BASF WO 2010/139719, US 2012/01345477A1, Seitz et al (as cited above) and Seitz (2012 PhD thesis as cited above). Two different sequences are disclosed for ZmoSHC, referred to as ZmoSHC1 and ZmoSHC2. The Gmo SHC enzyme sequence is disclosed in WO 2018/157021.

TABLE 1

Sources and accession numbers of wild-type SHC enzymes.

| SHC Source Strain (SHC name) | Reference | Accession No. | SEQ ID No. according to WO2010139719 US2012/0135477 |
|---|---|---|---|
| *Alicyclobacillus acidocaldarius* (WT AacSHC) | JP2009-060799 (Kao) Neumann et al Biol Chem (1986) 367; 723-729 | NBRC15652 | |
| *Zymomonas mobilis* (WT ZmoSHC) | WO2010139719 | ATCC31821 | SEQ ID No. 1 |
| | US20120135477 | PF62207_2 Genpept Accession No AAV90172 | SEQ ID No. 2 |
| | Reipen et al (1995) Microbiology 141: 155-161 | EMBL/Genbank Accession No. for X80766 | |
| *Bradyrhizobium japonicum* (WT BjpSHC) | WO2010139719 US2012/0135477 | PF62207_5 | SEQ ID No. 5 |
| *Burkholderia ambifaria* | WO2010139719 US2012/0135477 | | SEQ ID No. 6 |
| *Burkholderia ambifaria* | WO2010139719 US2012/0135477 | | SEQ ID No. 7 |
| *Bacillus anthracis* | WO2010139719 US2012/0135477 | | SEQ ID No. 8 |
| *Frankia alni* | WO2010139719 US2012/0135477 | | SEQ ID No. 9 |
| *Rhodopseudomonas palustris* | WO2010139719 US2012/0135477 | | SEQ ID No. 10 |

The sequences of the wild-type AacSHC, wild-type ZmoSHC1, wild-type ZmoSHC2, wild-type BjpSHC, wild-type GmoSHC, wild-type TelSHC and wild-type ApaSHC1 are also disclosed herein (SEQ ID NO: 1, SEQ ID NO: 11, SEQ ID NO: 12, SEQ ID NO: 13. SEQ ID NO: 14, SEQ ID NO: 19 and SEQ ID NO: 20 respectively).

Figure 3:
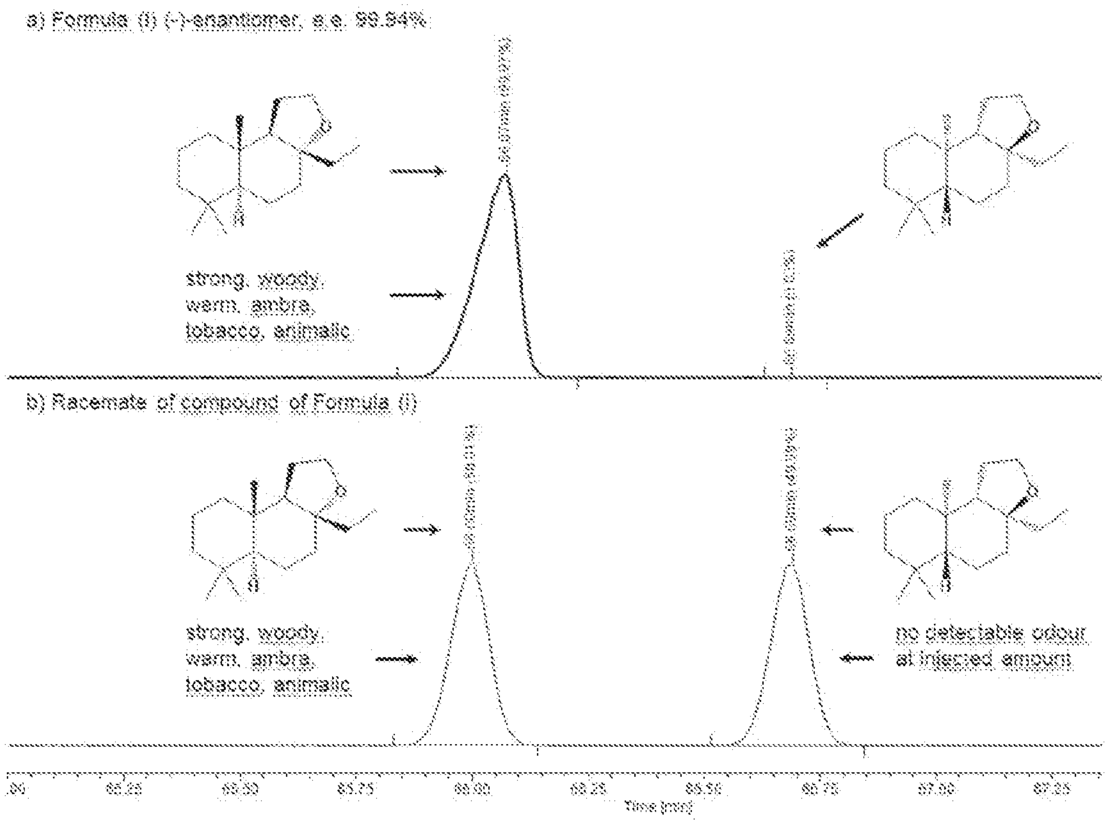
FIG. 3 shows the enantiopurity of the product of Formula (I) by chiral GC-analysis and its stronger odour compared to the other enantiomer.

An alignment of WT SHC sequences prepared by Hoshino and Sato (2002 as cited above) indicates that multiple motifs were detected in all four sequences and consists of the core sequence Gln-X-X-X-Gly-X-Trp which is found six times in the SHC sequences of both *Z. mobilis* and *A. acidocaldarius* (See FIG. 3 of Reipen et al 1995, Microbiology 141, 155-161). Hoshino and Sato (2002 as cited above) report that aromatic amino acids are unusually abundant in SHCs and that two characteristic motifs were noted in the SHCs: one is a QW motif represented by specific amino acid motifs [(K/R)(G/A)X2-3(F/Y/W)(1/IV) 3X3QX2-5GXW] and the alternative is a DXDDTA motif. Wendt et al (1997, Science 277, 1811-1815 and 1999, J Mol Biol 286, 175-187) reported on the X-ray structure analysis of *A. acidocaldarius* SHC. The DXDDTA motif appears to correlate with the SHC active site.

Functional homologues of the wild-type SHC enzymes or the SHC enzyme variants described herein are also suitable for use in cyclization reactions, for example for producing a compound of formula (II), for example in a recombinant host. Thus, the recombinant host may include one or more heterologous nucleic acid(s) encoding functional homologs of the polypeptides described above and/or a heterologous nucleic acid encoding a SHC variant enzyme as described herein.

A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild-type coding sequence, may themselves be functional homologs. Functional homologs can also be created via site-directed mutagenesis of the coding sequence for a polypeptide, or by combining domains from the coding sequences for different naturally-occurring polypeptides ("domain swapping"). Techniques for modifying genes encoding functional homologs described herein are known and include, inter alia, directed evolution techniques, site-directed mutagenesis techniques and random mutagenesis techniques, and can be useful to increase specific activity of a polypeptide, alter substrate specificity, alter expression levels, alter subcellular location, or modify polypeptide: polypeptide interactions in a desired manner. Such modified polypeptides are considered functional homologs. The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of the nucleic acid sequences encoding the SHC derivative polypeptides and the like.

Hybridization can also be used to identify functional homologs and/or as a measure of homology between two nucleic acid sequences. A nucleic acid sequence encoding any of the proteins disclosed herein, or a portion thereof, can be used as a hybridization probe according to standard hybridization techniques. The hybridization of a probe to DNA or RNA from a test source (e.g. a mammalian cell) is an indication of the presence of the relevant DNA or RNA in the test source. Hybridization conditions are known to those skilled in the art and can be found in Current Protocols in Molecular Biology, John Wiley & Sons, New York, 6.3.1-6.3.6, 1991. Moderate hybridization conditions are defined as equivalent to hybridization in 2×sodium chloride/sodium citrate (SSC) at 30° C. followed by a wash in 1×SSC, 0.1% SDS at 50° C. Highly stringent conditions are defined as equivalent to hybridization in 6× sodium chloride/sodium citrate (SSC) at 45° C. followed by a wash in 0.2×SSC, 0.1% SDS at 65° C. Sequence analysis to identify functional homologs can also involve BLAST, Reciprocal BLAST, or PSI-BLAST analysis of non-redundant databases using a relevant amino acid sequence as the reference sequence. Amino acid sequence is, in some instances, deduced from the nucleotide sequence. Those polypeptides in the database that have greater than 40% sequence identity are candidates for further evaluation for suitability for use in the SHC cyclization reaction. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have for e.g. conserved functional domains.

Typically, polypeptides that exhibit at least about 30% amino acid sequence identity are useful to identify conserved regions. Conserved regions of related polypeptides exhibit at least 30%, 40%, 41%, 42%, 43%, 44%, 45%, 46%, 47%, 48%, 49%, 50%, 51%, 52%, 53%, 54%, 55%, 56%, 57%, 58%, 59%, 60%, 81%, 62%, 63%, 64%, 65%, 86%, 67%, 68%, 69%, amino acid sequence identity. In some embodiments, a conserved region exhibits at least, 70%, 71%, 72%, 73%, 74%, 75%, 76%, 77%, 78%, 79%, 80%, at least 81%, at least 82%, at least 83%, at least 84%, at least 85%, at least 88%, at least 87%, at least 88%, at least 89%, at least 90%, at least 91%, at least 92%, at least 93%, at least 94%, at least 95%, at least 96%, at least 97%, at least 98%, or at least 99% amino acid sequence identity. Sequence identity can be determined as set forth above and below.

The SHC enzymes or enzyme variants described herein and used in the methods described herein may, for example, be based on an amino add sequence of SEQ ID NO: 1, SEQ ID NO: 10, SEQ ID NO: 11, SEQ ID NO: 12, SEQ ID NO: 13, SEQ ID NO: 14. SEQ ID NO: 19, SEQ ID NO: 20 or a variant, homologue, mutant, derivative or fragment thereof. The SHC enzyme or enzyme variant may, for example, have an amino acid sequence with at least 30%, 40%, 41%, 42%, 43%, 44%, 45%, 46%, 47%, 48%, 49%, 50%, 51%, 52%, 53%, 54%, 55%, 56%, 57%, 58%, 59%, β0%, 131%, 62%, 63%, 64%, 65%, 66%, 67%, 68%, 69%, 70%, 71%, 72%, 73%, 74%, 75%, 76%, 77%, 78%, 79%, 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity to SEQ ID NO: 1, SEQ ID NO: 10, SEQ ID NO: 11, SEQ ID NO: 12. SEQ ID NO: 13, SEQ ID NO: 14 or SEQ ID NO: 19 or SEQ ID NO: 20.

The SHC enzymes or enzyme variants described herein and used in the methods described herein may, for example, have a selectivity equal to or greater than about 75%. For example, the SHC enzyme or enzyme variant may have a selectivity equal to or greater than about 80% or equal to or greater than about 85% or equal to or greater than about 90% or equal to or greater than about 95%. For example, the SHC enzyme or enzyme variant may have a selectivity up to 100%, for example less than 100%, for example equal to or less than about 99.5% or equal to or less than about 99.0% or equal to or less than about 98.0% or equal to or less than about 97.0%.

"Percent (%) identity" with respect to the nucleotide sequence of a gene is defined as the percentage of nucleotides in a candidate DNA sequence that is identical with the nucleotides in the DNA sequence, after aligning the sequence and introducing gaps, if necessary, to achieve the maximum percent sequence identity, and not considering any conservative substitutions as part of the sequence identity. Alignment for purposes of determining percent nucleotide sequence identity can be achieved in various ways that are within the skill in the art, for instance, using publicly available computer software. Those skilled in the art can determine appropriate parameters for measuring alignment, including any algorithms needed to achieve maximal alignment over the full length of the sequences being compared. The terms "polypeptide" and "protein" are used interchangeably herein and mean any peptide-linked chain of amino acids, regardless of length or post-translational modification.

As used herein the term "derivative" includes but is not limited to a variant. The terms "derivative" and "variant" are used interchangeably herein.

In certain embodiments, the SHC enzyme variants described herein only include substitutions and do not include any deletions or insertions.

Specific SHC enzymes and enzymes variants that may be used in the methods described herein are further described below.

Wild-Type (WT) SHC Enzymes

The methods described herein may, for example, use an SHC enzyme having 100% sequence identity to a wild-type SHC enzyme. The wild-type SHC enzyme does not have to have been obtained directly from its natural organism and may have been produced heterologously in a host organism.

The wild-type SHC enzyme may, for example, be an SHC found in *Alicyclobacillus acidocaldarius* (Aac), *Zymomonas mobilis* (Zmo), *Bradyrhizobium japonicum* (Bjp or Bja), *Gluconobacter morbifer* (Gmo), *Burkholderia ambifaria, Bacillus anthracis, Methylococcus capsulatus, Frankia alni, Acetobacter pasteurianus* (Ape), *Thermosynechococcus elongates* (Tel). *Streptomyces coelicolor* (Sco), *Rhodopseudomonas palustris* (Rpa), *Teredinibacter tumerae* (Ttu), *Pelobacter carbinolicus* (Pca), or *Tetrahymena pyriformis* (see, for example WO 2010/139719, US 2012/01345477, WO 2012/066059, the contents of which are incorporated herein by reference).

In particular, the wild-type SHC enzyme may be the *Alicyclobacillus acidocaldarius* (Aac) SHC enzyme, the *Zymomonas mobilis* (Zmo) SHC enzyme, the *Bradyrhizobium japonicum* (Bjp/Bja) SHC enzyme or the *Gluconobacter morbifer* (Gmo) SHC enzyme. In particular, the wild-type SHC may be the *Alicyclobacillus acidocaldarius* (Aac) SHC enzyme.

For ease of reference, the designation "AacSHC" may be used to refer to the *Alicyclobacillus acidocaldarius* (Aac) SHC enzyme. "ZmoSHC" may be used to refer to the *Zymomonas mobilis* (Zmo) SHC enzyme, "BjpSHC" or "BjaSHC" may be used to refer to the *Bradyrhizobium japonicum* (Bjp) SHC enzyme, "GmoSHC" may be used to refer to the *Gluconobacter morbifer* (Gmo) SHC enzyme. "TelSHC" may be used to refer to the *Thermosynechococcus elongates* SHC enzyme and "ApaSHC" may be used to refer to the *Acetobacter pasteurianus* SHC enzyme.

The wild-type SHC enzyme amino add sequence may, for example, be AacSHC (SEQ ID NO: 1). ZmoSHC1 (SEQ ID NO: 11), ZmoSHC2 (SEQ ID NO: 12), BjpSHC (SEQ ID NO: 13), GmoSHC (SE) ID NO: 14), TelSHC (SEQ ID NO: 19) or ApaSHC1 (SEQ ID NO. 20). For example, the wild-type SHC enzyme may be AacSHC (SEQ ID NO: 1).

SHC Variant Enzyme

The methods described herein may, for example, use an SHC enzyme variant (i.e. an SHC enzyme having less than 100% sequence identity to a wild-type SHC enzyme).

The methods described herein may, for example, use a SHC enzyme variant as described in WO 2016/170099 or WO 2018/157021, the contents of which are incorporated herein by reference. For example, the SHC enzyme variant used in the methods described herein may be the SHC enzyme variant 215G2, which is described in WO 2016/170099.

The SHC enzyme variant may, for example, have an amino acid sequence having at least about 70.0% identity to a wild-type SHC enzyme amino acid sequence. For example, the SHC enzyme variant may have an amino acid sequence having at least about 75.0% or at least about 80.0% or at least about 85.0% or at least about 90.0% or at least about 95.0% or at least about 95.5% or at least about 96.5% or at least about 97.0% or at least about 97.5% or at least about 98.0% or at least about 98.5% or at least about 99.0% identity to a wild-type SHC enzyme amino acid sequence.

The SHC enzyme variant has an amino acid sequence having less than 100% identity, for example equal to or less than about 99.5% or equal to or less than about 99.0% identity to a wild-type SHC enzyme amino acid sequence.

For example, the SHC enzyme variant may have from about 70.0% to about 99.5% or from about 80.0% to about 99.0% or from about 85.0% to about 98.5% or from about 90.0% to about 98.0% identity to a wild-type SHC enzyme amino acid sequence.

The wild-type SHC enzyme may, for example, be from *Alicyclobacillus acidocaldarius* (Aac), *Zymomonas mobilis* (Zmo), *Bradyrhizobium japonicum* (Bjp), *Gluconobacter morbifer* (Gmo), *Burkholderia ambifaria, Bacillus anthraces, Methylococcus capsulatus, Frankia alni, Acetobacter pasteurianus* (Apa), *Thermosynechococcus elongatus* (Tel), *Streptomyces coelicolor* (Sco), *Rhodopseudomonas palustris* (Rpa), *Teredinibacter tumerae* (Ttu), *Pelobacter carbinolicus* (Pca), or *Tetrahymena pyriformis* (see, for example WO 2010/139719, US 2012/01345477, WO 2012/066059, the contents of which are incorporated herein by reference).

The wild-type SHC enzyme amino add sequence may, for example, be AacSHC (SEQ ID NO: 1), ZmoSHC1 (SEQ ID NO: 11), ZmoSHC2 (SEQ ID NO: 12), BjpSHC (SEQ ID NO: 13), GmoSHC (SEQ ID NO: 14), TelSHC (SEQ ID NO: 19) or ApaSHC1 (SEQ ID NO: 20). For example, the wild-type SHC enzyme may be AacSHC (SEQ ID NO: 1).

Therefore, in certain embodiments, the SHC enzyme or SHC enzyme variant may have an amino acid sequence having at least about 70.0% identity to SEQ ID NO: 1. SEQ ID NO: 11, SEQ ID NO: 12, SEQ ID NO: 13, SEQ ID NO: 14, SEQ ID NO: 19 or SEQ ID NO: 20. For example, the SHC enzyme or SHC enzyme variant has an amino acid sequence having at least about 75.0% or at least about 80.0% or at least about 85.0% or at least about 90.0% or at least about 95.0% or at least about 95.5% or at least about 96.5% or at least about 97.0% or at least about 97.5% or at least about 98.0% or at least about 98.5% or at least about 99.0% identity to SEQ ID NO: 1, SEQ ID NO: 11, SEQ ID NO: 12, SEQ ID NO: 13, SEQ ID NO: 14, SEQ ID NO: 19 or SEQ ID NO: 20.

For example, the SHC enzyme variant may, for example, have an amino acid sequence having less than 100% identity, for example equal to or less than about 99.5% or equal to or less than about 99.0% identity to SEQ ID NO: 1, SEQ ID NO: 11, SEQ ID NO: 12, SEQ ID NO: 13 SEQ ID NO: 14, SEQ ID NO: 19 or SEQ ID NO: 20.

For example, the SHC enzyme variant may have from about 70.0% to about 99.5% or from about 80.0% to about 99.0% or from about 85.0% to about 98.5% or from about 90.0% to about 98.0% identity to SEQ ID NO: 1, SEQ ID NO: 11, SEQ ID NO. 12, SEQ ID NO: 13 SEQ ID NO: 14, SEQ ID NO: 19 or SEQ ID NO: 20 “Percent (%) identity” with respect to a polypeptide or nucleotide sequence is defined respectively as the percentage of amino acids or nucleotides in a candidate sequence that are identical with the amino acids or nucleotides in the reference sequence, after aligning the sequence and introducing gaps, if necessary, to achieve the maximum percent sequence identity, and not considering any conservative substitutions as part of the sequence identity. Alignment for purposes of determining percent sequence identity can be achieved in various ways that are within the skill in the art, for instance, using publicly available computer software. Those skilled in the art can determine appropriate parameters for measuring alignment, including any algorithms needed to achieve maximal alignment over the full length of the sequences being compared. The terms “polypeptide” and “protein” are used interchangeably herein and mean any peptide-linked chain of amino acids, regardless of length or post-translational modification.

The similarity of nucleotide and amino acid sequences, i.e. the percentage of sequence identity, can be determined via sequence alignments. Such alignments can be carried out with several art-known algorithms, preferably with the mathematical algorithm of Karlin and Altschul (Karlin & Altschul (1993) Proc. Natl. Acad. Sci. USA 90: 5873-5877), with hmmalign (HMMER package, http.//hmmer.wustl.edu/) or with the CLUSTAL algorithm (Thompson, J. D., Higgins, D. G. & Gibson, T. J. (1994) Nucleic Acids Res. 22, 4673-80) available eg, on https://www.ebi.ac.uk/Tools/msa/clustalo/ or the GAP program (mathematical algorithm of the University of Iowa) or the mathematical algorithm of Myers and Miller (1989—Cabios 4: 11-17). Preferred parameters used are the default parameters as they are set on https://www.ebi.ac.uk/Tools/msa/clustalo/.

Percentage sequence identity may be calculated using, for example, BLAST. BLAT or BlastZ (or BlastX). A similar algorithm is incorporated into the BLASTN and BLASTP programs of Altschul et al (1990) J. Mol. Biol. 215, 403-410 BLAST polynucleotide searches may be performed with the BLASTN program, score=100, word length=12, to obtain polynucleotide sequences that are homologous to those nucleic acids which encode the relevant protein. BLAST protein searches may be performed with the BLASTP program, score=50, word length=3, to obtain amino acid sequences homologous to the polypeptide.

To obtain gapped alignments for comparative purposes, Gapped BLAST may be utilized as described in Altschul et al (1997) Nucleic Acids Res. 25, 3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1: 154-162) or Markov random fields. When percentages of sequence identity are referred to in the present application, these percentages are calculated in relation to the full length of the longer sequence, if not specifically indicated otherwise.

In particular embodiments, % identity between two sequences is determined using CLUSTAL O (version 1.2.4).

In certain embodiments, the SHC enzyme variant may have equal to or less than about 200 amino acid alterations compared to the wild-type SHC enzyme, for example compared to SEQ ID NO: 1, SEQ ID NO: 11, SEQ ID NO: 12, SEQ ID NO: 13, SEQ ID NO: 14, SEQ ID NO: 19 or SEQ ID NO: 20. For example, the SHC enzyme variant may have equal to or less than about 150 or equal to or less than about 120 or equal to or less than about 100 or equal to or less than about 95 or equal to or less than about 90 or equal to or less than about 85 or equal to or less than about 80 or equal to or less than about 75 or equal to or less than about 70 or equal to or less than about 65 or equal to or less than about 60 or equal to or less than about 55 or equal to or less than about 50 or equal to or less than about 45 or equal to or less than about 40 or equal to or less than about 35 or equal to or less than about 30 or equal to or less than about 25 or equal to or less than about 20 or equal to or less than about 15 or equal to or less than about 10 amino acid alterations compared to the wild-type SHC enzyme, for example compared to SEQ ID NO: 1, SEQ ID NO: 11, SEQ ID NO: 12, SEQ ID NO: 13, SEQ ID NO: 14, SEQ ID NO: 19 or SEQ ID NO: 20.

The SHC enzyme variant may, for example, have at least about 1 or at least about 2 or at least about 3 or at least about 4 or at least about 5 or at least about 6 amino acid alterations compared to the wild-type SHC enzyme, for example compared to SEQ ID NO: 1, SEQ ID NO: 11, SEQ ID NO: 12, SEQ ID NO: 13. SEQ ID NO: 14, SEQ ID NO: 19 or SEQ ID NO. 20

For example, the SHC enzyme variant may have from about 1 to about 30 amino acid alterations compared to the wild-type SHC enzyme, for example compared to SEQ ID NO: 1, SEQ ID NO. 11, SEQ ID NO: 12, SEQ ID NO: 13, SEQ ID NO: 14, SEQ ID NO: 19 or SEQ ID NO: 20. For example, the SHC enzyme variant may have from about 2 to about 25 amino acid alterations compared to the wild-type SHC enzyme, for example compared to SEQ ID NO: 1, SEQ ID NO: 11, SEQ ID NO: 12, SEQ ID NO: 1, SEQ ID NO: 14, SEQ ID NO: 19 or SEQ ID NO: 20. For example, the SHC enzyme variant may have from about 3 to about 20 amino acid alterations compared to the wild-type SHC enzyme, for example compared to SEQ ID NO: 1, SEQ ID NO: 11, SEQ ID NO: 12, SEQ ID NO: 1. SEQ ID NO: 14. SEQ ID NO: 19 or SEQ ID NO: 20. For example, the SHC enzyme variant may have from about 4 to about 15 amino acid alterations compared to the wild-type SHC enzyme, for example compared to SEQ ID NO: 1, SEQ ID NO: 11, SEQ ID NO: 12, SEQ ID NO: 13, SEQ ID NO: 14, SEQ ID NO: 19 or SEQ ID NO: 20. For example, the SHC enzyme variant may have from about 5 to about 10 amino acid alterations compared to the wild-type SHC enzyme, for example compared to SEQ ID NO: 1, SEQ ID NO: 11, SEQ ID NO: 12, SEQ ID NO: 13, SEQ ID NO: 14, SEQ ID NO: 19 or SEQ ID NO: 20.

The amino acid alterations may, for example, be insertions, deletions and/or substitutions as described above. For example, the amino acid alterations may be substitutions, for example, non-conservative substitutions.

In certain embodiments, the only amino acid alterations compared to the wild-type SHC enzyme (e.g. compared to SEQ ID NO: 1, SEQ ID NO: 11, SEQ ID NO: 12, SEQ ID NO: 13. SEQ ID NO: 14, SEQ ID NO: 19 or SEQ ID NO: 20) are substitutions (i.e. there are no insertions or deletions).

Amino acid alterations are defined relative to a reference sequence. An amino acid alteration relative to a reference sequence means that the amino acid sequence of the variant sequence is different to the reference sequence.

Amino acids in the reference sequence and the variant sequence may be assigned a number, where the numbering starts with the amino acid at the N-terminus of the polypeptide (i.e. the amino acid at the N-terminus of the polypeptide is numbered 1, the next amino acid is numbered 2 etc.). The “position” of a reference sequence refers to a specific amino acid residue present in the reference sequence as identified by the specific numbering of the amino acids in the reference sequence. The "position" of a variant sequence refers to a specific amino acid residue present in the variant sequence as identified by the specific numbering of the amino acids in the variant sequence.

Since the variant sequence may include deletions or insertions compared to the reference sequence, the amino acids in the variant sequence may be numbered differently to the same amino acids in the reference sequence. By way of example, if an amino acid is inserted between amino acids 131 and 132 of SEQ ID NO: 1, the amino acid following the insertion will have the numbering 133 in the variant sequence while it retains the numbering 132 in the reference sequence. In this example, the position of the variant sequence that corresponds to position 132 of the reference sequence is position 133. Therefore, amino acids in the variant sequence that have been retained from the reference sequence may be defined by referring to the "corresponding position" of the reference sequence. In other words, a "position" in the variant sequence may be defined by reference to a "corresponding position" in the reference sequence. In particular, substitutions in the variant sequence compared to the reference sequence may be defined by referring to the "corresponding position" of the reference sequence in spite of any insertions and/or deletions in the reference sequence. Where the amino acids of a reference sequence have been deleted, there is no "corresponding position" in the variant sequence. Where there are no insertions or deletions compared to the reference sequence (i.e. there are only substitutions), the "corresponding position" of the reference sequence will be the same as the position in the variant sequence.

Wild-type SHC enzymes from different species have different polypeptide lengths. The wild-type sequences may be aligned using algorithms as described above in order to identify "corresponding positions" in two different wild-type SHC enzymes. Therefore, the amino acid at a position of the variant sequence corresponding to a position in a reference sequence may, for example, be a different amino acid residue and/or may have a different number to that of the reference sequence. By way of example, the amino acid M at position 132 of AacSHC (SEQ ID NO: 1) may correspond to the amino acid Y at position 185 of ZmoSHC1 (SEQ ID NO: 11).

The amino acid alteration may therefore be defined relative to two different reference sequences. For example, the amino acid alteration may be a change compared to a first reference sequence (e.g. a wild-type SHC enzyme sequence from which the variant is derived) and the position of the amino acid alteration in the variant sequence may be defined by reference to a second reference sequence (e.g. the AacSHC (SEQ ID NO: 1)). Thus, the amino acid alteration in the SHC enzyme variant may be relative to a first wild-type SHC enzyme at a position defined by reference to a second wild-type SHC enzyme.

The SHC enzyme variant may have one or more of the specific substitutions, or combinations of substitutions, at one or more positions corresponding to positions 81, 90, 132, 172, 224, 277, 431, 432, 557 and 613 of SEQ ID NO: 1.

In particular, the SHC enzyme variant may have one or more of the following combinations of substitutions:

(i) substitutions at positions corresponding to positions 132, 224 and 432 of SEQ ID NO: 1;
(ii) substitutions at positions corresponding to positions 132, 224, 432, 557 and 431 of SEQ ID NO: 1;
(iii) substitutions at positions corresponding to positions 132, 224, 432, 557 and 613 of SEQ ID NO: 1;
(iv) substitutions at positions corresponding to positions 132, 224, 432, 557, 81 and 613 of SEQ ID NO: 1;
(v) substitutions at positions corresponding to positions 132, 224, 432, 557, 81 and 431 of SEQ ID NO: 1;
(vi) substitutions at positions corresponding to positions 132, 224, 432, 90 and 613 of SEQ ID NO: 1;
(vii) substitutions at positions corresponding to positions 132, 224, 432, 172 and 277 of SEQ ID NO: 1.

The SHC enzyme variant amino acid sequence may have one or more amino acid alterations relative to the wild-type SHC enzyme amino acid sequence at a position selected from positions corresponding to positions 81, 90, 172, 277, 431, 557 and 613 of SEQ ID NO: 1. For example, the amino acid alterations may be at one or more positions selected from positions corresponding to positions 81, 431, 557 and 613 of SEQ ID NO: 1. The amino acid alterations may, for example, be substitutions, for example non-conservative substitutions. The wild-type SHC enzyme amino acid sequence may, for example, be SEQ ID NO: 1, SEQ ID NO: 11, SEQ ID NO: 12, SEQ ID NO: 13, SEQ ID NO: 14, SEQ ID NO: 19 or SEQ ID NO: 20. For example, the wild-type sequence may be SEQ ID NO: 1.

In certain embodiments, the SHC enzyme variant amino acid sequence has an amino acid alteration relative to the wild-type SHC enzyme amino acid sequence at a position corresponding to position 557 of SEQ ID NO: 1 and at least one position corresponding to position 81, 431 or 613 of SEQ ID NO: 1. The amino acid alterations may, for example, be substitutions, for example non-conservative substitutions. The wild-type SHC enzyme amino acid sequence may, for example, be SEQ ID NO: 1, SEQ ID NO: 11, SEQ ID NO: 12, SEQ ID NO: 13, SEQ ID NO: 14, SEQ ID NO: 19 or SEQ ID NO: 20 For example, the wild-type sequence may be SEQ ID NO: 1.

For example, the SHC enzyme variant amino acid sequence may have an amino acid alteration relative to a wild-type SHC enzyme amino acid sequence at a position corresponding to position 557 of SEQ ID NO: 1 and one position corresponding to position 81, 431 or 613 of SEQ ID NO: 1. The amino acid alterations may, for example, be substitutions, for example non-conservative substitutions. The wild-type SHC enzyme amino acid sequence may, for example, be SEQ ID NO: 1, SEQ ID NO: 11, SEQ ID NO: 12, SEQ ID NO: 13, SEQ ID NO: 14, SEQ ID NO: 19 or SEQ ID NO: 20. For example, the wild-type sequence may be SEQ ID NO: 1.

For example, the SHC enzyme variant amino acid sequence may have amino acid alterations relative to a wild-type SHC enzyme amino acid sequence at a position corresponding to position 557 of SEQ ID NO: 1 and two positions selected from positions corresponding to positions 81, 431 and 613 of SEQ ID NO: 1. The amino acid alterations may, for example, be substitutions, for example non-conservative substitutions. The wild-type SHC enzyme amino acid sequence may, for example, be SEQ ID NO: 1, SEQ ID NO: 11, SEQ ID NO: 12, SEQ ID NO: 13, SEQ ID NO: 14, SEQ ID NO: 19 or SEQ ID NO: 20. For example, the wild-type sequence may be SEQ ID NO: 1.

For example, the SHC enzyme variant amino acid sequence may have amino acid alterations relative to a wild-type SHC enzyme amino acid sequence at a position corresponding to position 557 of SEQ ID NO: 1 and all positions corresponding to positions 81, 431 and 613 of SEQ ID NO: 1. The amino acid alterations may, for example, be substitutions, for example non-conservative substitutions.

The wild-type SHC enzyme amino acid sequence may, for example, be SEQ ID NO: 1, SEQ ID NO: 11, SEQ ID NO: 12, SEQ ID NO: 13. SEQ ID NO: 14, SEQ ID NO: 19 or SEQ ID NO: 20. For example, the wild-type sequence may be SEQ ID NO: 1.

For example, the SHC enzyme variant amino acid sequence has amino acid alterations relative to the wild-type SHC enzyme amino acid sequence at positions corresponding to positions 90 and 613 of SEQ ID NO: 1. The amino acid alterations may, for example, be substitutions, for example non-conservative substitutions. The wild-type SHC enzyme amino acid sequence may, for example, be SEQ ID NO: 1. SEQ ID NO: 11, SEQ ID NO: 12, SEQ ID NO: 13, SEQ ID NO: 14, SEQ ID NO: 19 or SEQ ID NO: 20. For example, the wild-type sequence may be SEQ ID NO: 1

For example, the SHC enzyme variant amino acid sequence has amino acid alterations relative to the wild-type SHC enzyme amino acid sequence at positions corresponding to positions 172 and 277 of SEQ ID NO: 1. The amino acid alterations may, for example, be substitutions, for example non-conservative substitutions. The wild-type SHC enzyme amino acid sequence may, for example, be SEQ ID NO: 1, SEQ ID NO: 11, SEQ ID NO: 12. SEQ ID NO: 13, SEQ ID NO: 14, SEQ ID NO: 19 or SEQ ID NO: 20. For example, the wild-type sequence may be SEQ ID NO: 1.

For example, the SHC enzyme variant amino acid sequence has amino acid alterations relative to the wild-type SHC enzyme amino acid sequence at positions corresponding to positions 557 and 431 of SEQ ID NO: 1. The amino acid alterations may, for example, be substitutions, for example non-conservative substitutions. The wild-type SHC enzyme amino acid sequence may, for example, be SEQ ID NO: 1, SEQ ID NO: 11, SEQ ID NO: 12, SEQ ID NO: 13, SEQ ID NO: 14, SEQ ID NO: 19 or SEQ ID NO: 20. For example, the wild-type sequence may be SEQ ID NO: 1.

For example, the SHC enzyme variant amino acid sequence has amino acid alterations relative to the wild-type SHC enzyme amino acid sequence at positions corresponding to positions 557 and 613 of SEQ ID NO: 1. The amino acid alterations may, for example, be substitutions, for example non-conservative substitutions. The wild-type SHC enzyme amino acid sequence may, for example, be SEQ ID NO: 1, SEQ ID NO: 11, SEQ ID NO: 12, SEQ ID NO: 13, SEQ ID NO: 14, SEQ ID NO: 19 or SEQ ID NO: 20. For example, the wild-type sequence may be SEQ ID NO: 1.

For example, the SHC enzyme variant amino acid sequence has amino acid alterations relative to the wild-type SHC enzyme amino acid sequence at positions corresponding to positions 81, 557 and 613 of SEQ ID NO: 1. The amino acid alterations may, for example, be substitutions, for example non-conservative substitutions. The wild-type SHC enzyme amino acid sequence may, for example, be SEQ ID NO: 1, SEQ ID NO: 11, SEQ ID NO: 12, SEQ ID NO: 13, SEQ ID NO: 14, SEQ ID NO: 19 or SEQ ID NO: 20. For example, the wild-type sequence may be SEQ ID NO: 1.

For example, the SHC enzyme variant amino acid sequence has amino acid alterations relative to the wild-type SHC enzyme amino acid sequence at positions corresponding to positions 81, 431 and 557 of SEQ ID NO: 1. The amino acid alterations may, for example, be substitutions, for example non-conservative substitutions. The wild-type SHC enzyme amino acid sequence may, for example, be SEQ ID NO: 1, SEQ ID NO: 11, SEQ ID NO: 12, SEQ ID NO: 13, SEQ ID NO: 14, SEQ ID NO: 19 or SEQ ID NO: 20. For example, the wild-type sequence may be SEQ ID NO: 1.

The amino acid alteration relative to the wild-type SHC enzyme amino acid sequence at a position corresponding to position 557 of SEQ ID NO: 1 may, for example, be a substitution of the amino acid of the wild-type SHC enzyme for a different amino acid (X). As noted above, since the wild-type sequence may have a different length to SEQ ID NO: 1 and since the variant may additionally comprise insertions and/or deletions, the numbering of the new amino acid (X) in the variant sequence may not be 557.

The new amino acid (X) in the SHC enzyme variant amino acid sequence at a position corresponding to position 557 of SEQ ID NO: 1 may, for example, be Met. Val, Leu, Ile, Cys, Ser, Thr, Asn, Gln, Asp, Glu, His, Lys, Arg, Gly, Pro, Trp, Tyr or Phe. For example, the new amino acid (X) in the SHC enzyme variant may be a neutral hydrophilic amino acid (i.e. Cys, Ser, Thr, Asn or Gln). For example, the new amino acid in the SHC enzyme variant may be threonine.

The amino acid alteration relative to the wild-type SHC enzyme amino acid sequence at a position corresponding to position 81 of SEQ ID NO: 1 may, for example, be a substitution of the amino acid of the wild-type SHC enzyme for a different amino acid (X). As noted above, since the wild-type sequence may have a different length to SEQ ID NO: 1 and since the variant may additionally comprise insertions and/or deletions, the numbering of the new amino acid (X) may not be 81.

The new amino acid (X) in the SHC enzyme variant amino acid sequence at a position corresponding to position 81 of SEQ ID NO: 1 may, for example, be Met, Ala, Val, Leu, Ile, Cys, Ser, Thr, Asn, Gln, Asp, Glu, His, Lys, Arg, Gly, Pro, Trp, or Phe. For example, the new amino acid (X) in the SHC enzyme variant may be a basic amino acid (i.e. His, Lys or Arg). For example, the new amino acid in the SHC enzyme variant may be histidine.

The amino acid alteration relative to the wild-type SHC enzyme amino acid sequence at a position corresponding to position 90 of SEQ ID NO: 1 may, for example, be a substitution of the amino acid of the wild-type SHC enzyme for a different amino acid (X). As noted above, since the wild-type sequence may have a different length to SEQ ID NO: 1 and since the variant may additionally comprise insertions and/or deletions, the numbering of the new amino acid (X) in the variant sequence may not be 90.

The new amino acid (X) in the SHC enzyme variant amino acid sequence at a position corresponding to position 90 of SEQ ID NO: 1 may, for example, be Met, Ala, Val, Leu, Ile, Cys, Ser, Asn, Gin, Asp, Glu, His, Lys, Arg, Gly, Pro, Trp, Tyr or Phe. For example, the new amino acid (X) in the SHC enzyme variant may be a hydrophobic amino acid (i.e. Met, Ala, Val, Leu, Ile). Far example, the new amino acid in the SHC enzyme variant may be alanine.

The amino acid alteration relative to the wild-type SHC enzyme amino acid sequence at a position corresponding to position 172 of SEQ ID NO: 1 may, for example, be a substitution of the amino acid of the wild-type SHC enzyme for a different amino acid (X). As noted above, since the wild-type sequence may have a different length to SEQ ID NO: 1 and since the variant may additionally comprise insertions and/or deletions, the numbering of the new amino acid (X) in the variant sequence may not be 172.

The new amino acid (X) in the SHC enzyme variant amino acid sequence at a position corresponding to position 172 of SEQ ID NO: 1 may, for example, be Met, Val, Leu, Ile, Cys, Ser, Thr, Asn, Gin, Asp, Glu, His, Lys, Arg, Gly, Pro, Trp, Tyr or Phe. For example, the new amino acid (X) in the SHC enzyme variant may be a neutral hydrophilic amino acid (i.e. Cys, Ser, Thr, Asn, Gin). For example, the new amino acid in the SHC enzyme variant may be threonine.

The amino acid alteration relative to the wild-type SHC enzyme amino acid sequence at a position corresponding to position 277 of SEQ ID NO: 1 may, for example, be a substitution of the amino acid of the wild-type SHC enzyme for a different amino acid (X). As noted above, since the wild-type sequence may have a different length to SEQ ID NO: 1 and since the variant may additionally comprise insertions and/or deletions, the numbering of the new amino acid (X) in the variant sequence may not be 277.

The new amino acid (X) in the SHC enzyme variant amino acid sequence at a position corresponding to position 277 of SEQ ID NO: 1 may, for example, be Ala, Val, Leu, Ile, Cys, Ser, Thr, Asn. Gin, Asp. Glu, His, Lys. Arg, Gly, Pro, Trp, Tyr or Phe. For example, the new amino acid (X) in the SHC enzyme variant may be a basic amino acid (i.e. His, Lys, Arg). For example, the new amino acid in the SHC enzyme variant may be lysine.

The amino acid alteration relative to the wild-type SHC enzyme amino acid sequence at a position corresponding to position 431 of SEQ ID NO: 1 may, for example, be a substitution of the amino acid of the wild-type SHC enzyme for a different amino acid (X). As noted above, since the wild-type sequence may have a different length to SEQ ID NO: 1 and since the variant may additionally comprise insertions and/or deletions, the numbering of the new amino acid (X) may not be 431.

The new amino acid (X) in the SHC enzyme variant amino acid sequence at a position corresponding to position 431 of SEQ ID NO: 1 may, for example, be Met, Ala, Val, Leu, Ile, Cys, Ser, Thr, Asn, Gin, Asp, Glu, Lys, Arg, Gly, Pro, Trp, Tyr or Phe. For example, the new amino acid (X) in the SHC enzyme variant may be a hydrophobic amino acid (i.e. Met, Ala. Val, Leu or Ile). For example, the new amino acid in the SHC enzyme variant may be leucine.

The amino acid alteration relative to the wild-type SHC enzyme amino acid sequence at a position corresponding to position 613 of SEQ ID NO: 1 may, for example, be a substitution of the amino acid of the wild-type SHC enzyme for a different amino acid (X) As noted above, since the wild-type sequence may have a different length to SEQ ID NO: 1 and since the variant may additionally comprise insertions and/or deletions, the numbering of the new amino acid (X) may not be 613.

The new amino acid (X) in the SHC enzyme variant amino acid sequence at a position corresponding to position 613 of SEQ ID NO: 1 may, for example, be Met, Ala, Val. Leu, Ile, Cys, Ser. Thr, Asn, Gin, Asp, Glu, His, Lys, Gly. Pro, Trp, Tyr or Phe. For example, the new amino acid (X) in the SHC enzyme variant may be a neutral hydrophilic amino acid (i.e. Cys, Ser, Thr, Asn or Gln). For example, the new amino acid in the SHC enzyme variant may be threonine.

Figure 2:
FIG. 2 shows an amino acid sequence alignment using CLUSTAL O (1.2.4) between wild-type AacSHC (SEQ ID NO: 1) and wild-type TelSHC (SEQ ID NO: 19), wild-type ApaSHC1 (SEQ ID NO: 20), wild-type ZmoSHC1 (SEQ ID NO: 11), wild-type ZmoSHC2 (SEQ ID NO: 12), wild-type BjpSHC (SEQ ID NO: 13) and GmoSHC (SEQ ID NO: 14). Amino acid positions 81, 90, 132, 224, 172, 277, 431, 432, 557 and 613 in wild-type AacSHC are highlighted with a white letter on a black background.
Figure 2:

The amino acids and positions in the wild-type ZmoSHC1, ZmoSHC2, BjpSHC, GmoSHC, TelSHC and ApaSHC1 sequences (SEQ ID NOs: 11, 12, 13, 14, 19 and 20 respectively) that correspond to the amino acids of AacSHC (SEQ ID NO: 1) (e.g. the amino acids at positions 81, 431, 557 and 613 of AacSHC) are shown in FIG. 2.

Amino acid positions 81, 90, 132, 224, 172, 277, 431, 432, 557 and 613 in wild-type AacSHC are highlighted with a white letter on a black background. The amino acids directly above or below the highlighted amino acid are therefore the amino acids and positions in ZmoSHC2, BjaSHC, GmoSHC, ApaSHC1, ZmoSHC1 and TelSHC that correspond to positions 81, 90, 132, 224, 172, 277, 431, 432, 557 and 613 of AacSHC (SEQ ID NO: 1). For example, the amino acid in BjaSHC, GmoSHC, ApaSHC1 and ZmoSHC1 that corresponds to the amino acid Y a position 81 of AacSHC (SEQ ID NO. 1) is Y. The amino acid in ZmoSHC2 and TelSHC that corresponds to the amino acid Y at position 81 of AacSHC (SEQ ID NO: 1) is F. Position 84 of TelSHC is the position of TelSHC that corresponds to position 81 of AacSHC (SEQ ID NO: 1).

The SHC enzyme variant amino acid sequence may have one or more amino acid alterations relative to the wild-type SHC enzyme amino acid sequence at positions corresponding to positions 132, 224 and 432 of SEQ ID NO: 1. The amino acid alterations may, for example, be substitutions.

For example, the SHC enzyme variant amino acid sequence may have one, two, or three amino acid alterations relative to the wild-type SHC enzyme amino acid sequence at positions selected from positions corresponding to positions 132, 224 and 432 of SEQ ID NO: 1.

For example, the SHC enzyme variant amino acid sequence may have amino acid alterations relative to the wild-type SHC enzyme amino acid sequence at positions corresponding to positions 132 and 432 of SEQ ID NO: 1.

For example, the SHC enzyme variant amino acid sequence may have amino acid alterations relative to the wild-type SHC enzyme amino acid sequence at positions corresponding to positions 132, 224 and 432 of SEQ ID NO. 1.

For example, the SHC enzyme variant amino acid sequence may have amino acid alterations relative to the wild-type SHC enzyme amino acid sequence at positions corresponding to positions 90, 132, 224, 432 and 613 of SEQ ID NO. 1 For example, the SHC enzyme variant amino acid sequence may have amino acid alterations relative to the wild-type SHC enzyme amino acid sequence at positions corresponding to positions 132, 172, 224, 277 and 432 of SEQ ID NO: 1. For example, the SHC enzyme variant amino acid sequence may have amino acid alterations relative to the wild-type SHC enzyme amino acid sequence at positions corresponding to positions 132, 224, 432 and 557 of SEQ ID NO: 1 and one or more positions selected from positions corresponding to positions 81, 431 and 613 of SEQ ID NO: 1. For example, the SHC enzyme variant amino acid sequence may have amino acid alterations relative to the wild-type SHC enzyme amino acid sequence at positions corresponding to positions 132, 224, 431, 432 and 557 of SEQ ID NO: 1. For example, the SHC enzyme variant amino acid sequence may have amino acid alterations relative to the wild-type SHC enzyme amino acid sequence at positions corresponding to positions 132, 224, 432, 557 and 613 of SEQ ID NO: 1. For example, the SHC enzyme variant amino acid sequence may have amino acid alterations relative to the wild-type SHC enzyme amino acid sequence at positions corresponding to positions 81, 132, 224, 432, 557 and 613 of SEQ ID NO. 1. For example, the SHC enzyme variant amino acid sequence may have amino acid alterations relative to the wild-type SHC enzyme amino acid sequence at positions corresponding to positions 81, 132, 224, 431, 432 and 557 of SEQ ID NO: 1. The amino acid alterations may, for example, be substitutions, for example non-conservative substitutions. The wild-type SHC enzyme amino acid sequence may, for example, be SEQ ID NO: 1, SEQ ID NO: 11, SEQ ID NO: 12, SEQ ID NO: 13. SEQ ID NO: 14, SEQ ID NO: 19 or SEQ ID NO: 20. For example, the wild-type sequence may be SEQ ID NO: 1.

The amino acid alteration relative to the wild-type SHC enzyme amino acid sequence at a position corresponding to position 132 of SEQ ID NO: 1 may, for example, be a substitution of the amino acid of the wild-type SHC enzyme for a different amino acid (X). As noted above, since the wild-type sequence may have a different length to SEQ ID NO: 1 and since the variant may additionally comprise insertions and/or deletions, the numbering of the new amino acid (X) in the variant sequence may not be 132.

The new amino acid (X) in the SHC enzyme variant amino acid sequence at a position corresponding to position 132 of SEQ ID NO: 1 may, for example, be Ala, Val, Leu, Ile, Cys, Ser, Thr, Asti. Gin, Asp. Glu, His, Lys. Arg, Gly, Pro, Trp, Tyr or Phe. For example, the new amino acid (X) in the SHC enzyme variant may be a basic amino acid (i.e. His, Lys or Arg). For example, the new amino acid in the SHC enzyme variant may be arginine.

The amino acid alteration relative to the wild-type SHC enzyme amino acid sequence at a position corresponding to position 224 of SEQ ID NO: 1 may, for example, be a substitution of the amino acid of the wild-type SHC enzyme for a different amino acid (X). As noted above, since the wild-type sequence may have a different length to SEQ ID NO: 1 and since the variant may additionally comprise insertions and/or deletions, the numbering of the new amino acid (X) in the variant sequence may not be 224.

The new amino acid (X) in the SHC enzyme variant amino acid sequence at a position corresponding to position 224 of SEQ ID NO: 1 may, for example, be Met, Val, Leu, Ile, Cys, Ser, Thr, Asn, Gin, Asp, Glu, His, Lys, Arg, Gly, Pro, Trp, Tyr or Phe. For example, the new amino acid (X) in the SHC enzyme variant may be a hydrophobic amino acid (i.e. Met, Val, Leu or Ile). For example, the new amino acid in the SHC enzyme variant may be valine.

The amino acid alteration relative to the wild-type SHC enzyme amino acid sequence at a position corresponding to position 432 of SEQ ID NO: 1 may, for example, be a substitution of the amino acid of the wild-type SHC enzyme for a different amino acid (X). As noted above, since the wild-type sequence may have a different length to SEQ ID NO: 1 and since the variant may additionally comprise insertions and/or deletions, the numbering of the new amino acid (X) in the variant sequence may not be 432.

The new amino acid (X) in the SHC enzyme variant amino acid sequence at a position corresponding to position 432 of SEQ ID NO: 1 may, for example, be Met, Ala, Val, Leu, Cys, Ser. Thr, Asn, Gin. Asp, Glu, His, Lys, Arg, Gly, Pro, Trp, Tyr or Phe. For example, the new amino acid (X) in the SHC enzyme variant may be a neutral hydrophilic amino acid (i.e. Cys, Ser, Thr, Asn or Gln). For example, the new amino acid in the SHC enzyme variant may be threonine.

The amino acids and positions in the wild-type ZmoSHC1. ZmoSHC2, BjpSHC, GmoSHC, TelSHC and ApaSHC1 sequences (SEQ ID NOs: 11, 12, 13, 14, 19 and 20 respectively) that correspond to the amino acids of AacSHC (SEQ ID NO: 1) (e.g. at positions 132, 224 and 432 of AacSHC) are shown in FIG. 2.

The SHC enzyme variants described herein may, for example, have one or more other amino acid alterations (e.g. substitutions) at the other positions of AacSHC identified in WO 2016/170099.

Any combination of the amino acid alterations described herein is envisaged. In particular, combinations of amino acid alterations at positions corresponding to the combinations of amino acid alterations identified in AaCSHC herein and in WO 2016/17009 are envisaged.

In certain embodiments, the SHC enzyme variant is identical to SEQ ID NO: 1 except for the following amino acid substitutions:

(i) M132R, A224V, I432T, A557T and H431L (SEQ ID NO: 2); or (ii) M132R, A224V, 1432T, A557T and R613S (SEQ ID NO: 3); or (iii) M132R, A224V, I432T, A557T, Y81H and R613S (SEQ ID NO: 4); or (iv) M132R, A224V, I432T, A557T, Y81H and H431L (SEQ ID NO: 5); or (v) M132R, A224V, I432T, T90A and R613S (SEQ ID NO: 17); or (vi) M132R, A224V, 1432T. A172T and M277K (SEQ ID NO: 18).

The SHC enzyme variant may, for example, have the amino acid sequence of SEQ ID NO: 2, SEQ ID NO: 3. SEQ ID NO: 4, SEQ ID NO: 5, SEQ ID NO: 6. SEQ ID NO: 7, SEQ ID NO: 8, SEQ ID NO: 9, SEQ ID NO: 10, SEQ ID NO: 17, SEQ ID NO: 18, SEQ ID NO: 21, SEQ ID NO: 22, or SEQ ID NO: 23

The SHC enzyme variants may, for example, have increased enzymatic activity for the conversion of the compound of formula (II) to the compound of formula (I) compared to the wild-type SHC enzyme. Increased enzymatic activity may refer to any aspect of the enzymatic conversion of the compound of formula (II) to the compound of formula (I) including, for example, increased total conversion of the compound of formula (II) to the compound of formula (I), increased rate of conversion of the compound of formula (II) (e.g. in the first 6 hours or in the first 12 hours of reaction), increased production of the compound of formula (I), and decreased production of by-products. Increased enzymatic activity may be defined by increased productivity in general, which may be defined in terms of compound of formula (I) produced per hour, per gram of biocatalyst and per liter of reaction.

The SHC enzyme variants may, for example, provide increased conversion of compound of formula (II) compared to the wild-type SHC enzyme. Therefore, the process described herein may have an increased level of compound of formula (11) conversion compared to the process using the wild-type SHC enzyme. The SHC enzyme variants may, for example, provide increased rate of compound of formula (II) conversion compared to the wild-type SHC enzyme. Therefore, the process described herein may have an increased rate of compound of formula (II) conversion compared to the wild-type SHC enzyme. The SHC enzyme variant may, for example, provide increased rate of compound of formula (II) conversion over the first 4 hours or over the first 6 hours or over the first 8 hours or over the first 12 hours or over the first 24 hours of the reaction compared to the wild-type SHC enzyme. Therefore, the process described herein may have an increased rate of compound of formula (II) conversion over the first 4 hours or over the first 6 hours or over the first 8 hours or over the first 12 hours or over the first 24 hours of the reaction compared to the wild-type SHC enzyme. This may be when compared to using both enzymes (i.e. the SHC enzyme variant and the wild-type SHC enzyme) under the same reaction conditions (e.g. same pH and temperature) or when compared to using each enzymes under their optimized reaction conditions (e.g. optimized pH and temperature) which may be different to each other.

For example, the new SHC enzyme variant may provide or the process may have at least about 5% compound of formula (II) conversion in the first 24 hours of the reaction.

For example, the new SHC enzyme variant may provide or the process may have at least about 6% or at least about 8% or at least about 10% or at least about 12% or at least about 14% or at least about 15% compound of formula (II) conversion in the first 24 hours of the reaction. For example, the new SHC enzyme variant may provide or the process may have at least about 1.5% compound of formula (II) conversion in the first 4 hours of the reaction. For example, the new SHC enzyme variant may provide or the process may have at least about 2.0% or at least about 2.5% or at least about 3.0% or at least about 3.5% or at least about 4.0% or at least about 4.5% or at least about 5.0 compound of formula (II) conversion in the first 4 hours of the reaction. This may be when compared to using both enzymes (i.e. the new SHC enzyme variant and the enzyme of SEQ ID NO: 1 or SEQ ID NO: 10) under the same reaction conditions (e.g. same pH and temperature) or when compared to using each enzymes under their respective optimized reaction conditions (e.g. optimized pH and temperature) which may be different to each other.

The conversion of compound of formula (II) to compound of formula (I) may, for example, be determined using an activity assay as described above and may be calculated as gram of recoverable product per gram of feedstock (which can be calculated as a percent molar conversion rate).

The optimum temperature for the SHC enzyme variant may, for example, be equal to or greater than about 30° C. For example, the optimum temperature for the SHC enzyme variant may range from about 30° C. to about 50° C., for example from about 35° C. to about 50° C. or from about 40° C. to about 50° C. or from about 35° C. to about 45° C. For example, the optimum temperature of the SHC enzyme variant may be about 35° C. or about 45° C. The processes for making the compound of formula (I) disclosed herein may be carried out at the optimum temperature of the SHC enzyme variant.

The optimum pH for the SHC enzyme variant may, for example, be equal to or greater than about 5.0. For example, the optimum pH for the SHC enzyme variant may range from about 5.0 to about 6.0, for example from about 5.2 to about 5.8, for example from about 5.4 to about 5.8, for example from about 5.6 to about 5.8. For example, the optimum pH of the SHC enzyme variant may be about 5.4 or about 5.6 or about 5.8. The processes for making the compound of formula (I) disclosed herein may be carried out at the optimum pH of the SHC enzyme variant.

The optimum concentration of sodium dodecyl sulfate (SDS) in the reaction medium of the processes for making the compound of formula (I) disclosed herein may, for example, be from about 0.010 w/w % to about 0.10 w/w %. For example, the optimum concentration of SDS may be from about 0.040 w/w % to about 0.080 w/w %, for example about 0.050 w/w % when Ethyl-homofarnesol is used at 4 WI with cells to an $OD_{650\ nm}$ of 10.

The processes for making the compound of formula (I) disclosed herein may be carried out at the optimum temperature range or optimum temperature and/or the optimum pH range or optimum pH and/or the SOS optimum concentration range or optimum SDS concentration for the specific enzyme used, as set out in the Examples below.

Nucleic Acids and Methods of Making Nucleic Acids

The SHC enzyme and enzyme variants described herein may be encoded by a nucleic acid. The nucleic acid may, for example, be an isolated nucleic acid.

Thus, there is provided herein a construct comprising a nucleic acid sequence encoding a SHC enzyme or enzyme variant as described herein. As used herein, a "construct" is an artificially created segment of nucleic acid that is to be transfected into a target cell. The construct may comprise the nucleic acid encoding the SHC enzyme or enzyme variant and an expression controller (e.g. promoter).

There is further provided herein a vector comprising a construct as described herein. As used herein, a "vector" is a DNA molecule that is used as a vehicle to artificially carry foreign genetic material into a cell where it can be replicated and/or expressed. The vector may, for example, be a plasmid, a viral vector, a cosmid, or an artificial chromosome.

The terms "construct" and "vector" may overlap, for example where the construct is a plasmid.

In particular, there is provided herein a nucleic acid encoding an amino acid sequence of any one of SEQ ID NO: 2, SEQ ID NO: 3, SEQ ID NO: 4, SEQ ID NO: 5, SEQ ID NO: 17, SEQ ID NO: 18.

In particular, there is provided herein a nucleic acid having the sequence of SEQ ID NO: 6, SEQ ID NO: 7, SEQ ID NO: 8, SEQ ID NO: 9, SEQ ID NO: 22 and SEQ ID NO: 23 which may, for example, be comprised in a construct or a vector as described herein.

The term "nucleic acid" or "nucleic acid molecule" as used herein shall specifically refer to polynucleotides of the disclosure which can be DNA, cDNA, genomic DNA, synthetic DNA, or RNA, and can be double-stranded or single-stranded, the sense and/or an antisense strand. The term "nucleic acid" or "nucleic acid molecule" shall particularly apply to the polynucleotide(s) as used herein, e.g. as full-length nucleotide sequence or fragments or parts thereof, which encodes a polypeptide with enzymatic activity, e.g. an enzyme of a metabolic pathway, or fragments or parts thereof, respectively.

The term also includes a separate molecule such as a cDNA where the corresponding genomic DNA has introns and therefore a different sequence; a genomic fragment that lacks at least one of the flanking genes; a fragment of cDNA or genomic DNA produced by polymerase chain reaction (PCR) and that lacks at least one of the flanking genes; a restriction fragment that lacks at least one of the flanking genes; a DNA encoding a non-naturally occurring protein such as a fusion protein (e.g. a His tag), mutein, or fragment of a given protein; and a nucleic acid which is a degenerate variant of a cDNA or a naturally occurring nucleic acid. In addition, it includes a recombinant nucleotide sequence that is part of a hybrid gene, i.e. a gene encoding a non-naturally occurring fusion protein. Fusion proteins can add one or more amino acids (such as but not limited to Histidine (His)) to a protein, usually at the N-terminus of the protein but also at the C-terminus or fused within regions of the protein. Such fusion proteins or fusion vectors encoding such proteins typically serve three purposes: (i) to increase production of recombinant proteins; (ii) to increase the solubility of the recombinant protein; and (iii) to aid in the purification of the recombinant protein by providing a ligand for affinity purification.

The term "nucleic acid" or "nucleic acid molecule" also includes codon optimised sequences suitable for expression in a particular microbial host cell (e.g. *E. coli* host cell). As used herein, the term "codon optimized" means a nucleic acid protein coding sequence which has been adapted for expression in a prokaryotic or a eukaryotic host cell, particularly bacterial host cells such as *E. coli* host cells by substitution of one or more or preferably a significant number of colons with colons that are more frequently used in bacterial (e.g. *E. coli* host cell genes.

In this regard, the nucleotide sequence encoding the reference amino acid sequence (e.g. SEQ ID NO: 1 or SEQ ID NO: 10) and variants/derivatives thereof may be the original one as found in the source (e.g. SEQ ID NO: 1 found in AacSHC) or the gene can be colon-optimized for the selected host organisms, such as e.g. *E. coli.*

A ribonucleic acid (RNA) molecule can be produced by in vitro transcription. Segments of DNA molecules are also considered within the scope of the disclosure, and can be produced by, for example, the polymerase chain reaction (PCR) or generated by treatment with one or more restriction endonucleases. Segments of a nucleic acid molecule may be referred to as DNA fragments of a gene, in particular those that are partial genes. A fragment can also contain several open reading frames (ORF), either repeats of the same ORF or different ORF's. The term shall specifically refer to coding nucleotide sequences, but shall also include nucleotide sequences which are non-coding, e.g. untranscribed or untranslated sequences, or encoding polypeptides, in whole or in part. The genes as used herein, e.g. for assembly, diversification or recombination can be non-coding sequences or sequences encoding polypeptides or protein encoding sequences or parts or fragments thereof having sufficient sequence length for successful recombination events. More specifically, said genes have a minimum length of 3 bp, preferably at least 100 bp, more preferred at least 300 bp. It will be apparent from the foregoing that a reference to an isolated DNA does not mean a DNA present among hundreds to millions of other DNA molecules within, for example, cDNA or genomic DNA libraries or genomic DNA restriction digests in, for example, a restriction digest reaction mixture or an electrophoretic gel slice. An isolated nucleic acid molecule of the present disclosure encompasses segments that are not found as such in the natural state.

As used herein, the term "isolated DNA" can refer to (1) a DNA that contains sequence not identical to that of any naturally occurring sequence, a polynucleotide or nucleic acid which is not naturally occurring, (e.g. is made by the artificial combination (e.g. artificial manipulation of isolated segments of nucleic acids, e.g. by genetic engineering techniques) of two otherwise separated segments of sequences through human intervention) or (2), in the context of a DNA with a naturally-occurring sequence (e.g. a cDNA or genomic DNA), a DNA free of at least one of the genes that flank the gene containing the DNA of interest in the genome of the organism in which the gene containing the DNA of interest naturally occurs.

The term "isolated DNA" as used herein, specifically with respect to nucleic acid sequences may also refer to nucleic acids or polynucleotides produced by recombinant DNA techniques, e.g. a DNA construct comprising a polynucleotide heterologous to a host cell, which is optionally incorporated into the host cell. A chimeric nucleotide sequence may specifically be produced as a recombinant molecule. The term "recombination" shall specifically apply to assembly of polynucleotides, joining together such polynucleotides or parts thereof, with or without recombination to achieve a cross-over or a gene mosaic. For example, it is performed to join together nucleic acid segments of desired functions to generate a desired combination of functions. A recombinant gene encoding a polypeptide described herein may include the coding sequence for that polypeptide, operably linked, in sense orientation, to one or more regulatory regions suitable for expressing the polypeptide. Because many microorganisms are capable of expressing multiple gene products from a polycistronic mRNA, multiple polypeptides can be expressed under the control of a single regulatory region for those microorganisms, if desired. A coding sequence and a regulatory region are considered to be operably linked when the regulatory region and coding sequence are positioned so that the regulatory region is effective for regulating transcription or translation of the sequence.

The term "recombinant" as used herein, specifically with respect to enzymes shall refer to enzymes produced by recombinant DNA techniques, i.e. produced from cells transformed by an exogenous DNA construct encoding the desired enzyme. "Synthetic" enzymes are those prepared by chemical synthesis. A chimeric enzyme may specifically be produced as recombinant molecule. The term "recombinant DNA" therefore includes a recombinant DNA incorporated into a vector into an autonomously replicating plasmid or virus, or into the genomic DNA of a prokaryote or eukaryote (or the genome of a homologous cell, at a position other than the natural chromosomal location).

In a further aspect the nucleic acid molecule(s) of the present disclosure is/are operatively linked to expression control sequences allowing expression in prokaryotic and/or eukaryotic host cells. As used herein, "operatively linked" means incorporated into a genetic construct so that expression control sequences effectively control expression of a coding sequence of interest. The transcriptional/translational regulatory elements referred to above include but are not limited to inducible and non-inducible, constitutive, cell cycle regulated, metabolically regulated promoters, enhancers, operators, silencers, repressors and other elements that are known to those skilled in the art and that dove or otherwise regulate gene expression. Such regulatory elements include but are not limited to regulatory elements directing constitutive expression or which allow inducible expression like, for example, CUP-1 promoter, the tet repressor as employed, for example, in the tet-on or tet-off systems, the lac system, the trp system regulatory elements. By way of example, Isopropyl β-D-1-thiogalactopyranoside (IPTG) is an effective inducer of gene expression in the concentration range of 100 μM to 1.0 mM. This compound is a molecular mimic of allolactose, a lactose metabolite that triggers transcription of the lac operon, and it is therefore used to induce gene expression when the gene is under the control of the lac operator. Another example of a regulatory element which induces gene expression is lactose. Similarly, the nucleic acid molecule(s) of the present disclosure can form part of a hybrid gene encoding additional polypeptide sequences, for example, a sequence that functions as a marker or reporter. Examples of marker and reporter genes including beta-lactamase, chloramphenicol acetyltransferase (CAT), adenosine deaminase (ADA), aminoglycoside phosphotransferase dihydrofolate reductase (DHFR), hygromycin-B-phosphotransferase (MPH), thymidine kinase (TK), lacZ (encoding beta-galactosidase), and xanthine guanine phosphoribosyltransferase (XGPRT). As with many of the standard procedures associated with the practice of the disclosure, skilled artisans will be aware of additional useful reagents, for example, additional sequences that can serve the function of a marker or reporter.

There is also provided herein a recombinant polynucleotide encoding the SHC enzyme or variant thereof, which may be inserted into a vector for expression and optional purification. One type of vector is a plasmid representing a circular double stranded DNA loop into which additional DNA segments are ligated. Certain vectors can control the expression of genes to which they are functionally linked. These vectors are called "expression vectors". Usually expression vectors suitable for DNA recombination techniques are of the plasmid type. Typically, an expression vector comprises a gene such as the SHC enzyme or variant thereof as described herein. In the present description, the terms "plasmid" and "vector" may be used interchangeably since the plasmid is the vector type most often use.

Such vectors can include DNA sequences which include but are not limited to DNA sequences that are not naturally present in the host cell, DNA sequences that are not normally transcribed into RNA or translated into a protein ("expressed") and other genes or DNA sequences which one desires to introduce into the non-recombinant host. It will be appreciated that typically the genome of a recombinant host described herein is augmented through the stable introduction of one or more recombinant genes. However, autonomous or replicative plasmids or vectors can also be used within the scope of this disclosure. Moreover, the present disclosure can be practiced using a low copy number, e.g. a single copy, or high copy number (as exemplified herein) plasmid or vector.

The vector of the present disclosure includes plasmids, phagemids, phages, cosmids, artificial bacterial and artificial yeast chromosomes, knock-out or knock-in constructs, synthetic nucleic acid sequences or cassettes and subsets may be produced in the form of linear polynucleotides, plasmids, megaplasmids, synthetic or artificial chromosomes, such as plant, bacterial, mammalian or yeast artificial chromosomes.

It is preferred that the proteins encoded by the introduced polynucleotide are expressed within the cell upon introduction of the vector. The diverse gene substrates may be incorporated into plasmids. The plasmids are often standard cloning vectors, e.g. bacterial multicopy plasmids. The substrates can be incorporated into the same or different plasmids. Often at least two different types of plasmid having different types of selectable markers are used to allow selection for cells containing at least two types of vectors.

Typically bacterial or yeast cells may be transformed with any one or more nucleotide sequences as is well known in the art. For in vivo recombination, the gene to be recombined with the genome or other genes is used to transform the host using standard transforming techniques. In a suitable embodiment DNA providing an origin of replication is included in the construct. The origin of replication may be suitably selected by the skilled person. Depending on the nature of the genes, a supplemental origin of replication may not be required if sequences are already present with the genes or genome that are operable as origins of replication themselves.

Host Cells, Methods of Making Host Cells and Methods of Making the Compound of Formula (I) Using Host Cells Recombinant host cells may be used in the methods described herein.

There is further provided herein a recombinant host cell comprising a nucleic acid sequence or a construct or a vector as described herein. There is further provided herein a recombinant host cell that produces a SHC enzyme or enzyme variant as described herein.

The processes described herein for producing the compound of formula (I) may, for example, comprise culturing a recombinant host cell as described herein. As used herein, the term "culturing" refers to a process of maintaining living cells such that they produce a SHC enzyme or enzyme variant as described herein that can be used in a process for producing the compound of formula (I) as described herein. It is not necessary for the cells to divide and replicate themselves, although this is not excluded.

A bacterial or yeast cell may be transformed by exogenous or heterologous DNA when such DNA has been introduced inside the cell. The transforming DNA may or may not be integrated, i.e. covalently linked into the genome of the cell. In prokaryotes, and yeast, for example, the transforming DNA may be maintained on an episomal element such as a plasmid. With respect to eukaryotic cells, a stably transfected cell is one in which the transfected DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

Generally, the introduced DNA is not originally resident in the host that is the recipient of the DNA, but it is within the scope of the disclosure to isolate a DNA segment from a given host, and to subsequently introduce one or more additional copies of that DNA into the same host, e.g. to enhance production of the product of a gene or alter the expression pattern of a gene. In some instances, the introduced DNA will modify or even replace an endogenous gene or DNA sequence, e.g. by homologous recombination or site-directed mutagenesis. Suitable recombinant hosts include microorganisms, plant cells, and plants.

The present disclosure also features recombinant hosts. The term "recombinant host", also referred to as a "genetically modified host cell" or a "transgenic cell" denotes a host cell that comprises a heterologous nucleic acid or the genome of which has been augmented by at least one incorporated DNA sequence. A host cell of the present disclosure may be genetically engineered with the polynucleotide or the vector as outlined above.

The host cells that may be used for purposes of the disclosure include but are not limited to prokaryotic cells such as bacteria (for example, *E. coli* and *B. subtilis*), which may, for example, be transformed with, for example, recombinant bacteriophage DNA, plasmid DNA, bacterial artificial chromosome, or cosmid DNA expression vectors containing the polynucleotide molecules of the disclosure; simple eukaryotic cells like yeast (for example, *Saccharomyces* and *Pichia*), which may, for example, be transformed with, for example, recombinant yeast expression vectors containing the polynucleotide molecule of the disclosure. Depending on the host cell and the respective vector used to introduce the polynucleotide of the disclosure the polynucleotide can integrate, for example, into the chromosome or the mitochondria) DNA or can be maintained extrachromosomally like, for example, episomally or can be only transiently comprised in the cells.

The term "cell" as used herein in particular with reference to genetic engineering and introducing one or more genes or an assembled cluster of genes into a cell, or a production cell is understood to refer to any prokaryotic or eukaryotic cell. Prokaryotic and eukaryotic host cells are both contemplated for use according to the disclosure, including bacterial host cells like *E. coli* or *Bacillus* sp. yeast host cells, such as *S. cerevisiae*, insect host cells, such as *Spodoptera frugiperda* or human host cells, such as HeLa and Jurkat.

Specifically, the cell is a eukaryotic cell, preferably a fungal, mammalian or plant cell, or a prokaryotic cell. Suitable eukaryotic cells include, for example, without limitation, mammalian cells, yeast cells, or insect cells (including Sf9), amphibian cells (including melanophore cells), or worm cells including cells of *Caenorhabditis* (including *Caenorhabditis elegans*). Suitable mammalian cells include, for example, without limitation, COS cells (including Cos-1 and Cos-7), CHO cells, HEK293 cells, HEK293T cells, HEK293 T-Rex™ cells, or other transfectable eucaryotic cell lines. Suitable bacterial cells include without limitation *E. coli*.

Preferably prokaryotes, such as *E. coli, Bacillus, Streptomyces*, or mammalian cells, like HeLa cells or Jurkat cells, or plant cells, like *Arabidopsis*, may be used.

The cell may, for example, be selected from prokaryotic, yeast, plant, and/or insect host cells.

Preferably the cell is an *Aspergillus* sp. or a fungal cell, preferably, it can be selected from the group consisting of the genera *Saccharomyces, Candida, Kluyveromyces, Hansenula, Schizosaccharomyces, Yarrowia, Pichia* and *Aspergillus.*

Preferably, the cell us a bacteria cells, for example, having a genus selected from *Escherichia, Streptomyces. Bacillus. Pseudomonas. Lactobacillus* and *Lactococcus*. For example, the bacteria may be *E. coli.*

Preferably the *E. coli* host cell is an *E. coli* host cell which is recognized by the industry and regulatory authorities (including but not limited to an *E. coli* K12 host cell or an *E. coli* BL21 host cell).

One preferred host cell to use with the present disclosure is *E. coli*, which may be recombinantly prepared as described herein. Thus, the recombinant host may be a recombinant *E. coli* host cell. There are libraries of mutants, plasmids, detailed computer models of metabolism and other information available for *E. coli*, allowing for rational design of various modules to enhance product yield. Methods similar to those described above for *Saccharomyces* can be used to make recombinant *E. coli* micro-organisms.

In one embodiment, the recombinant *E. coli* microorganism comprises nucleotide sequences encoding SHC enzyme or enzyme variant genes.

Preferably, the recombinant *E. coli* microorganism comprises a vector construct as described herein. In another preferred embodiment, the recombinant *E. coli* microorganism comprises nucleotide sequences encoding the SHC enzymes and enzyme variants disclosed herein.

Another preferred host cell to use with the present disclosure is *S. cerevisiae* which is a widely used chassis organism in synthetic biology. Thus, the recombinant host may be *S. cerevisiae*. There are libraries of mutants, plasmids, detailed computer models of metabolism and other information available for *S. cerevisiae*, allowing for rational design of various modules to enhance product yield. Methods are known for making recombinant *S. cerevisiae* microorganisms.

Culturing of cells may be performed in a conventional manner. The culture medium may contain a carbon source, at least one nitrogen source and inorganic salts, and vitamins are added to it. The constituents of this medium can be the ones which are conventionally used for culturing the species of microorganism in question. Carbon sources of use in the instant method include any molecule that can be metabolized by the recombinant host cell to facilitate growth and/or production of the compound of formula (I). Examples of suitable carbon sources include, but are not limited to, sucrose (e.g. as found in molasses), fructose, xylose, glycerol, glucose, cellulose, starch, cellobiose or other glucose containing polymer.

In embodiments employing yeast as a host, for example, carbon sources such as sucrose, fructose, xylose, ethanol, glycerol, and glucose are suitable. The carbon source can be provided to the host organism throughout the cultivation period or alternatively, the organism can be grown for a period of time in the presence of another energy source, e.g. protein, and then provided with a source of carbon only during the fed-batch phase.

The suitability of a recombinant host cell microorganism for use in the methods of the present disclosure may be determined by simple test procedures using well known methods. For example, the microorganism to be tested may be propagated in a rich medium (e.g. LB-medium, Bacto-tryptone yeast extract medium, nutrient medium and the like) at a pH, temperature and under reaction conditions commonly used for propagation of the microorganism. Once recombinant microorganisms (i.e. recombinant host cells) are selected that produce the desired products of cyclization, the products are typically produced by a production host cell line on the large scale by suitable expression systems and fermentations, e.g. by microbial production in cell culture. In one embodiment of the present disclosure, a defined minimal medium such as M9A is used for cell cultivation.

The components of M9A medium comprise: 14 g/l $KH_2PO_4$, 16 g/l $K_2HPO_4$, 1 g/l $Na_3Citrate.2H_2O$, 7.5 g/l $(NH_4)_2SO_4$, 0.25 g/l $MgSO_4.7H_2O$, 0.015 g/l $CaCl_2.2H_2O$, 5 g/l glucose and 1.25 g/l yeast extract).

In another embodiment of the present disclosure, nutrient rich medium such as LB was used. The components of LB medium comprise: 10 g/l tryptone, 5 g/l yeast extract, 5 g/l NaCl. Other examples of Mineral Medium and M9 Mineral Medium are disclosed, for example, in U.S. Pat. No. 6,524,831B2 and US 2003/0092143A1.

Another example of a minimal medium may be prepared as follows: for 350 ml culture: to 35 ml citric acid/phosphate stock (133 g/l $KH_2PO_4$, 40 g/l $(NH_4)_2HPO_4$, 17 g/l citric acid.$H_2O$ with pH adjusted to 6.3) was added 307 ml $H_2O$, the pH adjusted to 6.8 with 32% NaOH as required. After autoclaving 0.850 ml 50% $MgSO_4$, 0.035 ml trace elements solution (see below) solution, 0.035 ml Thiamin solution and 7 ml 20% glucose were added.

Trace elements solution: 50 g/i $Na_2EDTA.2H_2O$, 20 g/l $FeSO_4.7H_2O$, 3 g/l $H_3BO_3$, 0.9 g/l $MnSO_4.2H_2O$, 1.1 g/l $CoCl_2$, 80 g/L $CuCl_2$, 240 g/l $NiSO_4.7H_2O$, 100 g/l KI, 1.4 g/l $(NH_4)_6Mo_7O_{24}.4H_2O$, 1 g/l $ZnSO_4.7H_2O$, in deionized water Thiamin solution: 2.25 g/l Thiamin.HCl in deionized water $MgSO_4$ solution: 50% (w/v) $MgSO_4.7H_2O$ in deionized water The recombinant microorganism may be grown in a batch, fed batch or continuous process or combinations thereof. Typically, the recombinant microorganism is grown in a fermenter at a defined temperature(s) in the presence of a suitable nutrient source. e.g. a carbon source, for a desired period of time to produce sufficient enzyme to cyclize the compound of formula (II) (e.g. a compound of formula (IIa) and or (fib)) to the compound of formula (I) and to produce a desired amount of the compound of formula (I). The recombinant host cells may be cultivated in any suitable manner, for example by batch cultivation or fed-batch cultivation.

As used herein, the term “batch cultivation” is a cultivation method in which culture medium and/or nutrients is neither added nor withdrawn during the cultivation.

As used herein, the term “fed-batch” means a cultivation method in which culture medium and/or nutrients is added during the cultivation but no culture medium is withdrawn.

One embodiment of the present disclosure provides a method of producing the compound of formula (I) in a cellular system comprising expressing SHC enzymes or enzyme variants under suitable conditions in a cellular system, feeding the compound of formula (H) (e.g., a compound of formula (IIa) and/or a compound of formula (IIb)) to the cellular system, converting the compound of formula (II) (e.g., a compound of formula (IIa) and/or a compound of formula (fib)) to the compound of formula (I)

using the SHC enzymes or enzyme variants produced using the cellular system, collecting the compound of formula (I) (e.g., a compound of formula (IIa) and/or a compound of formula (fib)) from cellular system and optionally isolating the compound of formula (I) from the system. Expression of other nucleotide sequences may serve to enhance the method. The cyclization method can include the additional expression of other nucleotide sequences in the cellular system. The expression of other nucleotide sequences may enhance the cyclization pathway for making the compound of formula (I).

A further embodiment of the present disclosure is a cyclization method of making the compound of formula (I) comprising growing host cells comprising SHC enzyme or enzyme variant genes, producing SHC enzymes or enzyme variants in the host cells, feeding the compound of formula (II) (e.g., a compound of formula (IIa) and/or a compound of formula (IIb)) to the host cells, incubating the host cells under conditions of pH, temperature and solubilizing agent suitable to promote the conversion of the compound of formula (II) (e.g., a compound of formula (IIa) and/or a compound of formula (IIb)) to the compound of formula (I) and collecting the compound of formula (I). The production of the SHC enzymes or enzyme variants in the host cells provides a method of making the compound of formula (I) when the compound of formula (II) (e.g., a compound of formula (IIa) and/or a compound of formula (IIb)) is added to the host cells under suitable reaction conditions. Achieved conversion may be enhanced by adding more biocatalyst and SOS to the reaction mixture.

The recombinant host cell microorganism may be cultured in a number of ways in order to provide cells in suitable amounts expressing the SHC enzymes or enzyme variants for the subsequent cyclization step. Since the microorganisms applicable for the cyclization step vary broadly (e.g. yeasts, bacteria and fungi), culturing conditions are, of course, adjusted to the specific requirements of each species and these conditions are well known and documented. Any of the art known methods for growing cells of recombinant host cell microorganisms may be used to produce the cells utilizable in the subsequent cyclization step of the present disclosure. Typically the cells are grown to a particular density (measurable as optical density (OD)) to produce a sufficient biomass for the cyclization reaction.

The cultivation conditions chosen influence not only the amount of cells obtained (the biomass) but the quality of the cultivation conditions also influences how the biomass becomes a biocatalyst. The recombinant host cell microorganism expressing the SHC enzyme or enzyme variant gene and producing the SHC enzyme or enzyme variant is termed a biocatalyst which is suitable for use in a cyclization reaction. In some embodiments the biocatalyst is a recombinant whole cell producing SHC enzymes or enzyme variants or it may be in suspension or an immobilized format. In other embodiments, the biocatalyst is a membrane fraction or a liquid fraction prepared from the recombinant whole cell producing the SHC enzyme or enzyme variant (as disclosed for example in Seitz et a/2012—as cited above). The recombinant whole cell producing SHC enzymes or enzyme variants include whole cells collected from the fermenter (for the cyclization reaction) or the cells in the fermenter (which are then used in a one-pot reaction). The recombinant whole cell producing SHC enzymes or enzyme variants can include intact recombinant whole cell and/or cell debris. Either way, the SHC enzyme or enzyme variant is associated with a membrane (such as a cell membrane) in some way in order to receive and/or interact with a substrate (e.g. compound of formula (II)), which membrane (such as a cell membrane) can be part of or comprise a whole cell (e.g. a recombinant whole cell). The SHC enzymes or enzyme variants may also be in an immobilized form (e.g. associated with an enzyme carrier) which allows the SHC enzymes or enzyme variants to interact with a substrate (e.g. compound of formula (II)). The SHC enzymes or enzyme variants may also be used in a soluble form.

In one embodiment, the biocatalyst is produced in sufficient amounts (to create a sufficient biomass), harvested and washed (and optionally stored, e.g. refrigerated, frozen or lyophilized)) before starting the bioconversion step.

In a further embodiment, the cells are produced in sufficient amounts (to create a sufficient biocatalyst) and the reaction conditions are then adjusted without the need to harvest and wash the biocatalyst for the cyclization reaction. This one step (or "one pot") method is advantageous as it simplifies the process while possibly reducing costs. The culture medium used to grow the cells is also suitable for use in the cyclization reaction provided that the reaction conditions are adjusted to facilitate the cyclization reaction.

The optimum pH for growing the cells is in the range of 6.0-7.0. The optimum pH for the cyclization reaction is dependent on the type of SHC enzyme or enzyme variant used in the cyclization reaction. The pH is regulated using techniques which are well known to the Skilled Person.

Whilst the terms "mixture" or "reaction mixture" may be used interchangeably with the term "medium" in the present disclosure (especially as it relates to a "one pot" reaction), it should be noted that growing the cells to create a sufficient biomass requires a cell culture/fermentation medium but a medium is not required for the cyclization step as a reaction buffer will suffice at a suitable pH.

The cyclization methods of the present disclosure are carried out under conditions of time, temperature, pH and solubilizing agent to provide for conversion of the compound of formula (II) (e.g., a compound of formula (IIa) and/or a compound of formula (IIb)) to the compound of formula (I).

The pH of the reaction mixture may be in the range of 4-8, preferably, 5 to 6.5, more preferably 4.8-6.0 for the SHC enzyme variants and in the range of from about pH 5.0 to about pH 7.0 for the wild-type SHC enzymes and can be maintained by the addition of buffers to the reaction mixture. An exemplary buffer for this purpose is a citric acid buffer, a phosphate buffer, an acetic acid buffer and/or a succinic acid buffer.

The preferred temperature is between from about 15° C. and about 60° C., for example from about 15° C. to about 50° C. or from about 15° C. to about 45 C or from about 30° C. to about 60 C or from about 40° C. to about 50° C. The temperature can be kept constant or can be altered during the cyclization process.

It may be useful to include a solubilizing agent (e.g. a surfactant, detergent, solubility enhancer, water miscible organic solvent and the like) in the cyclization reaction.

As used herein, the term "surfactant" means a component that lowers the surface tension (or interfacial tension) between two liquids or between a liquid and a solid.

Surfactants may act as detergents, wetting agents, emulsifiers, foaming agents, and dispersants. Examples of surfactants include but are not limited to Triton X-100, Tween 80, taurodeoxycholate, Sodium taurodeoxycholate, Sodium dodecyl sulfate (SDS), and/or sodium lauryl sulfate (SLS).

Whilst Triton X-100 may be used to partially purify the SHC enzyme or enzyme variant (in soluble or membrane fraction/suspension form), it may also be used in the cyclization reaction (see for example the disclosure in Seitz (2012 PhD thesis as cited above) as well as the disclosure in Neumann and Simon (1986—as cited above) and JP2009060799. SDS may be used as a solubilizing agent.

Without wishing to be bound by theory, the use of SDS with recombinant microbial host cells may be advantageous as the SDS may interact advantageously with the host cell membrane in order to make the SHC enzyme or enzyme variant (which is a membrane bound enzyme) more accessible to the compound of formula (II) (e.g., a compound of formula (IIa) and/or a compound of formula (fib)) substrate. In addition, the inclusion of SOS at a suitable level in the reaction mixture may improve the properties of the emulsion (e.g. compound of formula (II) in water) and/or improve the access of the compound of formula (II) (e.g., a compound of formula (IIa) and/or a compound of formula (IIb)) substrate to the SHC enzyme within the host cell while at the same time preventing the disruption (e.g. denaturation of the SHC (WT or SHC variant) enzyme). The concentration of the solubilising agent (e.g. SDS) used in the cyclization reaction is influenced by the biomass amount and the substrate concentration. That is, there is a degree of interdependency between the solubilising agent (e.g. SDS) concentration, the biomass amount and the substrate concentration. By way of example, as the concentration of compound of formula (II) (e.g., a compound of formula (IIa) and/or a compound of formula (IIb)) substrate increases, sufficient amounts of biocatalyst and solubilising agent (e.g. SDS) are required for an efficient cyclization reaction to take place. If, for example, the solubilising agent (e.g. SDS) concentration is too low, a suboptimal compound of formula (II) (e.g., a compound of formula (IIa) and/or a compound of formula (IIb)) conversion may be observed. On the other hand, if, for example, the solubilising agent (e.g. SDS) concentration is too high, then there may be a risk that the biocatalyst is affected through either the disruption of the intact microbial cell and/or denaturation/inactivation of the SHC enzyme or enzyme variant. The selection of a suitable concentration of SOS in the context of the biomass amount and, substrate (concentration is within the knowledge of the Skilled Person).

The temperature of the cyclization reaction for a WT SHC enzyme (eg. AacSHC) may be from about 30° C. to about 60° C., for example from about 45° C. to about 60° C., for example from about 50° C. to about 60° C., for example about 55° C.

The pH range of the cyclization reaction for a WT SHC enzyme (eg. AacSHC) may be from about 5.0 to 7.0, more preferably from about 5, 6 to about 6.2, even more preferably about 6.0.

The temperature of the cyclization reaction for a SHC enzyme variant may be about 30 C to about 55° C., for example from about 40° C. to about 50° C., for example about 45° C.

The pH of the cyclization reaction for a SHC enzyme variant may be about 4.8-6.4, preferably about 5.2-6.0.

The [SDS]/[cells] ratio may be in the range of about, 10:1-20:1, preferably about 15:1-18:1, preferably about 16:1 when the ratio of biocatalyst to compound of formula (II) is about 2:1.

The optimum temperature for the SHC enzyme variants may, for example, be equal to or greater than about 35° C. For example, the optimum temperature for the SHC enzyme variants may range from about 40° C. to about 50° C., for example from about 42° C. to about 48° C. or from about 44° C. to about 46° C. For example, the optimum temperature of the SHC enzyme variants may be about 45° C. The processes for making the compound of formula (I) disclosed herein may be carried out at the optimum temperature of the SHC enzyme variant.

The optimum pH for the SHC enzyme variants may, for example, be equal to or greater than about 5.4. For example, the optimum pH for the SHC enzyme variants may range from about 5.2 to about 6.0, for example from about 5.4 to about 5.8, for example from about 5.6 to about 5.8. For example, the optimum pH of the SHC enzyme variants may be about 5.6 or about 5.8. The process for making the compound of formula (I) disclosed herein may be carried out at the optimum pH of the SHC enzyme variant.

The optimum concentration of sodium dodecyl sulfate (SDS) in the reaction medium of the process for making the compound of formula (I) disclosed herein may, for example, be from about 0.010 w/w % to about 0.10 w/w %. For example, the optimum concentration of SDS may be from about 0.040 w/w % to about 0.080 w/w %, for example about 0.050 w/w % when the substrate is used at 4 g/l with cells to an $OD_{650\ nm}$, of 10. The process for making the compound of formula (I) disclosed herein may be carved out using the optimum concentration of SDS described herein.

The processes for making the compound of formula (I) disclosed herein may be carried out within the optimum temperature range or at the optimum temperature and/or within the optimum pH range or at the optimum pH and/or within the SOS optimum concentration range or at the optimum SDS concentration for the specific enzyme used, as set out in Table 3 in the Examples below.

In some embodiments, the compound of formula (I) is produced using a biocatalyst to which the compound of formula (II) substrate is added.

It is possible to add the substrate by feeding using known means (e.g. peristaltic pump, infusion syringe and the like). The compound of formula (II) may be oil soluble and provided in an oil format. Given that the biocatalyst (microbial cells such as intact recombinant whole cell and/or cell debris and/or immobilised enzyme) is present in an aqueous phase, the cyclization reaction may be regarded as a three phase system (comprising an aqueous phase, a solid phase and an oil phase) when compound of formula (II) is added to the reaction mixture. This is the case even when SDS is present. By way of clarification, when a soluble WT SHC or a SHC enzyme variant is used as a biocatalyst, this is considered a two phase system.

A fermenter may be used to grow recombinant host cells expressing the SHC enzyme or enzyme variant gene and producing active SHC enzymes or enzyme variants to a sufficient biomass concentration suitable for use as a biocatalyst in the same fermenter vessel which is used to convert the compound of formula (II) source to the compound of formula (I), for example in admixture with one or more of the by product of formula (III).

The Skilled Person will understand that higher cumulative production titers can be achieved by implementing a continuous process, such as product removal, substrate feed, and biomass addition or (partial) replacement. Preferably the cyclization of compound of formula (II) into compound of formula (I) in the presence of a recombinant host cell comprising a SHC enzyme or enzyme variant generates an compound of formula (I) yield of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, given in mol percent and based on the mols of compound of formula (II) employed; especially preferably, the yield is between 5 and 100, 10 and 100, and 100, 25 and 100, 30 and 100, 35 and 100, in particular between 40 and 100, 45 and 100, 50 and 100, 60 and 100, 70 and 100 mol percent.

The activity of the SHC enzyme or enzyme variant is defined via the reaction rate (amount of product/(amount of product+amount of remaining starting material))×100) in mot percent. Preferably, the cyciization of compound of formula (II) into compound of formula (I) in the presence of a SHC enzyme or enzyme variant produces compound of formula (I) yield of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 48, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, given in mol percent and based on the mols of compound of formula (II) employed; especially preferably, the yield is between 5 and 100, 10 and 100, 20 and 100, 25 and 100, 30 and 100, 35 and 100, in particular between 40 and 100, 45 and 100.50 and 100, 60 and 100, 70 and 100.

In a preferred embodiment of the invention, the yield and/or the reaction rate are determined over a defined time period of, for example, 4, 6, 8, 10, 12, 16, 20, 24, 36 or 48 hours, during which compound of formula (II) (e.g., a compound of formula (IIa) and/or a compound of formula (IIb)) is converted into compound of formula (I) by a recombinant host cell comprising a nucleotide sequence encoding a SHC enzyme or enzyme variant. In a further variant, the reaction is carried out under precisely defined conditions of, for example, 25° C., 30° C., 40° C. 50° C. or 60° C. In particular, the yield and/or the reaction rate are determined by carrying out the reaction of converting compound of formula (II) (e.g., a compound of formula (IIa) and/or a compound of formula (IIb)) into compound of formula (I) by the SHC enzymes or enzyme variants according to the invention at 35 C over a period of 24-72 hours.

In a further embodiment of the present invention, a recombinant host cell comprising a nucleotide sequence encoding a SHC enzyme variant is characterized in that it shows a 2-, 3-, 4-, 5-, 6-, 7-, 8-, 9-, 10-, 11-, 12-, 13-, 14-, 15-, 16-, 17-, 18-, 19-, 20-, 21-, 22-, 23-, 24-, 25-, 26-, 27-, 28-, 29-, 30-, 31-, 32-, 33-, 34-, 35-, 36-, 37-, 38-, 39-, 40-, 41-, 42-, 43-, 44-, 45-, 46-, 47-, 48-, 49-, 50-, 51-, 52-, 53-, 54-, 55-, 56-, 57-, 58-, 59-, 60-, 61-, 62-, 63-, 64-, 65-, 68-, 67-, 68-, 69-, 70-, 71-, 72-, 73-, 74-, 75-, 76-, 77-, 78-, 79-, 80-, 81-, 82-, 83-, 84-, 85-, 86-, 87-, 88-, 89-, 90-, 91-, 92-, 93-, 94-, 95-, 96-, 97-, 98-, 99-, 100-, 200-, 500-, 1000-fold or higher yield and/or reaction rates in the reaction of compound of formula (II) (e.g., a compound of formula (IIa) and/or a compound of formula (I*b*)) to give compound of formula (I) in comparison with the WT SHC or SHC derivative enzyme under the same conditions. Here, the term condition relates to reaction conditions such as substrate concentration, enzyme concentration, reaction time and/or temperature.

The successful development of a cyclization process for making compound of formula (I) from compound of formula (II) (e.g., a compound of formula (IIa) and/or a compound of formula (IIb)) in a recombinant strain of *E. coli* comprising a nucleotide sequence encoding a Wt/reference SHC or a SHC derivative can offer a low cost and industrially economical process for compound of formula (I) production.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. The term "comprising" also means "including" as well as "consisting" e.g. a composition "comprising" X may consist exclusively of X or may include something additional e.g. X+Y. It must be noted also that, as used in this specification and the appended claims, the singular forms "a", "an" and "the" include plural referents unless the content dearly dictates otherwise. By way of example, a reference to "a gene" or "an enzyme" is a reference to "one or more genes" or "one or more enzymes".

It is to be understood that this disclosure is not limited to the particular methodology, protocols and reagents described herein as these may vary. It is also to be understood that the terminology used herein is for the purpose of describing particular embodiments only, and is not intended to limit the scope of the present disclosure which will be limited only by the appended claims. Unless defined otherwise, all technical and scientific terms used herein have the same meanings as commonly understood by the person skilled in the art. In accordance with the present disclosure there may be conventional molecular biology, microbiology, and recombinant DNA techniques employed which are within the skill of the art.

This disclosure is not limited in its application to the details of construction and the arrangement of components set forth in the following description or illustrated in the drawings. The disclosure is capable of other embodiments and of being practiced or of being carried out in various ways. Also, the phraseology and terminology used herein is for the purpose of description and should not be regarded as limiting. Preferably, the terms used herein are defined as described in "A multilingual glossary of biotechnological terms: (IUPAC Recommendations)", Leuenberger, H. G. W, Nagel, B. and Kolbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety.

The examples described herein are illustrative of the present disclosure and are not intended to be limitations thereon. Different embodiments of the present disclosure have been described according to the present disclosure. Many modifications and variations may be made to the techniques described and illustrated herein without departing from the spirit and scope of the disclosure. Accordingly, it should be understood that the examples are illustrative only and are not limiting upon the scope of the disclosure.

EXAMPLES

Example 1: Synthesis of E E/Z-Ethyl-homofarnesol

A composition comprising a mixture of E,E- and E,2-stereoisomers of ethyl-homofarnesol was made by the scheme illustrated in FIG. 1.

To a suspension of potassium carbonate (79.4 g, 575 mmol, 1.0 equiv) in DMF (1250 ml) was added ethyl 3-oxopentanoate (91.2 g, 632 mmol) and the mixture was stirred for 20 minutes at room temperature. Geranylbromide (125 g, 575 mmol, 1 equiv) was added and the mixture was stirred at room temperature for 16 h. After the addition of ice and stirring for 10 minutes, the product was extracted with ethyl acetate (3 times 650 ml). The combined organic layer were washed with water (twice 650 ml) and brine (650 ml), dried over $Na_2SO_4$, filtered and concentrated under vacuum. The crude product was purified by column chromatography over silica gel using 0-4% of EtOAc in petrolether to yield methyl (E)-5,9-dimethyl-2-propionyldeca-4,8-dienoate (2) (120 g, 74%) as a liquid.

To a solution of 2 (57 g, 203.2 mmol, 1.0 Equiv) in methanol (210 ml) was added aqueous 5N KOH solution (114 ml) at room temperature. The solution was then heated to reflux under stirring for 2.5 h, then cooled to room temperature and 2N HCl until pH 3-4. The product was extracted with ethyl acetate (twice 250 ml) and the combined organic layer was washed with water (twice 100 ml) and brine (100 ml), dried over anhydrous $Na_2SO_4$ and the solvent was removed under reduced pressure. The crude (E)-7,11-dimethyldodeca-6,10-dien-3-one (3) thus obtained (35 g, 83%) was further converted without purification.

To a stirred suspension of sodium hydride (23.3 g, 576 mmol, 3.0 equiv) in THE (200 ml) was added triethyl phosphonoacetate (129.1 g, 576 mmol, 3.0 equiv) in THF (100 ml) dropwise over a period of 2 h at −10° C. and stirred at room temperature for additional 30 min. A solution of 3 prepared above (40 g, 192 mmol, 1.0 equiv) in THF (100 ml) was added drowise over a period of one hour. The reaction mixture was stirred at room temperature for 3-4 h. The reaction mixture was poured on to ice and then the product was extracted with ethyl acetate (0.8 L) and organic layer was washed with water (400 ml) and brine (400 ml). The organic layer was dried over $Na_2SO_4$ and the solvent was evaporated under reduced pressure to yield ethyl 3-ethyl-7,11-dimethyldodeca-2,6,10-trienoate (4) (40 g, 75%) as a liquid. The crude compound was used in the next step without purification.

To an ice cooled solution of DIBAL-H (593 ml, 593 mmol, 3.0 equiv) in THE (500 ml) was added dropwise a solution of 4 (55 g, 197.5 mmol, 1.0 equiv) in THF (100 ml). The reaction mixture was stirred at room temperature for 4 h. The reaction was quenched with saturated ammonium chloride solution (300 ml) at 0° C. and stirred for 30 minutes. The mixture was filtered through Celite and the Celite bed was washed with ethyl acetate (1 L). The filtrate was washed with water and brine. The organic layer was dried over $Na_2SO_4$ and solvent was evaporated on rotary evaporator. The crude product was purified by column chromatography over silica gel using 0-15% of EtOAc in petrolether to afford 3-ethyl-7,11-dimethyldodeca-2,6,10-trien-1-ol (5) (43 g, 92%) as a liquid.

To a solution of 5 (50 g, 212 mmol, 1.0 equiv) in DMF (500 ml) was dropwise added s-collidine (103 g, 846 mmol, 4.0 equiv) at room temperature. The reaction mixture was cooled to 0° C., then mesyl chloride (48.3 g, 423 mmol, 2.0 equiv) was added dropwise over a period of one hour. The reaction mixture was stirred at room temperature for 2 h. Lithium chloride (35.7 g, 846 mmol) was added and the mixture was stirred at room temperature for 16 h. The reaction was quenched with ice-water (1 L) and the product was extracted with petrol ether (1 L). The organic layer was washed with water (three times 500 ml) and brine (500 ml). The organic layer was dried over sodium sulphate and concentrated under reduced pressure to yield 1-chloro-3-ethyl-7,11-dimethyldodeca-2,6,10-triene (6) (50 g). The crude product was used without any purification.

To a stirred solution of KCN (34.7 g, 533 mmol, 2.3 equiv) in DMSO (500 ml) was drop wise added a solution of 6 (59 g, 232 mmol) in DMSO (100 ml) at room temperature. The reaction mixture was stirred at room temperature overnight. The reaction was quenched with ice cold water (2.0 L) and the product was extracted with ethyl acetate (twice 1 L). The combined organic layer was washed with water (three times 750 ml) and brine (750 ml). The organic layer was dried over sodium sulfate and concentrated under reduced pressure to afford 4-ethyl-8,12-dimethyltrideca-3,7,11-trienenitrile (7) (56 g, 98%) as a liquid.

To a stirred solution of 7 prepared above (29 g, 118 mmol, 1.0 equiv) in ethanol (232 ml) was added a solution of KOH (53.0 g, 945 mmol, 8.0 equiv) in water (232 ml). The reaction mixture was stirred at reflux for overnight. Ethanol was removed under reduced pressure and the residue was cooled to 5-10° C. The mixture was acidified with 1.5 N HCl to pH 3-4 and diluted with water. The product was extracted with DCM (twice 500 ml) and the combined organic layer was washed with water (500 ml). The organic layer was dried and concentrated under vacuum. The crude product was purified by column chromatography over silica gel using 0-60% of EtOAc in petrolether to yield 4-ethyl-8,12-dimethyltrideca-3,7,11-trienoic acid (8) (14 g, 45%) as a liquid.

To a suspension of LAH (2.75 g, 72.6 mmol, 1.2 equiv) in THF (140 ml) was added a solution of 8 as prepared above (16 g, 60.5 mmol, 1.0 equiv) in THF (40 ml) at −10° C. The reaction mixture was stirred at room temperature for 3 h. The reaction mixture was cooled to 0° C. and slowly quenched with water (2.75 ml), 10% sodium hydroxide solution (2.75 ml) and again water (8.25 ml). The suspension was stirred at room temperature for 30 minutes and then filtered through a Celite bed. The filtrate was concentrated and the residue was purified by column chromatography followed by fractional distillation to yield 4-ethyl-8,12-dimethyltrideca-3,7,11-trien-1-ol as a liquid (10.5 g, 69%) as a slightly yellow mixture. GC-MS analysis indicates the presence of 6 double bond and E,Z-isomers (relative peak areas 39; 23; 23; 3; 2; 2%).

Figure 4:
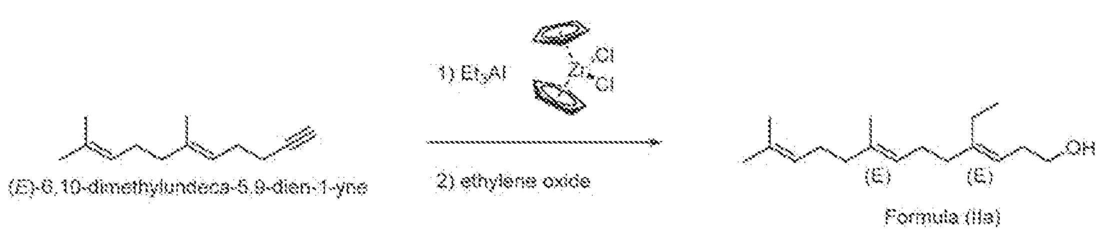
FIG. 4 shows the reaction scheme used to produce E,E-ethyl-homofarnesol

$^1$H-NMR (400 MHz, $CDCl_3$): 5.06-5.17 (m, 3H), 3.59-3.68 (m, 2H), 2.27-2.37 (m, 2H), 1.95-2.15 (m, 11H), 1.69 (br. s, 3H), 1.61 (br. s, 6H), 0.96-1.06 (m, 3H). $^{13}$C-NMR (100 MHz, $COCl_3$, major 3 isomers): 144.6 (s), 144.4 (s), 135.3 (s), 135.1 (s), 135.0 (s), 131.3 (s), 131.3 (s), 131.2 (s), 124.4 (d), 124.3 (d), 124.3 (d), 124.2 (d), 124.1 (d), 124.1 (d), 124.0 (d), 119.3 (d), 118.8 (d), 62.8 (t), 62.6 (t), 62.5 (t), 39.7 (t), 39.7 (t), 36.8 (t), 36.5 (t), 33.2 (t), 31.3 (t), 31.1 (t), 31.1 (t), 30.5 (t), 29.8 (t), 29.6 (t), 27.0 (t), 26.7 (t), 26.7 (t), 26.6 (t), 25.7 (q), 23.4 (t), 23.2 (t), 17.7 (q), 16.0 (q), 15.9 (q), 13.3 (q), 13.2 (q), 13.2 (q), 12.8 (q). MS (EI, 70 eV): (isomer 1, rt 9.29 min, 3%) 136(11), 123(12), 107(12), 93(10), 81(40), 69(100), 55(13), 41(56); (isomer 2, rt 9.31 min, 2%) 250 (<1, M+), 136(5), 123(16), 107(11), 81(32), 69(100), 55(13), 41(40); (isomer 3, rt 9.56 min, 2%) 181(4), 166(4), 137(15), 109(15), 95(36), 81(83), 69(100), 55(33), 41(60); (isomer 4, rt 9.67 min, 23%), 250 (<1, M), 235(<1), 181(2), 136(1), 121(11), 107(7), 95(19), 81(49), 69(100), 55(21), 41(49); (isomer 5, rt 9.72 min, 39%) 250 (<1, $M^+$), 235(<1), 181(4), 136(13), 121(10), 107(9), 95(21), 81(36), 69(100), 55(20), 41(48); (isomer 6, rt 9.82 min, 23%), 250 (<1, $M^+$), 235(<1), 181(3), 136(7), 121(12), 107(9), 95(25), 81(36), 69(100), 55(16), 41(51);

Example 2: Synthesis of E,E-ethyl-homofarnesol made by the scheme illustrated in FIG. 4

A solution of (E)-6,10-dimethylundeca-5,9-dien-1-yne (8.0 g, 45.4 mmol) and bis-dicyclopentadienyl zirconium dichloride (13.3 g, 45.4 mmol) in dichloromethane (150 mL) was cooled under stirring to −50° C. A solution of Methyl aluminium in hexane (1.0 M, 136 mL, 136 mmol, 3 equiv.) was added dropwise, upon which the temperature rose to −45° C. After complete addition, the cooling bath was removed and stirring continued at room temperature for 8 hours. After cooling to −10° C., the solution of ethylene oxide in THE (2.5 M, 20 mL, 50 mmol, 1.1 equiv.) was added dropwise, upon which the temperature rose to 0° C. After complete addition the cooling bath was removed and stirring was continued for 19 hours at room temperature. The mixture was filtered and the filtrate was poured carefully on 300 mL ice-cold 2 M aqueous HCl-solution. After extraction with MTBE (150 mL), the organic layer was washed with water (200 mL) and with dilute aqueous NaCl solution (pH neutral). The organic layer was dried over $MgSO_4$, suction filtered and the filtrate was concentrated on a rotary evaporator to yield 15.3 g of a clear, yellow liquid, which was purified by flash chromatography on silica gel, eluting with heptane/MTBE 4:1 to isolate (3E,7E)-4-ethyl-8,12-dimethyltrideca-3,7,11-trien-1-ol (3.26 g, 29%) as a clear, colourless liquid (gas chromatographical purity 81%).

$^1$H-NMR (400 MHz, $CDCl_3$): 4.93-5.02 (m, 3H), 3.49 (t, J=6.5 Hz, 2H), 2.17 (q, J=6.7 Hz, 2H), 1.82-2.01 (m, 11H), 1.56 (d, J=1.0 Hz, 3H), 1.48 (s, 6H), 0.86 (t, J=7.5 Hz, 3H). $^{13}$C-NMR (100 MHz, $CDCl_3$): 144.8 (s), 135.2 (s), 131.3 (s), 124.3 (d), 124.1 (d), 119.3 (d), 62.6 (t), 39.7 (t), 36.5 (t), 31.2 (t), 28.7 (t), 26.7 (t), 25.7 (q), 23.2 (t), 17.7 (q), 16.0 (q), 13.3 (q). MS (EI, 70 eV): 250 (<1), 235 (<1), 221 (<1), 207 (2), 181 (5), 166 (4), 137 (17), 121 (14), 107 (11), 95 (25), 81 (42), 69 (100), 55 (22), 41 (49).

Example 3: Production and Testing of New SHC Enzyme Variants

SHC Plasmid Preparation

The gene encoding a wild-type or variant squalene hopene cyclase (SHC) enzyme was inserted into plasmid pET-28a (+), where it is under the control of an IPTG inducible T7-promotor for protein production in *Escherichia coli*. The plasmid was transformed into *E. coli* strain BL21(DE3) using a standard heat-shock transformation protocol.

Media Preparation

The minimal medium chosen as default was prepared as follows for 350 ml culture: to 35 ml citric acid/phosphate stock (133 g/l $KH_2PO_4$, 40 g/l $(NH_4)_2HPO_4$, 17 g/l citric acid.$H_2O$ with pH adjusted to 6.3) was added 307 ml $H_2O$, the pH adjusted to 6.8 with 32% NaOH as required. After autoclaving 0.850 ml 50% $MgSO_4$, 0.035 ml trace elements solution (see below), 0.035 ml Thiamin solution and 7 ml 20% glucose were added.

Trace elements solution: 50 g/l $Na_2EDTA.2H_2O$, 20 g/l $FeSO_4.7H_2O$, 3 g/l $H_3BO_3$, 0.9 g/l $MnSO_4.2H_2O$, 1.1 g/l $CoCl_2$, 80 g/L $CuCl_2$, 240 g/l $NiSO_4.7H_2P$, 100 g/l KI, 1.4 g/l $(NH_4)_5Mo_7O_{24}.4H_2O$, 1 g/l $ZnSO_4.7H_2O$, in deionized water Thiamin solution: 2.25 g/l Thiamin.HCl in deionized water $MgSO_4$ solution: 50% (w/v) $MgSO_4.7H_2O$ in deionized water SHC Enzyme of Enzyme Variant Production (Biocatalyst Production)

Small Scale Biocatalyst Production (Wild-Type SHC or SHC Variants)

350 ml culture (medium supplemented with 50 μg/ml kanamycin) were inoculated from a preculture of the *E. coli* strain BL21(DE3) containing the SHC production plasmid. Cells were grown to an optical density of approximately 0.5 ($OD_{650\ nm}$) at 37° C. with constant agitation (250 rpm). Enzyme production was then induced by the addition of IPTG to a concentration of 300 μM followed by incubation for a further 5-6 hours with constant shaking. The resulting biomass was finally collected by centrifugation and washed with e.g. 50 mM Tris-HCl buffer pH 7.5. The cells were stored as pellets at 4° C. or −20° C. until further use. In general 2.5 to 4 grams of cells (wet weight) were obtained from 1 litre of culture, independently of the medium used.

Biocatalyst Production in Fermenters

Fermentations were prepared and run in 750 ml InforsHT reactors. To the fermentation vessel was added 168 ml deionized water. The reaction vessel was equipped with all required probes ($pO_2$, pH, sampling, antifoam), C+N feed and sodium hydroxide bottles and autoclaved. After autoclaving is added to the reactor 20 ml 10× phosphate/citric acid buffer 14 ml 50% glucose 0.53 ml $MgSO_4$ solution 2 ml $(NH_4)_2SO_4$ solution 0.020 ml trace elements solution 0.400 ml thiamine solution 0.200 ml kanamycin stock The running parameters were set are as follows: pH=6.95, $pO_2$=40%, T=30° C. Stirring at 300 rpm. Cascade: rpm setpoint at 300, min 300, max 1000, flow (l/min) set point 0.1, min 0, max 0.6. Antifoam control, 1:9.

The fermenter was inoculated from a seed culture to an $OD_{650\ nm}$ of 0.4-0.5. This seed culture was grown in LB medium (+Kanamycin) at 37° C., 220 rpm for 8 h. The fermentation was run first in batch mode for 11.5 h, where after was started the C+N feed with a feed solution (sterilized glucose solution (143 ml $H_2O$+35 g glucose) to which had been added after sterilization: 17.5 ml $(NH_4)_2SO_4$ solution, 1.8 ml $MgSO_4$ solution, 0.018 ml trace elements solution, 0.360 ml Thiamine solution, 0.180 ml kanamycin stock. The feed was run at a constant flow rate of approx. 4.2 ml/h. Glucose and $NH_4^+$ measurements were done externally to evaluate availability of the C- and N-sources in the culture. Usually glucose levels stay very low.

Cultures were grown for a total of approximately 25 hours, where they reached typically an $OD_{650\ nm}$ of 40-45. SHC production was then started by adding IPTG to a concentration of approx. 1 mM in the fermenter (as IPTG pulse or over a period of 3-4 hours using an infusion syringe), setting the temperature to 40 C and $pO_2$ to 20%. Induction of SHC production lasted for 16 h at 40° C. At the end of induction the cells were collected by centrifugation, washed with 0.1 M citric acid/sodium citrate buffer pH 5.4 and stored as pellets at 4° C. or −20° C. until further use.

Results

Six SHC enzyme variants were derived from the AacSHC enzyme variant 21562 disclosed in WO 2016/170099. The six new SHC enzyme variants have the mutations (compared to wild-type AacSHC) listed in Table 2 below. These mutations are in addition to the mutations M132R, A224V and 14321, which were present in the 21562 SHC enzyme variant (parent enzyme).

TABLE 2

Mutations in selected new SHC variant enzymes.

| SHC Variant | Y81H | T90A | A172T | M277K | H431L | A557T | R613S |
|---|---|---|---|---|---|---|---|
| 110B8 (SEQ ID NO: 5) | + | | | | + | + | |
| 90C7 (SEQ ID NO: 17) | | + | | | | | + |
| 115A7 (SEQ ID NO: 18) | | | + | + | | | |
| SHC 49 (SEQ ID NO: 2) | | | | | + | + | |
| SHC 65 (SEQ ID NO: 3) | | | | | | + | + |
| SHC 66 (SEQ ID NO: 4) | + | | | | | + | + |

Note:
these mutations appear in addition to the mutations present in 215G2SHC: M132R, A224V, and I432T The new mutations identified in the SHC variants created are not in the vicinity of the active site of the enzyme as was observed previously when evolving wild-type *Alicyclobacillus acidocaldarius* SHC to 215G2SHC. The majority of the new mutations identified are located again in domain 2 of the crystal structure of the enzyme (T90A, A1721, M277K and H431L). Two are located in domain 1 (A557T and R613S) and 1 at the interface between the 2 domains (Y81H).

Example 4: Optimization of Reaction Conditions for New SHC Enzyme Variant

Reaction parameters investigated: temperature, SOS concentration and pH

Results

Reactions of 2-5 ml volume with 4 g/l EEH and biocatalyst loaded at an $OD_{650\ nm}$ of 10.0 were run in 0.1 M citric acid/sodium phosphate buffer pH 5.0-6.8, in the presence of 0.0125-0.125% SOS at temperatures ranging from 28 to 50° C. and under constant agitation (Heidolph synthesis 1 Liquid device, 900 rpm).

The conditions listed in Table 3 below appeared to be the individual optimal conditions. They were confirmed in reactions run in 0.1 M succinic acid/NaOH buffer at pH around pH defined earlier as optimal.

TABLE 3

Optimal reaction conditions for SHC variant enzymes.

| SHC Variant | Optimal Temp. (° C.) | Optimal Temp. Range (° C.) | Optimal pH | Optimal pH range | Optimal [SDS] (w/w %) | Optimal [SDS] range (w/w %) |
|---|---|---|---|---|---|---|
| 215G2 (SEQ ID NO: 10) | 35 | 32-50 | 5.4 | 5.0-6.2 | 0.060 | 0.010-0.10 |
| 110B8 (SEQ ID NO: 5) | 45 | 40-50 | 5.8 | 5.6-6.0 | 0.050 | 0.040-0.070 |
| SHC 49 (SEQ ID NO: 2) | 45 | 40-50 | 5.6 | 5.4-5.8 | 0.050 | 0.040-0.080 |
| SHC 65 SEQ ID NO: 3) | 45 | 40-50 | 5.6 | 5.2-5.8 | 0.050 | 0.040-0.10 |
| SHC 66 (SEQ ID NO: 4) | 45 | 40-46 | 5.8 | 5.6-6.0 | 0.060 | 0.040-0.080 |
| 90C7 (SEQ ID NO: 17) | 45 | 40-46 | 5.6 | 5.2-6.0 | 0.040 | 0.025-0.050 |
| 115A7 (SEQ ID NO: 18) | 35 | 32-36 | 5.4 | 5.2-5.8 | 0.050 | 0.040-0.075 |

The reaction conditions for the SHC variants listed in Table 2 above in relation to Example 3 were individually optimized with regards to temperature, pH and SDS concentration.

Biocatalyst was prepared from the different variants by fermentation as described above using the *E. coli* cells transformed with the corresponding plasmid. Cells were collected by centrifugation, and stored at −20° C. until further used. The biocatalysts produced showed very similar SHC content. It could therefore be concluded that the differences in activity observed were due to the inserted mutations.

Some deviation from the 215G2SHC parent enzyme was noted. With only one exception the introduction of the new mutations shifted optimal temperature by 10° C. from 35° C. to about 45° C.

Example 5: Cyclization of Ethyl-homofarnesol

Method—SHC Cyclization of Ethyl-Homofarnesol

The activity of wild-type and variant SHC enzymes was tested under reaction conditions individually defined as optimal and as set out in Example 4 (temperature, pH, SDS concentration), or at pH 6.0, 55T and in the presence of 0.060% SOS with wild type *Alicyclobacillus acidocaldarius* (Aac) SHC. The reactions (5 ml volume) contained 4 g/l Ethyl-homofarnesol prepared according to Example 1. Cells that had produced the SHC variants or WT Aac SHC were added to an $OD_{650\ nm}$ of 10.0 to start the reaction. The reactions were incubated on a Heidolph Synthesis 1 Liquid 16 device under constant agitation (900 rpm).

Results—SHC Cyclization of Ethyl-Homofarnesol

Ethyl-homofarnesol cyclization was successful with 21502 SHC and variants of this enzyme. The amino acid mutations introduced in 215G2 SHC slightly increased conversion with all variants, and significantly with one of them (SHC #65) (see Table 4 below).

TABLE 4

Cyclization of Ethyl-homofarnesol to 3a-ethyl-6,6,9a-trimethyl dodecahydronaphtho[2,1-b]furan with SHC enzymes

| SHC Enzyme or Enzyme Variant | Ethyl-homofarnesol conversion (%) 4 h | 23 h |
|---|---|---|
| Aac wt SHC (SEQ ID NO: 1) | 0.7 | 2.0 |
| 215G2 SHC (SEQ ID NO: 10) | 2.1 | 6.8 |
| 115A7 SHC (SEQ ID NO: 18) | 3.0 | 9.5 |
| 90C7 SHC (SEQ ID NO: 17) | 3.0 | 9.1 |
| 110B8 (SEQ ID NO: 5) | 2.8 | 7.0 |
| SHC #49 (SEQ ID NO: 6) | 2.9 | 7.1 |
| SHC #65 (SEQ ID NO: 3) | 5.1 | 15.5 |
| SHC #66 (SEQ ID NO: 4) | 3.3 | 7.4 |

Ethyl-homofarnesol conversion in reactions run at 4 g/i substrate and with biocatalyst loaded at an $OD_{650\ nm}$ of 10.0 applying individually optimized reaction conditions (1, pH, [SDS]).

Example 6: Cyclization of E,E/Z-Ethyl-homofarnesol

The reaction vessel (0.75 l Infors fermenter) was loaded with a total amount of 2.9 g Ethyl-homofarnesol prepared according to Example 1 (2.0 g were added at reaction start and a further 0.9 g approximately 48 hours later), 1.95 g SDS was added from a 15.5% (w/w) solution prepared in deionized water. A cell suspension was prepared from *E. coli* cells that had produced the 215G2 SHC variant (as outlined in Example 3) by suspending the cells in 0.1 M succinic acid/NaOH buffer pH 5.1. After determination of the cell wet weight concentration of this cell suspension by centrifugation for 10 min at 10° C. and 17210 g, the appropriate volume of cells was added to the reaction vessel in order to introduce 37.5 g of cells into the reaction.

The volume of the reaction was completed to 150 g with the required amount of reaction buffer pH 5.1. The reaction was run at 35° C. and pH 5.4 under constant stirring (700 rpm). The pH was set to 5.4 using 85% $H_3PO_4$. pH regulation was done manually using 85% phosphoric acid as required. The reaction was sampled over time (1 ml), extracted with 5 volumes of MTBE/tBME (5 ml). The substrate and product content of the reaction was determined by GC analysis after clarification of the solvent phase by centrifugation (table top centrifuge, 13000 rpm, 2 min). About 75% Ethyl-homofarnesol conversion was obtained in the reaction that was run for approx. 4 days.

The crude MTBE extract was concentrated on a rotary evaporator and the residue was filtered over silica gel with MTBE as eluent. After removal of the solvent, a brown liquid (4.3 g) was obtained, which was purified by flash chromatography over silica gel with heptane/MTBE 50:1. From this a white, crystalline solid was obtained (300 mg, 10% isolated yield), which consisted of 85% of compound of Formula (I) and 14% of compound of Formula (III). The identity of compound of Formula (I) was confirmed by comparison of its NMR and MS data with the pure compound of Formula (I) obtained in Example 7. Its enantiomeric excess was determined as >99.% (for the preparation of a racemic reference sample see Example 7). The unequivocal assignment of the relative configuration of compound of Formula (III) required the use of 3D-HSQC-NOESY NMR-spectroscopy due to signal crowding in diagnostically important areas of the $^1$H-NMR spectra. The NMR-data of the compound of Formula (III) are given in the following.

$^1$H-NMR (600 MHz, $C_6D_6$) 3.82 (td, J=8.8, 2.1 Hz, 1H), 3.63-3.69 (m, 1H), 1.73-1.84 (m, 2H), 1.65-1.73 (m, 2H), 1.48-1.63 (m, 4H), 1.36 (br dd, J=12.8, 3.0 Hz, 3H), 1.06-1.14 (m, 8H), 0.97 (s, 3H), 0.87 (s, 3H), 0.78 (s, 3H). $^{13}$C-NMR ($C_6D_6$, extracted from HMBC): 82.3 (s), 64.7 (1), 54.7 (d), 47.5 (d), 42.5 (t), 39.5 (t), 36.2 (s), 33.7 (q), 33.5 (t), 33.0 (s), 32.1 (t), 29.0 (t), 22.3 (q), 22.0 (q), 20.6 (t), 18.9 (t), 8.7 (q). MS (EI, 70 eV): 250 (<1, M+), 235 (1), 221 (100, [M-C2H5]+), 137 (32), 121 (9), 109 (13), 97 (50), 81 (19), 69 (17), 55 (17), 41 (15), 29 (5).

A racemic reference of the compound of Formula (III) was prepared by preparative GC-chromatography from a commercial sample of Grisalva®. This sample was subjected to analytical separation on a GC-apparatus equipped with an FID detector, a sniffing port (split ratio 1:1) and a chiral column (Hydrodex-beta-3P, Machery-Nagel, P/N 723358.25). Further conditions: 11.11 injection volume (1000 ng/μl in MtBE), split 20:1, hot needle injection technique, injector 230° C., carrier gas $H_2$, constant flow 1.5 ml/min, temperature program 2 min at 50° C.-2° C./min-2 min at 230° C. Under these conditions, the two enantiomers of the compound of the racemic sample of Formula (III) eluted at 63.78 and 64.10 min. The compound of Formula (III) obtained with SHC as described above (14% in mixture with compound of Formula (I)) eluted at 63.78 min. Thus, the first peak corresponds to (3aR,5aS,9aS,9bS)-3a-ethyl-6,6,9a-trimethyldodecahydronaphtho[2,1-b]furan. The enantiomeric excess was >99%. The odour of both peaks of the racemic product was assessed by experienced panelists. The first peak was perceived as strong woody, warm, ambra, tobacco and slightly animalic, whereas the second peak was perceived as weak, woody, ambra at the injected sample amount. Thus, the herein prepared enantiomer of Formula (III), (3aR,5aS,9aS,9bS)-3a-ethyl-6,6,9a-trimethyldodecahydronaphtho[2,1-b]furan, is preferred and stronger than (3aS,5aR,9aR,9bR)-3a-ethyl-6,6,9a-trimethyldodecahydronaphtho[2,1-b]furan.

Example 7: Cyclization of E,E-Ethyl-homofarnesol

The reaction vessel (0.75 l Infors fermenter) was loaded with a total amount of 2.1 g E,E-Ethyl-homofarnesol prepared according to Example 2 (1.0 g were added at reaction start, a further 0.6 g and 0.5 g at approximately 7 and 23 hours later); 1.9 g SOS was added from a 31.0% (w/w) solution prepared in deionized water. A cell suspension was prepared from *E. coli* cells that had produced the 215G2 SHC variant (as outlined in Example 3) by suspending the cells in 0.1 M succinic acid/NaOH buffer pH 5.1. After determination of the cell wet weight concentration of this cell suspension by centrifugation for 10 min at 10° C. and 17210 g, the appropriate volume of cells was added to the reaction vessel in order to introduce 41.8 g of cells into the reaction. The volume of the reaction was completed to 135 g with the required amount of reaction buffer pH 5.1. The reaction was run at 35° C. and pH 5.4 under constant stirring (700 rpm). The pH was set to 5.4 using 85% $H_3PO_4$. pH regulation was done manually using 85% phosphoric acid as required. The reaction was sampled overtime (1 ml), extracted with 5 volumes of MTBE/tBME (5 ml). The substrate and product content of the reaction was determined by GC analysis after clarification of the solvent phase by centrifugation (table top centrifuge, 13000 rpm, 2 min).

About 90% Ethyl-homofarnesol conversion was obtained in the reaction that was run for approx. 2 days. The reaction was extracted 5 times with 100 ml MTBE by vigorous shaking followed by phase separation (centrifugation at 3500 g for 10 min, room temperature). This allowed full extraction of the reaction product and remaining unconverted substrate as judged from GC-analysis of the recovered solvent phases.

The crude MTBE (methyl tert butyl ether) extract of the biotransformation was concentrated to 100 mL and diluted with heptane (100 mL). The solution was filtered over a plug of silica gel. After removal of the solvents, a dark yellow liquid was obtained (2.15 g), which was purified by flash column chromatography on silica gel, eluting with heptane/MTBE 15:1 to isolate (3aR,5aS,9aS,9bR)-3a-ethyl-6,6,9a-trimethyldodecahydronaphtho[2,1-b]furan (600 mg, 38%) as a white crystalline solid (m.p. 60.4-61.3° C., purity according to GC-MS 99%).

$[\alpha]_D$=−34° (c=006, $CHCl_3$)

$^1$H-NMR (400 MHz, $CDCl_3$): 3.75-3.87 (m, 2H), 2.11-2.17 (m, 1H), 1.60-1.79 (m, 4H), 1.36-1.54 (m, 6H), 1.13-1.32 (m, 3H), 0.96-1.09 (m, 2H), 0.88 (s, 3H), 0.84 (s, 3H), 0.85 (t, J=7.5 Hz, 3H), 0.83 (s, 3H). $^{13}$C-NMR (100 MHz, $COCl_3$); 81.5 (s), 64.7 (t), 61.3 (d), 57.6 (d), 42.5 (t), 40.0 (t), 36.3 (s), 35.3 (t), 33.6 (q), 33.1 (s), 23.3 (t), 22.6 (t), 21.1 (q), 20.4 (t), 18.4 (t), 15.5 (q), 7.9 (q). MS (EI, 70 eV): 250 (<1, $M^+$), 235 (2), 221 (100, (M-C2H4), 137 (40), 121 (9), 109 (8), 97 (51), 81 (22), 69 (20), 55 (25), 41 (27), 29 (13).

A racemic sample of the compound of Formula (I) was prepared as follows. To the stirred solution of E,E-Ethylhomofarnesol prepared according to Example 2 (580 mg, 2.34 mmol) in $CH_2Cl_2$ (40 mL) at −78° C. was added dropwise fluorosulfonic acid (0.27 mL, 2 equiv.) stirring was continued for 45 min. The solution was poored on 100 mL of water and extracted with MTBE. The organic layer was washed with water and brine and dried over $MgSO_4$. The crude yellow liquid was purified by flash chromatography on silica gel eluting with heptane/MTBE 10:1 to yield a colourless liquid (370 mg, 64%), which contained, according to GC-MS, besides other isomers 49% of the compound of Formula (I) in racemic form. This compound was isolated in pure form by preparative GC-chromatography and served as the racemic reference for the SHC-derived pure product. The racemic sample and the compound obtained by SHC-cyclization were subjected to chiral GC-analysis and chiral GC-sniff as described in Example 6. The two enantiomers present in the racemic sample eluted at 66.00 min and 66.69 min. The (−)-enantiomer of Formula (I) prepared by SHC-cyclization as described hereabove eluted at 66.00 min and its e.e. was 99.94% (see FIG. 3). The odour of both peaks of the racemic product was assessed by three experienced panelists. The first peak was perceived as strong woody, warm, ambra, tobacco and slightly animalic, whereas the second peak was perceived as odourless at the injected sample amount. Thus, the herein prepared (−)-enantiomer of Formula (I), (3aR,5aS,9aS,9bR)-3a-ethyl-6,6,9a-trimethyldodecahydronaphtho[2,1-b]furan, is the preferred one and much stronger than (3aS,5aR,9aR,9bS)-3a-ethyl-6,6,9a-trimethyldodecahydronaphtho[2,1-b]furan.

The foregoing broadly describes certain embodiments of the present invention without limitation. Variations and modifications as will be readily apparent to those skilled in the art are intended to be within the scope of the present invention as defined in and by the appended claims

SEQUENCE LISTING

```
SEQ ID NO: 1 (amino acid sequence of wild-type AacSHC)
MAEQLVEAPAYARTLDRAVEYLLSCQKDEGYWWGPLLSNVTMEAEYVLLCHILDRVDRDRMEKIRRYL
LHEQREDGTWALYPGGPPDLDTTIEAYVALKYIGMSRDEEPMQKALRFIQSQGGIESSRVFTRMWLAL
VGEYPWEKVPMVPPEIMFLGKRMPLNIYEFGSWARATVVALSIVMSRQPVFPLPERARVPELYETDVP
PRRRGAKGGGGWIFDALDRALHGYQKLSVHPFRRAAEIRALDWLLERQAGDGSWGGIQPPWFYALIAL
KILDMTQHPAFIKGWEGLELYGVELDYGGWHFQASISPVWDTGLAVLALRAAGLPADHDRLVKAGEWL
LDRQITVPGDWAVKRPNLKPGGFAFQFDNVYYPDVDDTAVVVWALNTLRLPDERRRRDAMTKGFRWIV
GMQSSNGGWGAYDVDNTSDLPNHIPFCDFGEVTDPPSEDVTAHVLECFGSFGYDDAWKVIRRAVEYLK
REQKPDGSWFGRWGVNYLYGTGAVVSALKAVGIDTREPYIQKALDWVEQHQNPDGGWGEDCRSYEDPA
YAGKGASTPSQTAWALMALIAGGRAESEAARRGVQYLVETQRPDGGWDEPYYTGTGFPGDFYLGYTMY
RHVFPTLALGRYKQATERR

SEQ ID NO: 2 (amino acid sequence of SHC enzyme variant #49)
MAEQLVEAPAYARTLDRAVEYLLSCQKDEGYWWGPLLSNVTMEAEYVLLCHILDRVDRDRME
KIRRYLLHEQREDGTWALYPGGPPDLDTTIEAYVALKYIGMSRDEEPMQKALRFIQSQGGIE
SSRVFTRRKLALVGEYPWEKVPMVPPEIMFLGKRMPLNIYEFGSWARATVVALSIVMSRQPV
FPLPERARVPELYETDVPPRRRGAKGGGGWIFDALDRVLHGYQKLSVHPFRRAAEIRALDWL
LERQAGDGSWGGIQPPWFYALIALKILDMTQHPAFIKGWEGLELYGVELDYGGWMFQASISP
VWDTGLAVLALRAAGLPADHDRLVKAGEWLLDRQITVPGDWAVKRPNLKPGGFAFQFDNVYY
PDVDDTAVVVWALNTLRLPDERRRRDAMTKGFRWIVGMQSSNGGWGAYDVDNTSDLPNLTPF
CDFGEVTDPPSEDVTAHVLECFGSFGYDDAWKVIRRAVEYLKREQKPDGSWFGRWGVNYLYG
TGAVVSALKAVGIDTREPYIQKALDWVEQHQNPDGGWGEDCRSYEDPAYAGKGASTPSQTTW
ALMALIAGGRAESEAARRGVQYLVETQRPDGGWDEPYYTGTGFPGDFYLGYTMYRHVFPTLA
LGRYKQAIERR

SEQ ID NO: 3 (amino acid sequence of SHC enzyme variant #65)
MAEQLVEAPAYARTLDRAVEYLLSCQKDEGYWWGPLLSNVTMEAEYVLLCHILDRVDRDRME
KIRRYLLHEQREDGTWALYPGGPPDLDTTIEAYVALKYIGMSRDEEPMQKALRFIQSQGGIE
SSRVFTRRWLALVGEYPWEKVPMVPPEIMFLGKRMPLNIYEFGSWARATVVALSIVMSRQPV
```

-continued

SEQUENCE LISTING

FPLPERARVPELYETDVPPRRRGAKGGGGWIFDALDRVLHGYQKLSVHPFRRAAEIRALDWL
LERQAGDGSWGGIQPPWFYALIALKILDMTQHPAFIKGWEGLELYGVELDYGGWMFQASISP
VWDTGLAVLALRAAGLPADHDRLVKAGEWLLDRQITVPGDWAVKRPNLKPGGFAFQFDNVYY
PDVDDTAVVVWALNTLRLPDERRRRDAMTKGFRWIVGMQSSNGGWGAYDVDNTSDLPNHTPF
CDFGEVTDPPSEDVTAHVLECFGSFGYDDAWKVIRRAVEYLKREQKPDGSWFGRWGVNYLYG
TGAVVSALKAVGIDTREPYIQKALDWVEQHQNPDGGWGEDCRSYEDPAYAGKGASTPSQTTW
ALMALLAGGRAESEAARRGVQYLVETQRPDGGWDEPYYTGTGFPGDFYLGYTMYSHVFPTLA
LGRYKQAIERR

SEQ ID NO: 4 (amino acid sequence Of SHC enzyme variant #66)
MAEQLVEAEAYARTLDRAVEYLLSCQKDEGYWWGPLLSNVTMEAEYVLLCHILDRVDRDRMEKTRRYL
LHEQREDGTWALHPGGPPDLDTTIEAYVALKYIGMSRDEEPMQKALRFIQSQGGIESSRVFTRRWLAL
VGEYPWEKVPMVPPEIMFLGKRMPLNIYEFGSWARATVVALSIVMSRQPVFPLPERARVPELYETDVP
PRRRGAKGGGGWIFDALDRVLHGYQKLSVHPFRRAAEIRALDWLLERQAGDGSWGGIQPPWFYALIAL
KILDMTQHPAFIKGWEGLELYGVELDYGGWMFQASISPVWDTGLAVLALAAAGLPADADHLVKAGEWL
LDRQITVPGDWAVKRPNLKPGGFAFQFDNVYYPDVDDTAVVVWALNTLRLPDERRRRDAMTKGFRWTV
GMQSSNGGWGAYDVDNTSDLPNHTPFCDFGEVTDPPSEDVTAHVLECFGSFGYDDAWKVIRRAVEYLK
REQKPDGSWFGRWGVNYLYGTGAVVSALKAVGIDTREPYIQKALDWVEQHQNPDGGWGEDCRSYEDPA
YAGKGASTPSQTTWALMALIAGGRAESEAARRGVQYLVETQRPDGGWDEPYYTGTGFPGDFYLGYTMY
SHVFPTLALGRYKQAIERR SEQ ID NO: 5 (amino acid sequence of SHC enzyme variant #110B8)
MAEQLVEAPAYARTLDRAVEYLLSCQKDEGYWWGPLLSNVTMEAEYVLLCHILDRVDRDRMEKIRRYL
LHEQREDGTWALHPGGPPDLDTTIEAYVALKYIGMSRDEEPMQKALRFIQSQGGIESSRVFTRRWLAL
VGEYPWEKVPMVPPEIMFLGKRMPLNIYEFGSWARATVVALSIVMSRQPVFPLPERARVPELYETDVP
PRRRGAKGGGGWIFDALDRVLHGYQKLSVHPFRRAAEIRALDWLLERQAGDGSWGGIQPPWFYALIAL
KILDMTQHPAFIKGWEGLELYGVELDYGGWMFQASISPVWDTGLAVLALRAAGLPADHDRLVKAGEWL
LDRQITVPGDWAVKRPNLKPGGFAFQFDNVYYPDVDDTAVVVWALNTLRLPDERRRRDAMTKGFRWIV
GMQSSNGGWGAYDVDNTSDLPNLTPFCDFGEVTDPPSEDVTAHVLECFGSFGYDDAWKVIRRAVEYLK
REQKPDGSWFGRWGVNYLYGTGAVVSALKAVGIDTREPYTQKALDWVEQHQNPDGGWGEDCRSYEDPA
YAGKGASTPSQTTWALMALIAGGRAESEAARRGVQYLVETQRPDGGWDEPYYTGTGFPGDFYLGYTMY
RHVFPTLALGRYKQAIERR SEQ ID NO: 6 (nucleotide sequence of SHC enzyme variant #49)
ATGGCTGAGCAGTTGGTGGAAGCTCCGGCCTACGCGCGGACGCTGGATCGCGCGGTGGAGTATCTCCT
CTCCTGCCAAAAGGACGAAGGCTACTGGTGGGGGCCGCTTCTGAGCAACGTCACGATGGAAGCGGAGT
ACGTCCTCTTGTGCCACATTCTCGATCGCGTCGATCGGGATCGCATGGAGAAGATCCGGCGGTACCTG
TTGCACGAGCAGCGCGAGGACGGCACGTGGGCCCTGTACCCGGGTGGGCCGCCGGACCTCGACACGAC
CATCGAGGCGTACGTCGCGCTCAAGTATATCGGCATGTCGCGCGACGAGGAGCCGATGCAGAAGGCGC
TCCGGTTCATTCAGAGCCAGGGCGGGATCGAGTCGTCGCGCGTGTTCACGCGGAGGTGGCTGGCGCTG
GTGGGAGAATATCCGTGGGAGAAGGTGCCCATGGTCCCGCCGGAGATCATGTTCCTCGGCAAGCGCAT
GCCGCTCAACATCTACGAGTTTGGCTCGTGGGCTCGGGCGACCGTCGTGGCGCTCTCGATTGTGATGA
GCCGCCAGCCGGTGTTCCCGCTGCCCGAGCGGGCGCGCGTGCCCGAGCTGTACGAGACCGACGTGCCT
CCGCGCCGGCGCGGTGCCAAGGGAGGGGGTGGGTGGATCTTCGACGCGCTCGACCGGGTGGTGCACGG
GTATCAGAAGCTGTCGGTGCACCCGTTCCGCCGCGCGGCCGAGATCCGCGCCTTGGACTGGTTGCTCG
AGCGCCAGGCCGGAGACGGCAGCTGGGGCGGGATTCAGCCGCCTTGGTTTTACGCGCTCATCGCGCTC
AAGATTCTCGACATGACGCAGCATCCGGCGTTCATCAAGGGCTGGGAAGGTCTAGAGCTGTACGGCGT
GGAGCTGGATTACGGAGGATGGATGTTTCAGGCTTCCATCTCGCCGGTGTGGGACACGGGCCTCGCCG
TGCTCGCGCTGCGCGCTGCGGGGCTTCCGGCCGATCACGACCGCTTGGTCAAGGCGGGCGAGTGGCTG
TTGGACCGGCAGATCACGGTTCCGGGCGACTGGGCGGTGAAGCGCCCGAACCTCAAGCCGGGCGGGTT
CGCGTTCCAGTTCGACAACGTGTACTACCCGGACGTGGACGACACGGCCGTCGTGGTGTGGGCGCTCA
ACACCCTGCGCTTGCCGGACGAGCGCCGCAGGCGGGACGCCATGACGAAGGGATTCCGCTGGATTGTC
GGCATGCAGAGCTCGAACGGCGGTTGGGGCGCCTACGACGTCGACAACACGAGCGATCTCCCGAACCT
CACCCCGTTCTGCGACTTCGGCGAAGTGACCGATCCGCCGTCAGAGGACGTCACCGCCCACGTGCTCG
AGTGTTTCGGCAGCTTCGGGTACGATGACGCCTGGAAGGTCATCCGGCGCGCGGTGGAATATCTCAAG
CGGGAGCAGAAGCCGGACGGCAGCTGGTTCGGTCGTTGGGGCGTCAATTACCTCTACGGCACGGGCGC
GGTGGTGTCGGCGCTGAAGGCGGTCGGGATCGACACGCGCGAGCCGTACATTCAAAAGGCGCTCGACT
GGGTCGAGCAGCATCAGAACCCGGACGGCGGCTGGGGCGAGGACTGCCGCTCGTACGAGGATCCGGCG
TACGCGGGTAAGGGCGCGAGCACCCCGTCGCAGACGACCTGGGCGCTGATGGCGCTCATCGCGGGCGG
CAGGGCGGAGTCCGAGGCCGCGCGCCGCGGCGTGCAATACCTCGTGGAGACGCAGCGCCCGGACGGCG
GCTGGGATGAGCCGTACTACACCGGCACGGGCTTCCCAGGGGATTTCTACCTCGGCTACACCATGTAC
CGCCACGTGTTTCCGACGCTCGCGCTCGGCCGCTACAAGCAAGCCATCGAGCGCAGGTGA SEQ ID NO: 7 (nucleotide sequence of SHC enzyme variant #65)
ATGGCTGAGCAGTTGGTGGAAGCTCCGGCCTACGCGCGGACGCTGGATCGCGCGGTGGAGTATCTCCT
CTCCTGCCAAAAGGACGAAGGCTACTGGTGGGGGCCGCTTCTGAGCAACGTCACGATGGAAGCGGAGT
ACGTCCTCTTGTGCCACATTCTCGATCGCGTCGATCGGGATCGCATGGAGAAGATCCGGCGGTACCTG
TTGCACGAGCAGCGCGAGGACGGCACGTGGGCCCTGTACCCGGGTGGGCCGCCGGACCTCGACACGAC
CATCGAGGCGTACGTCGCGCTCAAGTATATCGGCATGTCGCGCGACGAGGAGCCGATGCAGAAGGCGC
TCCGGTTCATTCAGAGCCAGGGCGGGATCGAGTCGTCGCGCGTGTTCACGCGGAGGTGGCTGGCGCTG
GTGGGAGAATATCCGTGGGAGAAGGTGCCCATGGTCCCGCCGGAGATCATGTTCCTCGGCAAGCGCAT
GCCGCTCAACATCTACGAGTTTGGCTCGTGGGCTCGGGCGACCGTCGTGGCGCTCTCGATTGTGATGA
GCCGCCAGCCGGTGTTCCCGCTGCCCGAGCGGGCGCGCGTGCCCGAGCTGTACGAGACCGACGTGCCT
CCGCGCCGGCGCGGTGCCAAGGGAGGGGGTGGGTGGATCTTCGACGCGCTCGACCGGGTGCTGCACGG
GTATCAGAAGCTGTCGGTGCACCCGTTCCGCCGCGCGGCCGAGATCCGCGCCTTGGACTGGTTGCTCG
AGCGCCAGGCCGGAGACGGCAGCTGGGGCGGGATTCAGCCGCCTTGGTTTTACGCGCTCATCGCGCTC
AAGATTCTCGACATGACGCAGCATCCGGCGTTCATCAAGGGCTGGGAAGGTCTAGAGCTGTACGGCGT -continued

| SEQUENCE LISTING |
|---|
| GGAGCTGGATTACGGAGGATGGATGTTTCAGGCTTCCATCTCGCCGGTGTGGGACACGGGCCTCGCCG<br>TGCTCGCGCTGCGCGCTGCGGGGCTTCCGGCCGATCACGACCGCTTGGTCAAGGCGGGCGAGTGGCTG<br>TTGGACCGGCAGATCACGGTTCCGGGCGACTGGGCGGTGAAGCGCCCGAACCTCAAGCCGGGCGGGTT<br>CGCGTTCCAGTTCGACAACGTGTACTACCCGGACGTGGACGACACGGCCGTCGTGGTGTGGGCGCTCA<br>ACACCCTGCGCTTGCCGGACGAGCGCCGCAGGCGGGACGCCATGACGAAGGGATTCCGCTGGATTGTC<br>GGCATGCAGAGCTCGAACGGCGGTTGGGGCGCCTACGACGTCGACAACACGAGCGATCTCCCGAACCA<br>CACCCCGTTCTGCGACTTCGGCGAAGTGACCGATCCGCCGTCAGAGGACGTCACCGCCCACGTGCTCG<br>AGTGTTTCGGCAGCTTCGGGTACGATGACGCCTGGAAGGTCATCCGGCGCGCGGTGGAATATCTCAAG<br>CGGGAGCAGAAGCCGGACGGCAGCTGGTTCGGTCGTTGGGGCGTCAATTACCTCTACGGCACGGGCGC<br>GGTGGTGTCGGCGCTGAAGGCGGTCGGGATCGACACGCGCGAGCCGTACATTCAAAAGGCGCTCGACT<br>GGGTCGAGCAGCATCAGAACCCGGACGGCGGCTGGGGCGAGGACTGCCGCTCGTACGAGGATCCGGCG<br>TACGCGGGTAAGGGCGCGAGCACCCCGTCGCAGACGACCTGGGCGCTGATGGCGCTCATCGCGGGCGG<br>CAGGGCGGAGTCCGAGGCCGCGCGCCGCGGCGTGCAATACCTCGTGGAGACGCAGCGCCCGGACGGCG<br>GCTGGGATGAGCCGTACTACACCGGCACGGGCTTCCCAGGGGATTTCTACCTCGGCTACACCATGTAC<br>AGCCACGTGTTTCCGACGCTCGCGCTCGGCCGCTACAAGCAAGCCATCGAGCGCAGGTGA<br><br>SEQ ID NO: 8 (nucleotide sequence of SHC enzyme variant #66)<br>ATGGCTGAGCAGTTGGTGGAAGCTCCGGCCTACGCGCGGACGCTGGATCGCGCGGTGGAGTATCTCCT<br>CTCCTGCCAAAAGGACGAAGGCTACTGGTGGGGGCCGCTTCTGAGCAACGTCACGATGGAAGCGGAGT<br>ACGTCCTCTTGTGCCACATTCTCGATCGCGTCGATCGGGATCGCATGGAGAAGATCCGGCGGTACCTG<br>TTGCACGAGCAGCGCGAGGACGGCACGTGGGCCCTGCACCCGGGTGGGCCGCCGGACCTCGACACGAC<br>CATCGAGGCGTACGTCGCGCTCAAGTATATCGGCATGTCGCGCGACGAGGAGCCGATGCAGAAGGCGC<br>TCCGGTTCATTCAGAGCCAGGGCGGGATCGAGTCGTCGCGCGTGTTCACGCGGAGGTGGCTGGCGCTG<br>GTGGGAGAATATCCGTGGGAGAAGGTGCCCATGGTCCCGCCGGAGATCATGTTCCTCGGCAAGCGCAT<br>GCCGCTCAACATCTACGAGTTTGGCTCGTGGGCTCGGGCGACCGTCGTGGCGCTCTCGATTGTGATGA<br>GCCGCCAGCCGGTGTTCCCGCTGCCCGAGCGGGCGCGCGTGCCCGAGCTGTACGAGACCGACGGGCCT<br>CCGCGCCGGCGCGGTGCCAAGGGAGGGGGTGGGTGGATCTTCGACGCGCTCGACCGGGTGCTGCACGG<br>GTATCAGAAGCTGTCGGTGCACCCGTTCCGCCGCGCGGCCGAGATCCGCGCCTTGGACTGGTTGCTCG<br>AGCGCCAGGCCGGAGACGGCAGCTGGGGCGGGATTCAGCCGCCTTGGTTTTACGCGCTCATCGCGCTC<br>AAGATTCTCGACATGACGCAGCATCCGGCGTTCATCAAGGGCTGGGAAGGTCTAGAGCTGTACGGCGT<br>GGAGCTGGATTACGGAGGATGGATGTTTCAGGCTTCCATCTCACCGGTGTGGGACACGGGCCTCGCCG<br>TGCTCGCGCTGCGCGCTGCGGGGCTTCCGGCCGATCACGACCGCTTGGTCAAGGCGGGCGAGTGGCTG<br>TTGGACCGGCAGATCACGGTTCCGGGCGACTGGGCGGTGAAGCGCCCGAACCTCAAGCCGGGCGGGTT<br>CGCGTTCCAGTTCGACAACGTGTACTACCCGGACGTGGACGACACGGCCGTCGTGGTGTGGGCGCTCA<br>ACACCCTGCGCTTGCCGGACGAGCGCCGCAGGCGGGACGCCATGACGAAGGGATTCCGCTGGATTGTC<br>GGCATGCAGAGCTCGAACGGCGGTTGGGGCGCCTACGACGTCGACAACACGAGCGATCTCCCGAACCA<br>CACCCCGTTCTGCGACTTCGGCGAAGTGACCGATCCGCCGTCAGAGGACGTCACCGCCCACGTGCTCG<br>AGTGTTTCGGCAGCTTCGGGTACGATGACGCCTGGAAGGTCATCCGGCGCGCGGTGGAATATCTCAAG<br>CGGGAGCAGAAGCCGGACGGCAGCTGGTTCGGTCGTTGGGGCGTCAATTACCTCTACGGCACGGGCGC<br>GGTGGTGTCGGCGCTGAAGGCGGTCGGGATCGACACGCGCGAGCCGTACATTCAAAAGGCGCTCGACT<br>GGGTCGAGCAGCATCAGAACCCGGACGGCGGCTGGGGCGAGGACTGCCGCTCGTACGAGGATCCGGCG<br>TACGCGGGTAAGGGCGCGAGCACCCCGTCGCAGACGACCTGGGCGCTGATGGCGCTCATCGCGGGCGG<br>CAGGGCGGAGTCCGAGGCCGCGCGCCGCGGCGTGCAATACCTCGTGGAGACGCAGCGCCCGGACGGCG<br>GCTGGGATGAGCCGTACTAGACCGGCACGGGCTTCCCAGGGGATTTCTACCTCGGCTACACCATGTAC<br>AGCCACGGTGTTTCCGACGCTCGCGCTCGGCCGCTACAAGCAAGCCATCGAGCGCAGGTGA<br><br>SEQ ID NO: 9 (nucleotide sequence of SHC enzyme variant #110B8)<br>ATGGCTGAGCAGTTGGTGGAAGCTCCGGCCTACGCGCGGACGCTGGATCGCGCGGTGGAGTATCTCCT<br>CTCCTGCCAAAAGGACGAAGGCTACTGGTGGGGGCCGCTTCTGAGCAACGTCACGATGGAAGCGGAGT<br>ACGTCCTCTTGTGCCACATTCTCGATCGCGTCGATCGGGATCGCATGGAGAAGATCCGCCGGTACCTG<br>TTGCACGAGCAGCGCGAGGACGGCACGTGGGCCCTGCACCCGGGTGGGCCGCCGGACCTCGACACGAC<br>CATCGAGGCGTACGTCGCGCTCAAGTATATCGGCATGTCGCGCGACGAGGAGCCGATGCAGAAGGCGC<br>TCCGGTTCATTCAGAGCCAGGGCGGGATCGAGTCGTCGCGCGTGTTCACGCGGAGGTGGCTGGCGCTG<br>GTGGGAGAATATCCGTGGGAGAAGGTGCCCATGGTCCCGCCGGAGATCATGTTCCTCGGCAAGCGCAT<br>GCCGCTCAACATCTACGAGTTTGGCTCGTGGGCTCGGGCGACCGTCGTGGCGCTCTCGATTGTGATGA<br>GCCGCCAGCCGGTGTTCCCGCTGCCCGAGCGGGCGCGCGTGCCCGAGCTGTACGAGACCGACGTGCCT<br>CCGCGCCGGCGCGGTGCCAAGGGAGGGGGTGGGTGGATCTTCGACGCGCTCGACCGGGTGCTGCACGG<br>GTATCAGAAGCTGTCGGTGCACCCGTTCCGCCGCGCGGCCGAGATCCGCGCCTTGGACTGGTTGCTCG<br>AGCGCCAGGCCGGAGACGGCAGCTGGGGCGGGATTCAGCCGCCTTGGTTTTACGCGCTCATCGCGCTC<br>AAGATTCTCGACATGACGCAGCATCCGGCGTTCATCAAGGGCTGGGAAGGTCTAGAGCTTGTACGGCG<br>GGAGCTGGATTACGGAGGATGGATGTTTCAGGCTTCCATCTCGCCGGTGTGGGACACGGGCCTCGCCG<br>TGCTCGCGCTGCGCGCTGCGGGGCTTCCGGCCGATCACGACCGCTTGGTCAAGGCGGGCGAGTGGCTG<br>TTGGACCGGCAGATCACGGTTCCGGGCGACTGGGCGGTGAAGCGCCCGAACCTCAAGCCGGGCGGGTT<br>CGCGTTCCAGTTCGACAACGTGTACTACCCGGACGTGGACGACACGGCCGTCGTGGTGTGGGCGCTCA<br>ACACCCTGCGCTTGCCGGACGAGCGCCGCAGGCGGGACGCCATGACGAAGGGATTCCGCTGGATTGTC<br>GGCATGCAGAGCTCGAACGGCGATTGGGGCGCCTACGACGTCGACAACACGAGGGATCTCCCGAACCT<br>CACCCCGTTCTGCGACTTCGGCGAAGTGACCGATCCGCCGTCAGAGGACGTCACCGCCCACGTGCTCG<br>AGTGTTTCGGCAGCTTCGGGTACGATGACGCCTGGAAGGTCATCCGGCGCGCGGTGGAATATCTCAAG<br>CGGGAGCAGAAGCCGGACGGCAGCTGGTTCGGTCGTTGGGGCGTCAATTACCTCTACGGCACGGGCGC<br>GGTGGTGTCGGCGCTGAAGGCGGTCGGGATCGACACGCGCGAGCCGTACATTCAAAAGGCGCTCGACT<br>GGGTCGAGCAGCATCAGAACCCGGACGGCGGCTGGGGCGAGGACTGCCGCTCGTACGAGGATCCGGCG<br>TACGCGGGTAAGGGCGCGAGCACCCCGTCGCAGACGACCTGGGCGCTGATGGCGCTCATCGCGGGCGG<br>CAGGGCGGAGTCCGAGGCCGCGCGCCGCGGCGTGCAATACCTCGTGGAGACGCAGCGCCCGGACGGCG<br>GCTGGGATGAGCCGTACTACACCGGCACGGGCTTCCCAGGGGATTTCTACCTCGGCTACACCATGTAC<br>CGCCACGTGTTTCCGACGCTCGCGCTCGGCCGCTACAAGCAAGCCATCGAGCGCAGGTGA |

-continued

SEQUENCE LISTING

SEQ ID NO: 10 (amino acid sequence of Aac 215G2 SHC enzyme variant)
MAEQLVEAPAYARTLDRAVEYLLSCQKDEGYWWGPLLSNVTMEAEYVLLCHILDRVDRDRMEKIRRYL
LHEQREDGTWALYPGGPPDLDTTIEAYVALKYIGMSRDEEPMQKALRFIQSQGGIESSRVFTRRWLAL
VGEYPWEKVPMVPPEIMFLGKRMPLNIYEFGSWARATVVALSIVMSRQPVFPLPERARVPELYETDVP
PRRRGAKGGGGWIFDALDRVLHGYQKLSVHPFRRAAEIRALDWLLERQAGDGSWGGIQPPWFYALIAL
KILDMTQHPAFIKGWEGLELYGVELDYGGWMFQASISPVWDTGLAVLALRAAGLPADHDRLVKAGEWL
LDRQITVPGDWAVKRPNLKPGGFAFQFDNVYYPDVDDTAVVVWALNTLRLPDERRRRDAMTKGFRWIV
GMQSSNGGWGAYDVDNTSDLPNHTPFCDFGEVTDPPSEDVTAHVLECFGSFGYDDAWKVIRRAVEYLK
REQKPDGSWFGRWGVNYLYGTGAVVSALKAVGIDTREPYIQKALDWVEQHQNPDGGWGEDCRSYEDPA
YAGKGASTPSQTAWALMALIAGGRAESEAARRGVQYLVETQRPDGGWDEPYYTGTGFPGDFYLGYTMY
RHVFPTLALGRYKQAIERR SEQ ID NO: 11 (amino acid sequence of wild-type ZmoSHC1)
MGIDRMNSLSRLLMKKIFGAEKTSYKPASDTIIGTDTLKRPNRRPEPTAKVDKTIFKTMGNSLNNTLV
SACDWLIGQQKPDGHWVGAVESNASMEAEWCLALWFLGLEDHPLRPRLGNALLEMQREDGSWGVYFGA
GNGDINATVEAYAALRSLGYSADNPVLKKAAAWIAEKGGLKNIRVFTRYWLALIGEWPWEKTPNLPPE
IIWFPDNFVFSIYNFAQWARATMVPIAILSARRPSRPLRPQDRLDELFPEGRARFDYELPKKEGIDLW
SQFFRTTDRGLHWVQSNLLKRNSLREAAIRHVLEWIIRHQDADGGWGGIQPPWVYGLMALHGEGYQLY
HPVMAKALSALDDPGWRHDRGESSWIQATNSPVWDTMLALMALKDAKAEDRFTPEMDKAADWLLARQV
KVKGDWSIKLPDVEPGGWAFEYANDRYPDTDDTAVALIALSSYRDKEEWQKKGVEDAITRGVNWLIAM
QSECGGWGAFDKDNNRSILSKIPFCDFGESIDPPSVDVTAHVLEAFGTLGLSRDMPVIQKAIDYVRSE
QEAEGAWFGRWGVNYIYGTGAVLPALAAIGEDMTQPYITKACDWLVAHQQEDGGWGESCSSYME SEQ ID NO: 12 (amino acid sequence of wild-type ZmoSHC2)
MTVSTSSAFHHSPLSDDVEPIIQKATRALLEKQQQDGHWVFELEADATIPAEYILLKHYLGEPEDLET
EAKIGRYLRRIQGEHGGWSLFYGGDLDLSATVKAYFALKMIGDSPDAPHMLRARNEILARGGAMRANV
FTRIQLALFGAMSWEHVPQMPVELMLMPEWFPVHINKMAYWARTVLVPLLVLQALKPVARNRRGILVD
ELFVPDVLPTLQESGDPIWRRFFSALDKVLHKVEPYWPKNMRAKAIHSCVHFVTERLNGEDGLGAIYP
AIANSVMMYDALGYPENHPERAIARRAVEKLMVLDGTEDQGDKEVYCQPCLSPIWDTALVAHAMLEVG
GDEAEKSAISALSWLKPQQILDVKGDWAWRRPDLRPGGWAFQYRNDYYPDVDDTAVVTMAMDRAAKLS
DLHDDFEESKARAMEWTIGMQSDNGGWGAFDANNSYTYLNNIPFADHGALLDPPTVDVSARCVSMMAQ
AGISITDPKMKAAVDYLLKEQEEDGSWFGRWGVNYIYGTWSALCALNVAALPHDHLAVQKAVAWLKTI
QNEDGGWGENCDSYALDYSGYEPMDSTASQTAWALLGLMAVGEANSEAVTKGINWLAQNQDEEGLWKE
DYYSGGGFPRVFYLRYHGYSKYFPLWALARYRNLKKANQPIVHYGM SEQ ID NO: 13 (amino acid sequence of wild-type BipSHC)
MTVTSSASARATRDPGNYQTALQSTVRAAADWLIANQKPDGHWVGRAESNACMEAGWCLALWFMGLED
HPLRKRLGQSLLDSQRPDGAWQVYFGAPNGDTNATVEAYAALRSLGFRDDEPAVRRAREWIEAKGGLR
NIRVFTRYWLALIGEWPWEKTPNIPPEVIWFPLWFPFSTYNFAQWARATLMPTAVLSARRPSRPLPPE
NRLDALFPHGRKAFDYELPVKAGAGGWDRFFRGADKVLHKLQNLGNRLNLGLFRPAATSRVLEWMIRH
QDFDGAWGGIQPPWIYGLMALYAEGYPLNHPVLAKGLDALNDPGWRVDVGDATYIQATNSPVWDTILT
LLAFDDAGVLGDYPEAVDKAVDWVLQRQVRVPGDWSMKLPHVKPGGWAFEYANNYYPDTDDTAVALIA
LAPLRHDPEWKAKGIDEAIQLGVDWLIGMQSQGGGWGAFDKDNNQKILTKIPFCDYGEALDPPSVDVT
AHTTEAFGKLGISRNHPSMVQALDYIRREQEPSGPWFGRWGVNYVYGTGAVLPALAAIGEDMTQPYIG
RACDWLVAHQQADGGWGESCASYMDVSAVGRGTTTASQTAWALMALLAANRPQDKDAIERGCMWLVER
QSAGTWDEPEFTGTGFPGYGVGQTTKLNDPALSQRLMQGPELSRAFMLRYGMYRHYFPLMALGRALRP
QSHS SEQ ID NO: 14 (amino add sequence of wild-tpe GmoSHC)
MSPADISTKSSSFQRLDNMLPEAVSSACDWLIDQQKPDGHWVGPVESNACMEAQWCLALWFLGQEDHP
LRPRLAQALLEMQREDGSWGIYVGADHGDINTTVEAYAALRSMGYAADMPIMAKSAAWIQQKGGLRNV
RVFTRYWLALTGEWPWDKTPNLPPEITWLPDNFIFSIYNFAQWARATMMPLTILSARRPSRPLLPENR
LDGLFPEGRENFDYELPVKGEEDLWGRFFRAADKGLHSLQSFPVRRFVPREAAIRHVIEWIIRHQDAD
GGWGGIQPPWIYGLMALSVEGYPLHHPVLAKAMDALNDPGWRRDKGDASWIQATNSPVWDTMLAVLAL
HDAGAEDRYSPQMDKAIGWLLDRQVRVKGDWSIKLPDTEPGGWAFEYANDKYPDTDDTAVALIALAGC
RHRPEWRERDIEGAISRGVNWLLAMQSSSGGWGAFDKDNNRSILTKIPFCDFGEALDPPSVDVTAHVL
EAFGLLGISRNHPSVQKALAYIRSEQERNGAWFGRWGVNYVYGTGAVLPALAAIGEDMTQPYTVRACD
WLMSVQQENGGWGESCASYMDINAVGHGVATASQTAWALIGLLAAKRPKDREAIARGCQFLIERQEDG
SWTEEEYTGTGFPGYGVGQAIKLDDPSLPDRLLQGAELSRAFMLRYDLYRQYFPVMALSRARRMMKED
ASAAA SEQ ID NO: 15 (nucleotide sequence encoding the polypeptide of wild-type AacSHC)
ATGGCTGAGCAGTTGGTGGAAGCGCCGGCCTACGCGCGGACGCTGGATCGCGCGGTGGAGTATCTCCT
CTCCTGCCAAAAGGACGAAGGCTACTGGTGGGGGCCGCTTCTGAGCAACGTCACGATGGAAGCGGAGG
ACGTCCTCTTGTGCCACATTCTCGATCGCGTCGATCGGGATCGCATGGAGAAGATCCGGCGGTACCTG
TTGCACGAGCAGCGCGAGGACGGCACGTGGGCCCTGTACCCGGGTGGGCCGCCGGACCTCGACACGAC
CATCGAGGCGTACGTCGCGCTCAAGTATATCGGCATGTCGCGCGACGAGGAGCCGATGCAGAAGGCGC
TCCGGTTCATTCAGAGCCAGGGCGGGATCGAGTCGTCGCGCGTGTTCACGCGGATGTGGCTGGCGCTG
GTGGGAGAATATCCGTGGGAGAAGGTGCCCATGGTCCCGCCGGAGATCATGTTCCTCGGCAAGCCCAT
GCCGCTCAACATCTACGAGTTTGGCTCGTGGGCTCGGGCGACCGTCGTGGCGCTCTCGATTGTGATGA
GCCGCCAGCCGGTGTTCCCGCTGCCCGAGCGGGCGCGCGTGCCCGAGCTGTACGAGACCGACGTGCCT
CCGCGCCGGCGCGGTGCCAAGGGAGGGGGTGGGTGGATCTTCGACGCGCTCGACCGGGCGCTGCACGG
GTATCAGAAGCTGTCGGTGCACCCGTTCCGCCGCGCGGCCGAGATCCGCGCCTTGGACTGGTTGCTCG
AGCGCCAGGCCGGAGACGGCAGCTGGGGCGGGATTCAGCCGCCTTGGTTTTACGCGCTCATCGCGCTC
AAGATTCTCGACATGACGCAGCATCCGGCGTTCATCAAGGGCTGGGAAGGTCTAGAGCTGTACGGCGT -continued

SEQUENCE LISTING

GGAGCTGGATTACGGAGGATGGATGTTTCAGGCTTCCATCTCGCCGGTGTGGGACACGGGCCTCGCCG
TGCTCGCGCTGCGCGCTGCGGGGCTTCCGGCCGATCACGACCGCTTGGTCAAGGCGGGCGAGTGGCTG
TTGGACCGGCAGATCACGGTTCCGGGCGACTGGGCGGTGAAGCGCCCGAACCTCAAGCCGGGCGGGTT
CGCGTTCCAGTTCGACAACGTGTACTACCCGGACGTGGACGACACGGCCGTCGTGGTGTGGGCGCTCA
ACACCCTGCGCTTGCCGGACGAGCGCCGCAGGCGGGACGCCATGACGAAGGGATTCCGCTGGATTGTC
GGCATGCAGAGCTCGAACGGCGGTTGGGGCGCCTACGACGTCGACAACACGAGCGATCTCCCGAACCA
CATCCCGTTCTGCGACTTCGGCGAAGTGACCGATCCGCCGTCAGAGGACGTCACCGCCCACGTGCTCG
AGTGTTTCGGCAGCTTCGGGTACGATGACGCCTGGAAGGTCATCCGGCGCGCGGTGGAATATCTCAAG
CGGGAGCAGAAGCCGGACGGCAGCTGGTTCGGTCGTTGGGGCGTCAATTACCTCTACGGCACGGGCGC
GGTGGTGTCGGCGCTGAAGGCGGTCGGGATCGACACGCGCGAGCCGTACATTCAAAAGGCGCTCGACT
GGGTCGAGCAGCATCAGAACCCGGACGGCGGCTGGGGCGAGGACTGCCGCTCGTACGAGGATCCGGCG
TACGCGGGTAAGGGCGCGAGCACCCCGTCGCAGACGGCCTGGGCGCTGATGGCGCTCATCGCGGGCGG
CAGGGCGGAGTCCGAGGCCGCGCGCCGCGGCGTGCAATACCTCGTGGAGACGCAGCGCCCGGACGGCG
GCTGGGATGAGCCGTACTACACCGGCACGGGCTTCCCAGGGGATTTCTACCTCGGCTACACCATGTAC
CGCCACGTGTTTCAACGCTCGCGCTCGGCCGCTACAAGCAGCCATCGAGCGCAGGTGA

SEQ ID NO: 16 (nucleotide sequence encoding Asa 215G2 SHC enzyme variant)
ATGGCTGAGCAGTTGGTGGAAGCTCCGGCCTACGCGCGGACGCTGGATCGCGCGGTGGAGTATCTCCT
CTCCTGCCAAAAGGACGAAGGCTACTGGTGGGGGCCGCTTCTGAGCAACGTCACGATGGAAGCGGAGT
ACGTCCTCTTGTGCCACATTCTCGATCGCGTCGATCGGGATCGCATGGAGAAGATCCGGCGGTACCTG
TTGCACGAGCAGCGCGAGGACGGCACGTGGGCCCTGTACCCGGGTGGGCCGCCGGACCTCGACACGAC
CATCGAGGCGTACGTCGCGCTCAAGTATATCGGCATGTCGCGCGACGAGGAGCCGATGCAGAAGGGGC
TCCGGTTCATTCAGAGCCAGGCCGGGATCGAGTCGTCGCGCGTGTTCACGCGGAGGTGGCTGGCGCTG
GTGGGAGAATATCCGTGGGAGAAGGTGCCCATGGTCCCGCCGGAGATCATGTTCCTCGGCAAGCGCAT
GCCGCTCAACATCTACGAGTTTGGCTCGTGGGCTCGGGCGACCGTCGTGGCGCTCTCGATTGTGATGA
GCCGCCAGCCGGTGTTCCCGCTGCCCGAGCGGGCGCGCGTGCCCGAGCTGTACGAGACCGACGTGCCT
CCGCGCCGGCGCGGTGCCAAGGGAGGGGGTGGGTGGATCTTCGACGCGCTCGACCGGGTGCTGCACGG
GTATCAGAAGCTGTCGGTGCACCCGTTCCGCCGCGCGGCCGAGATCCGCGCCTTGGACTGGTTGCTCG
AGCGCCAGGCCGGAGACGGCAGCTGGGGCGGGATTCAGCCGCCTTGGTTTTACGCGCTCATCGCGCTC
AAGATTCTCGACATGACGCAGCATCCGGCGTTCATCAAGGGCTGGGAAGGTCTAGAGCTGTACGGCGT
GGAGCTGGATTACGGAGGATGGATGTTTCAGGCTTCCATCTCGCCGGTGTGGGACACGGGCCTCGCCG
TGCTCGCGCTGCGCGCTGCGGGGCTTCCGGCCGATCACGACCGCTTGGTCAAGGCGGGCGAGTGCCTG
TTGGACCGGCAGATCACGGTTCCGGGCGACTGGGCGGTGAAGCGCCCGAACCTCAAGCCGGGCGGGTT
CGCGTTCCAGTTCGACAACGTGTACTACCCGGACGTGGACGACACGGCCGTCGTGGTGTGGGCGCTCA
ACACCCTGCGCTTGCCGGACGAGCGCCGCAGGCGGGACGCCATGACGAAGGGATTCCGCTGGATTGTC
GGCATGCAGAGCTCGAACGGCGGTTGGGGCGCCTACCACGTCGACAACACGAGCGATCTCCCGAACCA
CACCCCGTTGTGCGACTTCGGCGAAGTGACCGATCCGCCGTCAGAGGACGTCACCGCCCACGTGCTCG
AGTGTTTCGGCAGCTTCGGGTACGATGACGCCTGGAAGGTCATCCGGCGCGCGGTGGAATATCTCAAG
CGGGAGCAGAAGCCGGACGGCAGCTGGTTCGGTCGTTGGGGCGTCAATTACCTCTACGGCACGGGCGC
GGTGGTGTCGGCGCTGAAGGCGGTCGGGATCGACACGCGCGAGCCGTACATTCAAAAGGCGCTCGACT
GGGTCGAGCAGCATCAGAACCCGGACGGCGGCTGGGGCGAGGACTGCCGCTCGTACGAGGATCCGGCG
TACGCGGGTAAGGGCGCGAGCACCCCGTCGCAGACGGCCTGGGCGCTGATGGCGCTCATCGCGGGCGG
CAGGGCGGAGTCCGAGGCCGCGCGCCGCGGCGTGCAATACCTCGTGGAGACGCAGCGCCCGGACGGCG
GCTGGGATGAGCCGTACTACACCGGCACGGGCTTCCCAGGGGATTTCTACCTCGGCTACACCATGTAC
CGCCACGGTTTCCGACGCTCGCGCTCGGCCGCTACAAGCAAGCCACGAGCGCAGGTGA SEQ ID NO: 17 (amino add sequence of SHC enzyme variant #90C7)
MAEQLVEAPAYARTLDRAVEYLLSCQKDEGYWWGPLLSNVTMEAEYVLLCHILDRVDRDRMEKIRRYL
LHEQREDGTWALYPGGPPDLDATIEAYVALKYIGMSRDEEPMQKALRFIQSQGGIESSRVFTRRWLAL
VGEYPWEKVPMVPPEIMFLGKRMPLNIYEFGSWARATVVALSIVMSRQPVFPLPERARVPELYETDVP
PRRRGAKGGGGWIFDALDRVLHGYQKLSVHPFRRAAEIRALDWLLERQAGDGSWGGIQPPWFYALIAL
KILDMTQHPAFIKGWEGLELYGVELDYGGWMFQASISPVWDTGLAVLALRAAGLPADHDTLVKAGEWL
LDRQITVPGDWAVKRPNLKPGGFAFQFDNVYYPDVDDTAVVVWALNTLRLPDERRRRDAMTKGFRWIV
GMQSSNGGWGAYDVDNTSDLPNHTPFCDFGEVTDPPSEDVTAHVLECFGSFGYDDAWKVIRRAVEYLK
REQKPDGSWFGRWGVNYLYGTGAVVSALKAVGIDTREPYIQKALDWVEQHQNPDGGWGEDCRSYEDPA
YAGKGASTPSQTAWALMALIAGGRAESEAARRGVQYLVETQRPDGGWDEPYYTGTGFPGDFYLGYTMY
SHVFPTLALGRYKQAIERR SEQ ID NO: 18 (amino acid sequence of SHC enzyme variant #115A7)
MAEQLVEAPAYARTLDRAVEYLLSCQKDEGYWWGPLLSNVTMEAEYVLLCHTLDRVDRDRMERIRRYL
LHEQREDGTWALYPGGPPDLDTTIEAYVALKYIGMSRDEEPMQKALRFIQSQGGIESSRVFTRRWLAL
VGEYPWEKVPMVPPEIMFLGKRMPLNIYEFGSWARTTVVALSIVMSRQPVFPLPERARVPELYETDVP
PRRRGAKGGGGWIFDALDRVLHGYQKLSVHPFRRAAEIRALDWLLERQAGDGSWGGIQPPWFYALIAL
KILDKTQHPAFIKGWEGLELYGVELDYGGWMFQASISPVWDTGLAVLALRAAGLPADHDRLVKAGEWL
LDRQITVPGDWAVKRPNLKPGGFAFQFDNVYYPDVDDTAVVVWALNTLRLPDERRRRDAMTKGFRWIV
GMQSSNGGWGAYDVDNTSDLPNHTPFCDFGEVTDPPSEDVTAHVLECFGSFGYDDAWKVIRRAVEYLK
REQKPDGSWFGRWGVNYLYGTGAVVSALKAVGIDTREPYIQKALDWVEQHQNPDGGWGEDCRSYEDPA
YAGKGASTPSQTAWALMALIAGGRAESEAARRGVQYLVETQRPDGGWDEPYYTGTGFPGDFYLGYTMY
RHVFPTLALGRYKQAIERR SEQ ID NO-19 (amino acid sequence of wild-type TelSHC)
MPTSLATAIDPKQLQQAIRASQDFLFSQQYAEGYWWAELESNVTMTAEVILLHKTWGTEQRLPLAKAE
QYLRNHQRDHGGWELFYGDGGDLSTSVEAYMGLRLLGVPETDPALVKARQFILARGGISKTRIFTKLH
LALIGCYDWRGIPSLPPWIMLLPEGSPFTIYEMSSWARSSTVPLLIVMDRKPVYGMDPPITLDELYSE
GRANVVWELPRQGDWRDVFIGLDRVFKLFETLNIHPLREQGLKAAEEWVLERQEASGDWGGIIPAMLN
SLLALRALDYAVDDPIVQRGMAAVDRFAIETETEYRVQPCVSPVWDTALVMRAMVDSGVAPDHPALVK
AGEWLLSKQILDYGDWHIKNKKGRPGGWAFEFENRFYPDVDDTAVVMALHAVTLPNENLKRRAIERA -continued

SEQUENCE LISTING

VAWTASMQCRPGGWAAFDVDNDQDWLNGIPYGDLKAMIDPNTADVTARVLEMVGRCQLAFDRVALDRA
LAYLRNEQEPEGCWFGRWGVNYLNGTSGVLTALSLVAPRYDRWRIRRAAEWLMQCQNADGGWGETCWS
YHDPSLKGKGDSTASQTAWAIIGLLAAGDATGDYATEAIERGIAYLLETQRPDGTWHEDYFTGTGFPC
HFYLRYHYYQQHFPLTALGRYARWRNLLAT

SEQ ID NO: 20 (amino acid sequence of wild-type ApaSHC1)
MNMASRFSLKKILRSGSDTQGTNVSTLIQSGTSDIVRQKPAPQEPADLSALKAMGNSLTHTLSSACEW
LMKQQKPDGHWVGSVGSNASMEAEWCLALWFLGLEDHPLRPRLGKALLEMQRPDGSWGTYYGAGSGDI
NATVESYAALRSLGYAEDDPAVSKAAAWIISKGGLKNVRVFTRYWLALIGEWPWEKTPNLPPEIIWFP
DMFVFSIYNFAQWARATMMPLAILSARRPSRPLRPQDRLDALFPGGRANFDYELPTKEGRDVIADFFR
LADKGLHWLQSSFLKRAPSREAAIKYVLEWIIWHQDADGGWGGIQPPWVYGLMALHGEGYQFHHPVMA
KALDALNDPGWRHDKGDASWIQATNSPVWDTMLSLMALHDANAEERFTPEMDKALDWLLSRQVRVKGD
WSVKLPNTEPGGWAFEYANDRYPDTDDTAVALIAIASCRNRPEWQAKGVEEAIGRGVRWLVAMQSSCG
GWGAFDKDNNKSILAKIPFCDFGEALDPPSVDVTAHVLEAFGLLGLPRDLPCIQRGLAYIRKEQDPTG
PWFGRWGVNYLYGTGAVLPALAALGEDMTQPYISKACDWLINCQQENGGWGESCASYMEVSSIGHGAT
TPSQTAWALMGLIAANRPQDYEAIAKGCRYLIDLQEEDGSWNEEEFTGTGFPGYGVGQTIKLDDPAIS
KRLMQGAELSRAFMLRYDLYRQLFPIIALSRASRLIKLGN SEQ ID NO: 21 (amino acid sequence of a GmoSHC variant)
MSPADISTKSSSFQRLDNMLPEAVSSACDWLIDQQKPDGHWVGPLESNACMEAEWCLALWFLGQEDHP
LRPRLAQALLEMQREDGSWGIYVGADHGDINTTVEAYAALRSMGYAADMPIMAKSAAWIQQKGGLRNV
RVFTRYWLALIGEWPWDKTPNLPPEIIWLPDNFIFSIYNFAQWARATIMPLTILSARRPSRPLLPENR
LDGLFPEGRENFDYELPVKGEEDLWGRFFRAADKGLHSLQSFPVRRFVPREAAIRHVIEWIIRHQDAD
GGWGGIQPPWIYGLMALSVEGYPLHHPVLAKAMDALNDPGWRRDKGDASWIQASNSPVWDTMLAVLAL
HDAGAEDRYSPQMDKAIGWLLDRQVRVKGDWSIKLPDTEPGGWAFEYANDKYPDTDDTAVALIALAGC
RHRPEWRERDIEGAISRGVNWLLAMQSSSGGWGAFDKDNNRSILTKIPFCDFGEALDPPSVDVTAHVL
EAFGLLGISRNHPSVQKALAYIRSEQERNGAWFGRWGVNYVYGTGAVLPALAAIGEDMTQPYIVRACD
WLMSVQQENGGWGESCASYMDINAVGHGVATASQTAWALIGLLAAKRPKDREAIARGCQFLIERQEDG
SWTEEEYTGTGYPGYGVGQAIKLDDPSLPDRLLQGAELSRAFMLRYDLYRQYFPVMALSRARRMNKED
ASAAA SEQ ID NO: 22 (nucleotide sequence of SHC variant #90C7)
ATGGCTGAGCAGTTGGTGGAAGCTCCGGCCTACGCGCGGACGCTGGATCGCGCGGTGGAGTATCTCCT
CTCCTGCCAAAAGGACGAAGGCTACTGGTGGGGGCCGCTTCTGAGCAACGTCACGATGGAAGCGGAGT
ACGTCCTCTTGTGCCACATTCTCGATCGCGTCGATCGGGATCGCATGGAGAAGATCCGGCGGTACCTG
TTGCACGAGCAGCGCGAGGACGGCACGTGGGCCCTGTACCCGGGTGGGCCGCCGGACCTCGACGCGAC
CATCGAGGCGTACGTCGCGCTCAAGTATATCGGCATGTCGCGCGACGAGGAGCCGATGCAGAAGGCGC
TCCGGTTCATTCAGAGCCAGGGCGGATCGAGTCGTCGCGCGTGTTCACGCGGAGGTGGCTGGCGCTG
GTGGGAGAATATCCGTGGGAGAAGGTGCCCATGGTCCCGCCGGAGATCATGTTCCTCGGCAAGCGCAT
GCCGCTCAACATCTACGAGGTTGGCTCGTGGGCTCGGGCGACCGTCGTGGCGCTCTCGATTGTGATGA
GCCGCCAGCCGGTGTTCCCGCTGCCCGAGCGGGCGCGCGTGCCCGAGCTGTACGAGACCGACGTGCCT
CCGCGCCGGCGCGGTGCCAAGGGAGGGGGTGGGTGGATCTTCGACGCGCTCGACCGGGTGCTGCACGG
GTATCAGAAGCTGTCGGTGCACCCGTTCCGCCGCGCGGCCGAGATCCGCGCCTTGGACTGGTTGCTCG
AGCGCCAGGCCGGAGACGGCAGCTGGGGCGGGATTCAGCCGCCTTGGTTTTACGCGCTCATCGCGCTC
AAGATTCTCGACATGACGCAGCATCCGGCGTTCATCAAGGGCTGGGAAGGTCTAGAGCTGTACGGCGT
GGAGCTGGATTACGGAGGATGGATGTTTCAGGCTTCCATCTCGCCGGTGTGGGACACGGGCCTCGCCG
TGCTCGCGCTGCGCGCTGCGGGGCTTCCGGCCGATCACGACCGCTTGGTCAAGGCGGGCGAGTGGCTG
TTGGACCGGCAGATCACGGTTCCGGGCGACTGGGCGGTGAAGCGCCCGAACCTCAAGCCGGGCGGGTT
CGCGTTCCAGTTCGACAACGTGTACTACCCGGACGTGGACGACACGGCCGTCGTGGTGTGGGCGCTCA
ACACCCTGCGCTTGCCGGACGAGCGCCGCAGGCGGGACGCCATGACGAAGGGATTCCGCTGGATTGTC
GGCATGCAGAGCTCGAACGGCGGTTGGGGCGCCTACGACGTCGACAACACGAGCGATCTCCCGAACCA
CACCCCGTTCTGCGACTTCGGCGAAGTGACCGATCCGCCGTCAGAGGACGTCACCGCCCACGTGCTCG
AGTGTTTCGGCAGCTTCGGGTACGATGACGCCTGGAAGGTCATCCGGCGCGCGGTGGAATATCTCAAG
CGGGAGCAGAAGCCGGACGGCAGCTGGTTCGGTCGTTGGGGCGTCAATTACCTCTACGGCACGGGCGC
GGTGGTGTCGGCGCTGAAGGCGGTCGGGATCGACACGCGCGAGCCGTACATTCAAAAGGCGCTCGACT
GGGTCGAGCAGCATCAGAACCCGGACGGCGGCTGGGGCGAGGACTGCCGCTCGTACGAGGATCCGGCG
TACGCGGGTAAGGGCGCGAGCACCCCGTCGCAGACGGCCTGGGCGCTGATGGCGCTCATCGCGGGCGG
CAGGGCGGAGTCCGAGGCCGCGCGCCGCGGCGTGCAATACCTCGTGGAGACGCAGCGCCCGGACGGCG
GCTGGGATGAGCCGTACTACACCGGCACGGGCTTCCCAGGGGATTTCTACCTCGGCTACACCATGTAC
AGCCACGTGTTTCCGACGCCCGCGCTCGGCCGCTACAAGCAAGCCATCGAGCGCAGGTGA SEQ ID NO: 23 (nucleotide sequence of SHC variant #115A7)
ATGGCTGAGCAGTTGGTGGAAGCTCCGGCCTACGCGCGGACGCTGGATCGCGCGGTGGAGTATCTCCT
CTCCTGCCAAAAGGACGAAGGCTACTGGTGGGGGCCGCTTCTGAGCAACGTCACGATGGAAGCGGAGT
ACGTCCTCTTGTGCCACATTCTCGATCGCGTCGATCGGGATCGCATGGAGAAGATCCGGCGGTACCTG
TTGCACGAGCAGCGCGAGGACGGCACGTGGGCCCTGTACCCGGGTGGGCCGCCGGACCTCGACACGAC
CATCGAGGCGTACGTCGCGCTCAAGTATATCGGCATGTCGCGCGACGAGGAGCCGATGCAGAAGGCGC
TCCCGTTCATTCAGAGCCAGGGCGGATCGAGTCGTCGCGCGTGTTCACGCCGAGGTGGCTGGCGCTG
GTGGGAGAATATCCGTGGGAGAAGGTGCCCATGGTCCCGCCGGAGATCATCTTCCTCGGCAAGCGCAT
GCCGCTCAACATCTACGAGGTTTGGCTCGTGGGCTCGGACGACCGTCGTGGCGCTCTCGAGTGTGATA
GCCGCCAGCCGGTGTTCCCGCTGCCCGAGCGGGCGCGCGTGCCCGAGCTGTACGAGACCGACGTGCCT
CCGCGCCGGCGCGGTGCCAAGGGAGGGGGTGGGTGGATCTTCGACGCGCTCGACCGGGTGCTGCACGG
GTATCAGAAGCTGTCGGTGCACCCGTTCCGCCGCGCGGCCGAGATCCGCGCCTTGGACTGGTTGCTCG
AGCGCCAGGCCGGAGACGGCAGCTGGGGCGGGATTCAGCCGCCTTGGTTTTACGCGCTCATCGCGCTC
AAGATTCTCGACAAGACGCAGCATCCGGCGTTCATCAAGGGCTGGGAAGGTCTAGAGCTGTACGGCGT
GGAGCTGGATTACGGAGGATGGATGTTTCAGGCTTCCATCTCGCCGGTGTGGGACACGGGCCTCGCCG
TGCTCGCGCTGCGCGCTGCGGGGCTTCCGGCCGATCACGACCGCTTGGTCAAGGCGGGCGAGTGGCTG -continued

SEQUENCE LISTING

TTGGACCGGCAGATCACGGTTCCGGGCGACTGGGCGGTGAAGCGCCCGAACCTCAAGCCGGGCGGGTT
CGCGTTCCAGTTCGACAACGTGTACTACCCGGACGTGGACGACACGGCCGTCGTGGTGTGGGCGCTCA
ACACCCTGCGCTTGCCGGACGAGCGCCGCAGGCGGGACGCCATGACGAAGGGATTCCGCTGGATTGTC
GGCATGCAGAGCTCGAACGGCGGTTGGGGCGCCTACGACGTCGACAACACGAGCGATCTCCCGAACCA
CACCCCGTTCTGCGACTTCGGCGAAGTGACCGATCCGCCGTCAGAGGACGTCACCGCCCACGTGCTCG
AGTGTTTCGGCAGCTTCGGGTACGATGACGCCTGGAAGGTCATCCGGCGCGCGGTGGAATATCTCAAG
CGGGAGCAGAAGCCGGACGGCAGCTGGTTCGGTCGTTGGGGCGTCAATTACCTGTACGGCACGGGCGC
GGTGGTGTCGGCGCTGAAGGCGGTCGGGATCGACACGCGCGAGCCGTACATTCAAAAGGCGCTCGACT
GGGTCGAGCAGCATCAGAACCCGGACGGCGGCTGGGGCGAGGACTGCCGCTCGTACGAGGATCCGGCG
TACGCGGGTAAGGGCGCGAGCACCCCGTCGCAGACGGCCTGGGCGCTGATGGCGCTCATCGCGGGCGG
CAGGGCGGAGTTCCGAGGCCGCGCGCCGCGGCGTGCAATACCCGTGGAGACGCAGCGCCCGGACGGCG
GCTGGGATGAGCCGTACTACACCGGCACGGGCTTCCCAGGGGATTTCTACCTCGGCTACACCATGTAC
CGCCACGTGTTTCCGACGCTCGCGCTCGGCCGCTACAAGCAAGCCATCGAGCGCAGGTGA

The invention claimed is:

1. A method for making a compound of formula (I),

Formula (I)

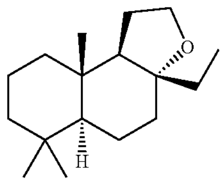

wherein the method comprises contacting a compound of formula (II) with a squalene-hopene cyclase (SHC) enzyme or enzyme variant, Formula (II)

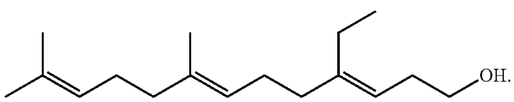

2. The method of claim 1, wherein the method comprises contacting a compound of formula (IIa) with the SHC enzyme or enzyme variant, Formula (IIa)

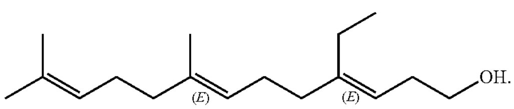

3. The method according to claim 1, wherein the method comprises contacting a composition comprising a compound of formula (IIa) and a compound of formula (IIb) with the SHC enzyme or enzyme variant, Formula (IIa)

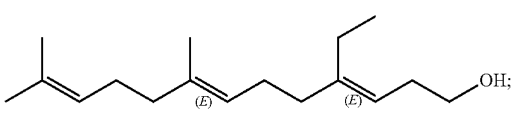

Formula (IIb)

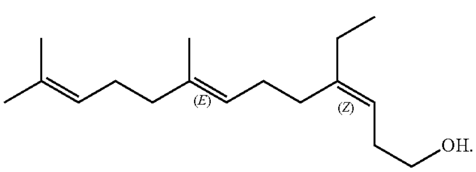

4. The method according to claim 3, wherein the weight ratio of the compound of formula (Ha) to the compound of formula (II*b*) ranges from about 5:1 to about 15:1.

5. The method according to claim 1, wherein a compound of formula (III) is made as a by-product, Formula (III)

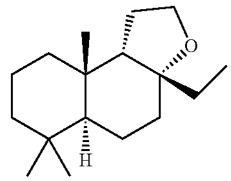

6. The method according to claim 1, wherein the SHC enzyme or enzyme variant is a wild-type SHC enzyme.

7. The method according to claim 1, wherein the SHC enzyme or enzyme variant is a SHC enzyme variant having an amino acid sequence having at least about 70.0% identity to a wild-type SHC enzyme amino acid sequence.

8. The method according to claim 7, wherein the SHC enzyme variant has amino acid alterations relative to the wild-type SHC enzyme at:

a) positions corresponding to positions 90 and 613 of SEQ ID NO: 1; and/or b) positions corresponding to positions 172 and 277 of SEQ ID NO: 1; and/or c) a position corresponding to position 557 of SEQ ID NO: 1 and at least one position corresponding to position 81, 431, or 613 of SEQ ID NO: 1; and/or d) positions corresponding to positions 557 and 431 of SEQ ID NO: 1; and/or e) positions corresponding to positions 557 and 613 of SEQ ID NO: 1; and/or f) positions corresponding to positions 81, 431, and 557 of SEQ ID NO: 1; and/or g) positions corresponding to positions 81, 557, and 613 of SEQ ID NO: 1; and/or h) positions corresponding to positions 132, 224, and 432 of SEQ ID NO: 1.

9. The method according to claim 1, wherein the SHC enzyme or enzyme variant and the compound of formula (II) are contacted at a temperature ranging from about 30° C. to about 50° C. and/or a pH ranging from about 5.0 to about 6.0.

10. The method according to claim 1, wherein the method further comprises purifying the compound of formula (I).

11. A composition comprising a compound of formula (I) and a compound of formula Formula (I)

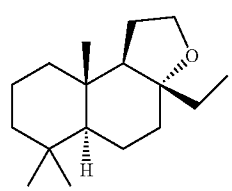

Formula (III)

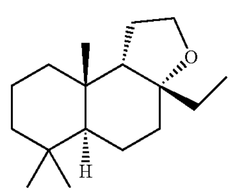

12. The composition according to claim 11, wherein the weight ratio of the compound of formula (I) to the compound of formula (III) ranges from about 60:40 to about 99:1.

13. A method of using the composition of claim 11 in or as a fragrance composition.

14. A consumer product comprising the composition of claim 11.

15. A method of using the composition of claim 12 in or as a fragrance composition.

16. A consumer product comprising the composition of claim 12.

* * * * *

SEQUENCE LISTING

<160> NUMBER OF SEQ ID NOS: 23

<210> SEQ ID NO 1
<211> LENGTH: 631
<212> TYPE: PRT
<213> ORGANISM: Alicyclobacillus acidocaldarius

<400> SEQUENCE: 1

Met Ala Glu Gln Leu Val Glu Ala Pro Ala Tyr Ala Arg Thr Leu Asp
1 5 10 15

Arg Ala Val Glu Tyr Leu Leu Ser Cys Gln Lys Asp Glu Gly Tyr Trp
20 25 30

Trp Gly Pro Leu Leu Ser Asn Val Thr Met Glu Ala Glu Tyr Val Leu
35 40 45

Leu Cys His Ile Leu Asp Arg Val Asp Arg Asp Arg Met Glu Lys Ile
50 55 60

Arg Arg Tyr Leu Leu His Glu Gln Arg Glu Asp Gly Thr Trp Ala Leu
65 70 75 80

Tyr Pro Gly Gly Pro Pro Asp Leu Asp Thr Thr Ile Glu Ala Tyr Val
85 90 95

Ala Leu Lys Tyr Ile Gly Met Ser Arg Asp Glu Glu Pro Met Gln Lys
100 105 110

Ala Leu Arg Phe Ile Gln Ser Gln Gly Gly Ile Glu Ser Ser Arg Val
115 120 125

Phe Thr Arg Met Trp Leu Ala Leu Val Gly Glu Tyr Pro Trp Glu Lys
130 135 140

Val Pro Met Val Pro Pro Glu Ile Met Phe Leu Gly Lys Arg Met Pro
145 150 155 160

Leu Asn Ile Tyr Glu Phe Gly Ser Trp Ala Arg Ala Thr Val Val Ala
165 170 175

Leu Ser Ile Val Met Ser Arg Gln Pro Val Phe Pro Leu Pro Glu Arg
180 185 190

Ala Arg Val Pro Glu Leu Tyr Glu Thr Asp Val Pro Pro Arg Arg Arg
195 200 205

Gly Ala Lys Gly Gly Gly Gly Trp Ile Phe Asp Ala Leu Asp Arg Ala
210 215 220

Leu His Gly Tyr Gln Lys Leu Ser Val His Pro Phe Arg Arg Ala Ala
225 230 235 240

Glu Ile Arg Ala Leu Asp Trp Leu Leu Glu Arg Gln Ala Gly Asp Gly
245 250 255

```
Ser Trp Gly Gly Ile Gln Pro Pro Trp Phe Tyr Ala Leu Ile Ala Leu
            260                 265                 270

Lys Ile Leu Asp Met Thr Gln His Pro Ala Phe Ile Lys Gly Trp Glu
        275                 280                 285

Gly Leu Glu Leu Tyr Gly Val Glu Leu Asp Tyr Gly Gly Trp Met Phe
    290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
        355                 360                 365

Asn Val Tyr Tyr Pro Asp Val Asp Asp Thr Ala Val Val Val Trp Ala
    370                 375                 380

Leu Asn Thr Leu Arg Leu Pro Asp Glu Arg Arg Arg Arg Asp Ala Met
385                 390                 395                 400

Thr Lys Gly Phe Arg Trp Ile Val Gly Met Gln Ser Ser Asn Gly Gly
                405                 410                 415

Trp Gly Ala Tyr Asp Val Asp Asn Thr Ser Asp Leu Pro Asn His Ile
            420                 425                 430

Pro Phe Cys Asp Phe Gly Glu Val Thr Asp Pro Pro Ser Glu Asp Val
        435                 440                 445

Thr Ala His Val Leu Glu Cys Phe Gly Ser Phe Gly Tyr Asp Asp Ala
    450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                485                 490                 495

Thr Gly Ala Val Val Ser Ala Leu Lys Ala Val Gly Ile Asp Thr Arg
            500                 505                 510

Glu Pro Tyr Ile Gln Lys Ala Leu Asp Trp Val Glu Gln His Gln Asn
        515                 520                 525

Pro Asp Gly Gly Trp Gly Glu Asp Cys Arg Ser Tyr Glu Asp Pro Ala
    530                 535                 540

Tyr Ala Gly Lys Gly Ala Ser Thr Pro Ser Gln Thr Ala Trp Ala Leu
545                 550                 555                 560

Met Ala Leu Ile Ala Gly Gly Arg Ala Glu Ser Glu Ala Ala Arg Arg
                565                 570                 575

Gly Val Gln Tyr Leu Val Glu Thr Gln Arg Pro Asp Gly Gly Trp Asp
            580                 585                 590

Glu Pro Tyr Tyr Thr Gly Thr Gly Phe Pro Gly Asp Phe Tyr Leu Gly
        595                 600                 605

Tyr Thr Met Tyr Arg His Val Phe Pro Thr Leu Ala Leu Gly Arg Tyr
    610                 615                 620

Lys Gln Ala Ile Glu Arg Arg
625                 630
```

<210> SEQ ID NO 2
<211> LENGTH: 631
<212> TYPE: PRT
<213> ORGANISM: Artificial Sequence
<220> FEATURE:
<223> OTHER INFORMATION: SHC enzyme variant #49

-continued

<400> SEQUENCE: 2

Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
            20                  25                  30

Trp Gly Pro Leu Leu Ser Asn Val Thr Met Glu Ala Glu Tyr Val Leu
        35                  40                  45

Leu Cys His Ile Leu Asp Arg Val Asp Arg Asp Arg Met Glu Lys Ile
    50                  55                  60

Arg Arg Tyr Leu Leu His Glu Gln Arg Glu Asp Gly Thr Trp Ala Leu
65                  70                  75                  80

Tyr Pro Gly Gly Pro Pro Asp Leu Asp Thr Thr Ile Glu Ala Tyr Val
                85                  90                  95

Ala Leu Lys Tyr Ile Gly Met Ser Arg Asp Glu Glu Pro Met Gln Lys
            100                 105                 110

Ala Leu Arg Phe Ile Gln Ser Gln Gly Gly Ile Glu Ser Ser Arg Val
        115                 120                 125

Phe Thr Arg Arg Trp Leu Ala Leu Val Gly Glu Tyr Pro Trp Glu Lys
    130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
                165                 170                 175

Leu Ser Ile Val Met Ser Arg Gln Pro Val Phe Pro Leu Pro Glu Arg
            180                 185                 190

Ala Arg Val Pro Glu Leu Tyr Glu Thr Asp Val Pro Pro Arg Arg Arg
        195                 200                 205

Gly Ala Lys Gly Gly Gly Gly Trp Ile Phe Asp Ala Leu Asp Arg Val
    210                 215                 220

Leu His Gly Tyr Gln Lys Leu Ser Val His Pro Phe Arg Arg Ala Ala
225                 230                 235                 240

Glu Ile Arg Ala Leu Asp Trp Leu Leu Glu Arg Gln Ala Gly Asp Gly
                245                 250                 255

Ser Trp Gly Gly Ile Gln Pro Pro Trp Phe Tyr Ala Leu Ile Ala Leu
            260                 265                 270

Lys Ile Leu Asp Met Thr Gln His Pro Ala Phe Ile Lys Gly Trp Glu
        275                 280                 285

Gly Leu Glu Leu Tyr Gly Val Glu Leu Asp Tyr Gly Gly Trp Met Phe
    290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
        355                 360                 365

Asn Val Tyr Tyr Pro Asp Val Asp Asp Thr Ala Val Val Val Trp Ala
    370                 375                 380

Leu Asn Thr Leu Arg Leu Pro Asp Glu Arg Arg Arg Arg Asp Ala Met
385                 390                 395                 400

Thr Lys Gly Phe Arg Trp Ile Val Gly Met Gln Ser Ser Asn Gly Gly

```
                405                 410                 415

Trp Gly Ala Tyr Asp Val Asp Asn Thr Ser Asp Leu Pro Asn Leu Thr
            420                 425                 430

Pro Phe Cys Asp Phe Gly Glu Val Thr Asp Pro Pro Ser Glu Asp Val
        435                 440                 445

Thr Ala His Val Leu Glu Cys Phe Gly Ser Phe Gly Tyr Asp Asp Ala
    450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                485                 490                 495

Thr Gly Ala Val Val Ser Ala Leu Lys Ala Val Gly Ile Asp Thr Arg
            500                 505                 510

Glu Pro Tyr Ile Gln Lys Ala Leu Asp Trp Val Glu Gln His Gln Asn
        515                 520                 525

Pro Asp Gly Gly Trp Gly Glu Asp Cys Arg Ser Tyr Glu Asp Pro Ala
    530                 535                 540

Tyr Ala Gly Lys Gly Ala Ser Thr Pro Ser Gln Thr Thr Trp Ala Leu
545                 550                 555                 560

Met Ala Leu Ile Ala Gly Gly Arg Ala Glu Ser Glu Ala Ala Arg Arg
                565                 570                 575

Gly Val Gln Tyr Leu Val Glu Thr Gln Arg Pro Asp Gly Gly Trp Asp
            580                 585                 590

Glu Pro Tyr Tyr Thr Gly Thr Gly Phe Pro Gly Asp Phe Tyr Leu Gly
        595                 600                 605

Tyr Thr Met Tyr Arg His Val Phe Pro Thr Leu Ala Leu Gly Arg Tyr
    610                 615                 620

Lys Gln Ala Ile Glu Arg Arg
625                 630


<210> SEQ ID NO 3
<211> LENGTH: 631
<212> TYPE: PRT
<213> ORGANISM: Artificial Sequence
<220> FEATURE:
<223> OTHER INFORMATION: SHC enzyme variant #65

<400> SEQUENCE: 3

Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
            20                  25                  30

Trp Gly Pro Leu Leu Ser Asn Val Thr Met Glu Ala Glu Tyr Val Leu
        35                  40                  45

Leu Cys His Ile Leu Asp Arg Val Asp Arg Asp Arg Met Glu Lys Ile
    50                  55                  60

Arg Arg Tyr Leu Leu His Glu Gln Arg Glu Asp Gly Thr Trp Ala Leu
65                  70                  75                  80

Tyr Pro Gly Gly Pro Pro Asp Leu Asp Thr Thr Ile Glu Ala Tyr Val
                85                  90                  95

Ala Leu Lys Tyr Ile Gly Met Ser Arg Asp Glu Glu Pro Met Gln Lys
            100                 105                 110

Ala Leu Arg Phe Ile Gln Ser Gln Gly Gly Ile Glu Ser Ser Arg Val
        115                 120                 125

Phe Thr Arg Arg Trp Leu Ala Leu Val Gly Glu Tyr Pro Trp Glu Lys
```

-continued

```
    130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
                165                 170                 175

Leu Ser Ile Val Met Ser Arg Gln Pro Val Phe Pro Leu Pro Glu Arg
            180                 185                 190

Ala Arg Val Pro Glu Leu Tyr Glu Thr Asp Val Pro Pro Arg Arg Arg
        195                 200                 205

Gly Ala Lys Gly Gly Gly Gly Trp Ile Phe Asp Ala Leu Asp Arg Val
    210                 215                 220

Leu His Gly Tyr Gln Lys Leu Ser Val His Pro Phe Arg Arg Ala Ala
225                 230                 235                 240

Glu Ile Arg Ala Leu Asp Trp Leu Leu Glu Arg Gln Ala Gly Asp Gly
                245                 250                 255

Ser Trp Gly Gly Ile Gln Pro Pro Trp Phe Tyr Ala Leu Ile Ala Leu
            260                 265                 270

Lys Ile Leu Asp Met Thr Gln His Pro Ala Phe Ile Lys Gly Trp Glu
        275                 280                 285

Gly Leu Glu Leu Tyr Gly Val Glu Leu Asp Tyr Gly Gly Trp Met Phe
    290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
        355                 360                 365

Asn Val Tyr Tyr Pro Asp Val Asp Asp Thr Ala Val Val Val Trp Ala
    370                 375                 380

Leu Asn Thr Leu Arg Leu Pro Asp Glu Arg Arg Arg Arg Asp Ala Met
385                 390                 395                 400

Thr Lys Gly Phe Arg Trp Ile Val Gly Met Gln Ser Ser Asn Gly Gly
                405                 410                 415

Trp Gly Ala Tyr Asp Val Asp Asn Thr Ser Asp Leu Pro Asn His Thr
            420                 425                 430

Pro Phe Cys Asp Phe Gly Glu Val Thr Asp Pro Pro Ser Glu Asp Val
        435                 440                 445

Thr Ala His Val Leu Glu Cys Phe Gly Ser Phe Gly Tyr Asp Asp Ala
    450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                485                 490                 495

Thr Gly Ala Val Val Ser Ala Leu Lys Ala Val Gly Ile Asp Thr Arg
            500                 505                 510

Glu Pro Tyr Ile Gln Lys Ala Leu Asp Trp Val Glu Gln His Gln Asn
        515                 520                 525

Pro Asp Gly Gly Trp Gly Glu Asp Cys Arg Ser Tyr Glu Asp Pro Ala
    530                 535                 540

Tyr Ala Gly Lys Gly Ala Ser Thr Pro Ser Gln Thr Thr Trp Ala Leu
545                 550                 555                 560
```

```
Met Ala Leu Ile Ala Gly Gly Arg Ala Glu Ser Glu Ala Ala Arg Arg
                565                 570                 575

Gly Val Gln Tyr Leu Val Glu Thr Gln Arg Pro Asp Gly Gly Trp Asp
            580                 585                 590

Glu Pro Tyr Tyr Thr Gly Thr Gly Phe Pro Gly Asp Phe Tyr Leu Gly
        595                 600                 605

Tyr Thr Met Tyr Ser His Val Phe Pro Thr Leu Ala Leu Gly Arg Tyr
    610                 615                 620

Lys Gln Ala Ile Glu Arg Arg
625                 630


<210> SEQ ID NO 4
<211> LENGTH: 631
<212> TYPE: PRT
<213> ORGANISM: Artificial Sequence
<220> FEATURE:
<223> OTHER INFORMATION: SHC enzyme variant #66

<400> SEQUENCE: 4

Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
            20                  25                  30

Trp Gly Pro Leu Leu Ser Asn Val Thr Met Glu Ala Glu Tyr Val Leu
        35                  40                  45

Leu Cys His Ile Leu Asp Arg Val Asp Arg Asp Arg Met Glu Lys Ile
    50                  55                  60

Arg Arg Tyr Leu Leu His Glu Gln Arg Glu Asp Gly Thr Trp Ala Leu
65                  70                  75                  80

His Pro Gly Gly Pro Pro Asp Leu Asp Thr Thr Ile Glu Ala Tyr Val
                85                  90                  95

Ala Leu Lys Tyr Ile Gly Met Ser Arg Asp Glu Glu Pro Met Gln Lys
            100                 105                 110

Ala Leu Arg Phe Ile Gln Ser Gln Gly Gly Ile Glu Ser Ser Arg Val
        115                 120                 125

Phe Thr Arg Arg Trp Leu Ala Leu Val Gly Glu Tyr Pro Trp Glu Lys
    130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
                165                 170                 175

Leu Ser Ile Val Met Ser Arg Gln Pro Val Phe Pro Leu Pro Glu Arg
            180                 185                 190

Ala Arg Val Pro Glu Leu Tyr Glu Thr Asp Val Pro Pro Arg Arg Arg
        195                 200                 205

Gly Ala Lys Gly Gly Gly Gly Trp Ile Phe Asp Ala Leu Asp Arg Val
    210                 215                 220

Leu His Gly Tyr Gln Lys Leu Ser Val His Pro Phe Arg Arg Ala Ala
225                 230                 235                 240

Glu Ile Arg Ala Leu Asp Trp Leu Leu Glu Arg Gln Ala Gly Asp Gly
                245                 250                 255

Ser Trp Gly Gly Ile Gln Pro Pro Trp Phe Tyr Ala Leu Ile Ala Leu
            260                 265                 270

Lys Ile Leu Asp Met Thr Gln His Pro Ala Phe Ile Lys Gly Trp Glu
        275                 280                 285
```

```
Gly Leu Glu Leu Tyr Gly Val Glu Leu Asp Tyr Gly Gly Trp Met Phe
    290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
        355                 360                 365

Asn Val Tyr Tyr Pro Asp Val Asp Asp Thr Ala Val Val Val Trp Ala
    370                 375                 380

Leu Asn Thr Leu Arg Leu Pro Asp Glu Arg Arg Arg Arg Asp Ala Met
385                 390                 395                 400

Thr Lys Gly Phe Arg Trp Ile Val Gly Met Gln Ser Ser Asn Gly Gly
                405                 410                 415

Trp Gly Ala Tyr Asp Val Asp Asn Thr Ser Asp Leu Pro Asn His Thr
            420                 425                 430

Pro Phe Cys Asp Phe Gly Glu Val Thr Asp Pro Pro Ser Glu Asp Val
        435                 440                 445

Thr Ala His Val Leu Glu Cys Phe Gly Ser Phe Gly Tyr Asp Asp Ala
    450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                485                 490                 495

Thr Gly Ala Val Val Ser Ala Leu Lys Ala Val Gly Ile Asp Thr Arg
            500                 505                 510

Glu Pro Tyr Ile Gln Lys Ala Leu Asp Trp Val Glu Gln His Gln Asn
        515                 520                 525

Pro Asp Gly Gly Trp Gly Glu Asp Cys Arg Ser Tyr Glu Asp Pro Ala
    530                 535                 540

Tyr Ala Gly Lys Gly Ala Ser Thr Pro Ser Gln Thr Thr Trp Ala Leu
545                 550                 555                 560

Met Ala Leu Ile Ala Gly Gly Arg Ala Glu Ser Glu Ala Ala Arg Arg
                565                 570                 575

Gly Val Gln Tyr Leu Val Glu Thr Gln Arg Pro Asp Gly Gly Trp Asp
            580                 585                 590

Glu Pro Tyr Tyr Thr Gly Thr Gly Phe Pro Gly Asp Phe Tyr Leu Gly
        595                 600                 605

Tyr Thr Met Tyr Ser His Val Phe Pro Thr Leu Ala Leu Gly Arg Tyr
    610                 615                 620

Lys Gln Ala Ile Glu Arg Arg
625                 630


<210> SEQ ID NO 5
<211> LENGTH: 631
<212> TYPE: PRT
<213> ORGANISM: Artificial Sequence
<220> FEATURE:
<223> OTHER INFORMATION: SHC enzyme variant #110B8

<400> SEQUENCE: 5

Met Ala Glu Gln Leu Val Glu Ala Pro Ala Tyr Ala Arg Thr Leu Asp
1               5                   10                  15
```

-continued

```
Arg Ala Val Glu Tyr Leu Leu Ser Cys Gln Lys Asp Glu Gly Tyr Trp
            20                  25                  30

Trp Gly Pro Leu Leu Ser Asn Val Thr Met Glu Ala Glu Tyr Val Leu
        35                  40                  45

Leu Cys His Ile Leu Asp Arg Val Asp Arg Asp Arg Met Glu Lys Ile
    50                  55                  60

Arg Arg Tyr Leu Leu His Glu Gln Arg Glu Asp Gly Thr Trp Ala Leu
65                  70                  75                  80

His Pro Gly Gly Pro Pro Asp Leu Asp Thr Thr Ile Glu Ala Tyr Val
                85                  90                  95

Ala Leu Lys Tyr Ile Gly Met Ser Arg Asp Glu Glu Pro Met Gln Lys
            100                 105                 110

Ala Leu Arg Phe Ile Gln Ser Gln Gly Gly Ile Glu Ser Ser Arg Val
        115                 120                 125

Phe Thr Arg Arg Trp Leu Ala Leu Val Gly Glu Tyr Pro Trp Glu Lys
    130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
                165                 170                 175

Leu Ser Ile Val Met Ser Arg Gln Pro Val Phe Pro Leu Pro Glu Arg
            180                 185                 190

Ala Arg Val Pro Glu Leu Tyr Glu Thr Asp Val Pro Pro Arg Arg Arg
        195                 200                 205

Gly Ala Lys Gly Gly Gly Gly Trp Ile Phe Asp Ala Leu Asp Arg Val
    210                 215                 220

Leu His Gly Tyr Gln Lys Leu Ser Val His Pro Phe Arg Arg Ala Ala
225                 230                 235                 240

Glu Ile Arg Ala Leu Asp Trp Leu Leu Glu Arg Gln Ala Gly Asp Gly
                245                 250                 255

Ser Trp Gly Gly Ile Gln Pro Pro Trp Phe Tyr Ala Leu Ile Ala Leu
            260                 265                 270

Lys Ile Leu Asp Met Thr Gln His Pro Ala Phe Ile Lys Gly Trp Glu
        275                 280                 285

Gly Leu Glu Leu Tyr Gly Val Glu Leu Asp Tyr Gly Gly Trp Met Phe
    290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
        355                 360                 365

Asn Val Tyr Tyr Pro Asp Val Asp Asp Thr Ala Val Val Val Trp Ala
    370                 375                 380

Leu Asn Thr Leu Arg Leu Pro Asp Glu Arg Arg Arg Arg Asp Ala Met
385                 390                 395                 400

Thr Lys Gly Phe Arg Trp Ile Val Gly Met Gln Ser Ser Asn Gly Gly
                405                 410                 415

Trp Gly Ala Tyr Asp Val Asp Asn Thr Ser Asp Leu Pro Asn Leu Thr
            420                 425                 430
```

-continued

```
Pro Phe Cys Asp Phe Gly Glu Val Thr Asp Pro Pro Ser Glu Asp Val
        435                 440                 445

Thr Ala His Val Leu Glu Cys Phe Gly Ser Phe Gly Tyr Asp Asp Ala
    450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                485                 490                 495

Thr Gly Ala Val Val Ser Ala Leu Lys Ala Val Gly Ile Asp Thr Arg
            500                 505                 510

Glu Pro Tyr Ile Gln Lys Ala Leu Asp Trp Val Glu Gln His Gln Asn
        515                 520                 525

Pro Asp Gly Gly Trp Gly Glu Asp Cys Arg Ser Tyr Glu Asp Pro Ala
    530                 535                 540

Tyr Ala Gly Lys Gly Ala Ser Thr Pro Ser Gln Thr Thr Trp Ala Leu
545                 550                 555                 560

Met Ala Leu Ile Ala Gly Gly Arg Ala Glu Ser Glu Ala Ala Arg Arg
                565                 570                 575

Gly Val Gln Tyr Leu Val Glu Thr Gln Arg Pro Asp Gly Gly Trp Asp
            580                 585                 590

Glu Pro Tyr Tyr Thr Gly Thr Gly Phe Pro Gly Asp Phe Tyr Leu Gly
        595                 600                 605

Tyr Thr Met Tyr Arg His Val Phe Pro Thr Leu Ala Leu Gly Arg Tyr
    610                 615                 620

Lys Gln Ala Ile Glu Arg Arg
625                 630
```

<210> SEQ ID NO 6
<211> LENGTH: 1896
<212> TYPE: DNA
<213> ORGANISM: Artificial Sequence
<220> FEATURE:
<223> OTHER INFORMATION: SHC enzyme variant #49

<400> SEQUENCE: 6

```
atggctgagc agttggtgga agctccggcc tacgcgcgga cgctggatcg cgcggtggag      60

tatctcctct cctgccaaaa ggacgaaggc tactggtggg ggccgcttct gagcaacgtc     120

acgatggaag cggagtacgt cctcttgtgc cacattctcg atcgcgtcga tcgggatcgc     180

atggagaaga tccggcggta cctgttgcac gagcagcgcg aggacggcac gtgggccctg     240

tacccgggtg ggccgccgga cctcgacacg accatcgagg cgtacgtcgc gctcaagtat     300

atcggcatgt cgcgcgacga ggagccgatg cagaaggcgc tccggttcat tcagagccag     360

ggcgggatcg agtcgtcgcg cgtgttcacg cggaggtggc tggcgctggt gggagaatat     420

ccgtgggaga aggtgcccat ggtcccgccg gagatcatgt tcctcggcaa gcgcatgccg     480

ctcaacatct acgagtttgg ctcgtgggct cgggcgaccg tcgtggcgct ctcgattgtg     540

atgagccgcc agccggtgtt cccgctgccc gagcgggcgc gcgtgcccga gctgtacgag     600

accgacgtgc ctccgcgccg gcgcggtgcc aagggagggg gtgggtggat cttcgacgcg     660

ctcgaccggg tgctgcacgg gtatcagaag ctgtcggtgc acccgttccg ccgcgcggcc     720

gagatccgcg ccttggactg gttgctcgag cgccaggccg gagacggcag ctggggcggg     780

attcagccgc cttggtttta cgcgctcatc gcgctcaaga ttctcgacat gacgcagcat     840

ccggcgttca tcaagggctg ggaaggtcta gagctgtacg gcgtggagct ggattacgga     900
```

-continued

```
ggatggatgt ttcaggcttc catctcgccg gtgtgggaca cgggcctcgc cgtgctcgcg    960
ctgcgcgctg cggggcttcc ggccgatcac gaccgcttgg tcaaggcggg cgagtggctg   1020
ttggaccggc agatcacggt tccgggcgac tgggcggtga agcgcccgaa cctcaagccg   1080
ggcgggttcg cgttccagtt cgacaacgtg tactacccgg acgtggacga cacggccgtc   1140
gtggtgtggg cgctcaacac cctgcgcttg ccggacgagc gccgcaggcg ggacgccatg   1200
acgaagggat tccgctggat tgtcggcatg cagagctcga acggcggttg ggcgcctac    1260
gacgtcgaca acacgagcga tctcccgaac ctcaccccgt tctgcgactt cggcgaagtg   1320
accgatccgc cgtcagagga cgtcaccgcc cacgtgctcg agtgtttcgg cagcttcggg   1380
tacgatgacg cctggaaggt catccggcgc gcggtggaat atctcaagcg ggagcagaag   1440
ccggacggca gctggttcgg tcgttggggc gtcaattacc tctacggcac gggcgcggtg   1500
gtgtcggcgc tgaaggcggt cgggatcgac acgcgcgagc cgtacattca aaaggcgctc   1560
gactgggtcg agcagcatca gaacccggac ggcggctggg gcgaggactg ccgctcgtac   1620
gaggatccgg cgtacgcggg taagggcgcg agcaccccgt cgcagacgac ctgggcgctg   1680
atggcgctca tcgcgggcgg cagggcggag tccgaggccg cgcgccgcgg cgtgcaatac   1740
ctcgtggaga cgcagcgccc ggacggcggc tgggatgagc cgtactacac cggcacgggc   1800
ttcccagggg atttctacct cggctacacc atgtaccgcc acgtgtttcc gacgctcgcg   1860
ctcggccgct acaagcaagc catcgagcgc aggtga                             1896
```

<210> SEQ ID NO 7
<211> LENGTH: 1896
<212> TYPE: DNA
<213> ORGANISM: Artificial Sequence
<220> FEATURE:
<223> OTHER INFORMATION: SHC enzyme variant #65

<400> SEQUENCE: 7

```
atggctgagc agttggtgga agctccggcc tacgcgcgga cgctggatcg cgcggtggag     60
tatctcctct cctgccaaaa ggacgaaggc tactggtggg ggccgcttct gagcaacgtc    120
acgatggaag cggagtacgt cctcttgtgc cacattctcg atcgcgtcga tcgggatcgc    180
atggagaaga tccggcggta cctgttgcac gagcagcgcg aggacggcac gtgggccctg    240
tacccgggtg ggccgccgga cctcgacacg accatcgagg cgtacgtcgc gctcaagtat    300
atcggcatgt cgcgcgacga ggagccgatg cagaaggcgc tccggttcat tcagagccag    360
ggcgggatcg agtcgtcgcg cgtgttcacg cggaggtggc tggcgctggt gggagaatat    420
ccgtgggaga aggtgcccat ggtcccgccg gagatcatgt tcctcggcaa gcgcatgccg    480
ctcaacatct acgagtttgg ctcgtgggct cgggcgaccg tcgtggcgct ctcgattgtg    540
atgagccgcc agccggtgtt cccgctgccc gagcgggcgc gcgtgcccga gctgtacgag    600
accgacgtgc ctccgcgccg gcgcggtgcc aagggagggg gtgggtggat cttcgacgcg    660
ctcgaccggg tgctgcacgg gtatcagaag ctgtcggtgc acccgttccg ccgcgcggcc    720
gagatccgcg ccttggactg gttgctcgag cgccaggccg gagacggcag ctggggcggg    780
attcagccgc cttggtttta cgcgctcatc gcgctcaaga ttctcgacat gacgcagcat    840
ccggcgttca tcaagggctg ggaaggtcta gagctgtacg gcgtggagct ggattacgga    900
ggatggatgt ttcaggcttc catctcgccg gtgtgggaca cgggcctcgc cgtgctcgcg    960
ctgcgcgctg cggggcttcc ggccgatcac gaccgcttgg tcaaggcggg cgagtggctg   1020
ttggaccggc agatcacggt tccgggcgac tgggcggtga agcgcccgaa cctcaagccg   1080
```

-continued ggcgggttcg cgttccagtt cgacaacgtg tactacccgg acgtggacga cacggccgtc 1140
gtggtgtggg cgctcaacac cctgcgcttg ccggacgagc gccgcaggcg ggacgccatg 1200
acgaagggat tccgctggat tgtcggcatg cagagctcga acggcggttg ggcgcctac 1260 gacgtcgaca acacgagcga tctcccgaac cacaccccgt tctgcgactt cggcgaagtg 1320
accgatccgc cgtcagagga cgtcaccgcc cacgtgctcg agtgtttcgg cagcttcggg 1380
tacgatgacg cctggaaggt catccggcgc gcggtggaat atctcaagcg ggagcagaag 1440
ccggacggca gctggttcgg tcgttggggc gtcaattacc tctacggcac gggcgcggtg 1500
gtgtcggcgc tgaaggcggt cgggatcgac acgcgcgagc cgtacattca aaaggcgctc 1560
gactgggtcg agcagcatca gaacccggac ggcggctggg gcgaggactg ccgctcgtac 1620
gaggatccgg cgtacgcggg taagggcgcg agcaccccgt cgcagacgac ctgggcgctg 1680
atggcgctca tcgcgggcgg cagggcggag tccgaggccg cgcgccgcgg cgtgcaatac 1740
ctcgtggaga cgcagcgccc ggacggcggc tgggatgagc cgtactacac cggcacgggc 1800
ttcccagggg atttctacct cggctacacc atgtacagcc acgtgtttcc gacgctcgcg 1860
ctcggccgct acaagcaagc catcgagcgc aggtga 1896

<210> SEQ ID NO 8
<211> LENGTH: 1896
<212> TYPE: DNA
<213> ORGANISM: Artificial Sequence
<220> FEATURE:
<223> OTHER INFORMATION: SHC enzyme variant #66

<400> SEQUENCE: 8
atggctgagc agttggtgga agctccggcc tacgcgcgga cgctggatcg cgcggtggag 60
tatctcctct cctgccaaaa ggacgaaggc tactggtggg ggccgcttct gagcaacgtc 120
acgatggaag cggagtacgt cctcttgtgc cacattctcg atcgcgtcga tcgggatcgc 180
atggagaaga tccggcggta cctgttgcac gagcagcgcg aggacggcac gtgggccctg 240
cacccgggtg ggccgccgga cctcgacacg accatcgagg cgtacgtcgc gctcaagtat 300
atcggcatgt cgcgcgacga ggagccgatg cagaaggcgc tccggttcat tcagagccag 360
ggcgggatcg agtcgtcgcg cgtgttcacg cggaggtggc tggcgctggt gggagaatat 420
ccgtgggaga aggtgcccat ggtcccgccg gagatcatgt tcctcggcaa gcgcatgccg 480
ctcaacatct acgagtttgg ctcgtgggct cgggcgaccg tcgtggcgct ctcgattgtg 540
atgagccgcc agccggtgtt cccgctgccc gagcgggcgc gcgtgcccga gctgtacgag 600
accgacgtgc ctccgcgccg gcgcggtgcc aagggagggg gtgggtggat cttcgacgcg 660
ctcgaccggg tgctgcacgg gtatcagaag ctgtcggtgc acccgttccg ccgcgcggcc 720
gagatccgcg ccttggactg gttgctcgag cgccaggccg gagacggcag ctggggcggg 780
attcagccgc cttggtttta cgcgctcatc gcgctcaaga ttctcgacat gacgcagcat 840
ccggcgttca tcaagggctg ggaaggtcta gagctgtacg gcgtggagct ggattacgga 900
ggatggatgt ttcaggcttc catctcgccg gtgtgggaca cgggcctcgc cgtgctcgcg 960
ctgcgcgctg cggggcttcc ggccgatcac gaccgcttgg tcaaggcggg cgagtggctg 1020
ttggaccggc agatcacggt tccgggcgac tgggcggtga agcgcccgaa cctcaagccg 1080
ggcgggttcg cgttccagtt cgacaacgtg tactacccgg acgtggacga cacggccgtc 1140
gtggtgtggg cgctcaacac cctgcgcttg ccggacgagc gccgcaggcg ggacgccatg 1200

```
acgaagggat tccgctggat tgtcggcatg cagagctcga acggcggttg ggcgcctac    1260

gacgtcgaca acacgagcga tctcccgaac cacaccccgt tctgcgactt cggcgaagtg   1320

accgatccgc cgtcagagga cgtcaccgcc cacgtgctcg agtgtttcgg cagcttcggg   1380

tacgatgacg cctggaaggt catccggcgc gcggtggaat atctcaagcg ggagcagaag   1440

ccggacggca gctggttcgg tcgttggggc gtcaattacc tctacggcac gggcgcggtg   1500

gtgtcggcgc tgaaggcggt cgggatcgac acgcgcgagc cgtacattca aaaggcgctc   1560

gactgggtcg agcagcatca gaacccggac ggcggctggg gcgaggactg ccgctcgtac   1620

gaggatccgg cgtacgcggg taagggcgcg agcaccccgt cgcagacgac ctgggcgctg   1680

atggcgctca tcgcgggcgg cagggcggag tccgaggccg cgcgccgcgg cgtgcaatac   1740

ctcgtggaga cgcagcgccc ggacggcggc tgggatgagc cgtactacac cggcacgggc   1800

ttcccagggg atttctacct cggctacacc atgtacagcc acgtgtttcc gacgctcgcg   1860

ctcggccgct acaagcaagc catcgagcgc aggtga                             1896
```

<210> SEQ ID NO 9
<211> LENGTH: 1896
<212> TYPE: DNA
<213> ORGANISM: Artificial Sequence
<220> FEATURE:
<223> OTHER INFORMATION: SHC enzyme variant #110B8

<400> SEQUENCE: 9

```
atggctgagc agttggtgga agctccggcc tacgcgcgga cgctggatcg cgcggtggag     60

tatctcctct cctgccaaaa ggacgaaggc tactggtggg ggccgcttct gagcaacgtc    120

acgatggaag cggagtacgt cctcttgtgc cacattctcg atcgcgtcga tcgggatcgc    180

atggagaaga tccggcggta cctgttgcac gagcagcgcg aggacggcac gtgggccctg    240

cacccgggtg ggccgccgga cctcgacacg accatcgagg cgtacgtcgc gctcaagtat    300

atcggcatgt cgcgcgacga ggagccgatg cagaaggcgc tccggttcat tcagagccag    360

ggcgggatcg agtcgtcgcg cgtgttcacg cggaggtggc tggcgctggt gggagaatat    420

ccgtgggaga aggtgcccat ggtcccgccg gagatcatgt tcctcggcaa gcgcatgccg    480

ctcaacatct acgagtttgg ctcgtgggct cgggcgaccg tcgtggcgct ctcgattgtg    540

atgagccgcc agccggtgtt cccgctgccc gagcgggcgc gcgtgcccga gctgtacgag    600

accgacgtgc ctccgcgccg gcgcggtgcc aagggagggg gtgggtggat cttcgacgcg    660

ctcgaccggg tgctgcacgg gtatcagaag ctgtcggtgc acccgttccg ccgcgcggcc    720

gagatccgcg ccttggactg gttgctcgag cgccaggccg gagacggcag ctggggcggg    780

attcagccgc cttggtttta cgcgctcatc gcgctcaaga ttctcgacat gacgcagcat    840

ccggcgttca tcaagggctg ggaaggtcta gagctgtacg gcgtggagct ggattacgga    900

ggatggatgt ttcaggcttc catctcgccg gtgtgggaca cgggcctcgc cgtgctcgcg    960

ctgcgcgctg cggggcttcc ggccgatcac gaccgcttgg tcaaggcggg cgagtggctg   1020

ttggaccggc agatcacggt tccgggcgac tgggcggtga agcgcccgaa cctcaagccg   1080

ggcgggttcg cgttccagtt cgacaacgtg tactacccgg acgtggacga cacggccgtc   1140

gtggtgtggg cgctcaacac cctgcgcttg ccggacgagc gccgcaggcg ggacgccatg   1200

acgaagggat tccgctggat tgtcggcatg cagagctcga acggcggttg ggcgcctac    1260

gacgtcgaca acacgagcga tctcccgaac ctcaccccgt tctgcgactt cggcgaagtg   1320

accgatccgc cgtcagagga cgtcaccgcc cacgtgctcg agtgtttcgg cagcttcggg   1380
```

```
tacgatgacg cctggaaggt catccggcgc gcggtggaat atctcaagcg ggagcagaag   1440

ccggacggca gctggttcgg tcgttggggc gtcaattacc tctacggcac gggcgcggtg   1500

gtgtcggcgc tgaaggcggt cgggatcgac acgcgcgagc cgtacattca aaaggcgctc   1560

gactgggtcg agcagcatca gaacccggac ggcggctggg gcgaggactg ccgctcgtac   1620

gaggatccgg cgtacgcggg taagggcgcg agcaccccgt cgcagacgac ctgggcgctg   1680

atggcgctca tcgcgggcgg cagggcggag tccgaggccg cgcgccgcgg cgtgcaatac   1740

ctcgtggaga cgcagcgccc ggacggcggc tgggatgagc cgtactacac cggcacgggc   1800

ttcccagggg atttctacct cggctacacc atgtaccgcc acgtgtttcc gacgctcgcg   1860

ctcggccgct acaagcaagc catcgagcgc aggtga                               1896
```

```
<210> SEQ ID NO 10
<211> LENGTH: 631
<212> TYPE: PRT
<213> ORGANISM: Artificial Sequence
<220> FEATURE:
<223> OTHER INFORMATION: 215G2 SHC enzyme variant

<400> SEQUENCE: 10

Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
            20                  25                  30

Trp Gly Pro Leu Leu Ser Asn Val Thr Met Glu Ala Glu Tyr Val Leu
        35                  40                  45

Leu Cys His Ile Leu Asp Arg Val Asp Arg Asp Arg Met Glu Lys Ile
    50                  55                  60

Arg Arg Tyr Leu Leu His Glu Gln Arg Glu Asp Gly Thr Trp Ala Leu
65                  70                  75                  80

Tyr Pro Gly Gly Pro Pro Asp Leu Asp Thr Thr Ile Glu Ala Tyr Val
                85                  90                  95

Ala Leu Lys Tyr Ile Gly Met Ser Arg Asp Glu Glu Pro Met Gln Lys
            100                 105                 110

Ala Leu Arg Phe Ile Gln Ser Gln Gly Gly Ile Glu Ser Ser Arg Val
        115                 120                 125

Phe Thr Arg Arg Trp Leu Ala Leu Val Gly Glu Tyr Pro Trp Glu Lys
    130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
                165                 170                 175

Leu Ser Ile Val Met Ser Arg Gln Pro Val Phe Pro Leu Pro Glu Arg
            180                 185                 190

Ala Arg Val Pro Glu Leu Tyr Glu Thr Asp Val Pro Pro Arg Arg Arg
        195                 200                 205

Gly Ala Lys Gly Gly Gly Gly Trp Ile Phe Asp Ala Leu Asp Arg Val
    210                 215                 220

Leu His Gly Tyr Gln Lys Leu Ser Val His Pro Phe Arg Arg Ala Ala
225                 230                 235                 240

Glu Ile Arg Ala Leu Asp Trp Leu Leu Glu Arg Gln Ala Gly Asp Gly
                245                 250                 255

Ser Trp Gly Gly Ile Gln Pro Pro Trp Phe Tyr Ala Leu Ile Ala Leu
            260                 265                 270
```

-continued

```
Lys Ile Leu Asp Met Thr Gln His Pro Ala Phe Ile Lys Gly Trp Glu
        275                 280                 285

Gly Leu Glu Leu Tyr Gly Val Glu Leu Asp Tyr Gly Gly Trp Met Phe
    290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
        355                 360                 365

Asn Val Tyr Tyr Pro Asp Val Asp Asp Thr Ala Val Val Val Trp Ala
    370                 375                 380

Leu Asn Thr Leu Arg Leu Pro Asp Glu Arg Arg Arg Arg Asp Ala Met
385                 390                 395                 400

Thr Lys Gly Phe Arg Trp Ile Val Gly Met Gln Ser Ser Asn Gly Gly
                405                 410                 415

Trp Gly Ala Tyr Asp Val Asp Asn Thr Ser Asp Leu Pro Asn His Thr
            420                 425                 430

Pro Phe Cys Asp Phe Gly Glu Val Thr Asp Pro Pro Ser Glu Asp Val
        435                 440                 445

Thr Ala His Val Leu Glu Cys Phe Gly Ser Phe Gly Tyr Asp Asp Ala
    450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                485                 490                 495

Thr Gly Ala Val Val Ser Ala Leu Lys Ala Val Gly Ile Asp Thr Arg
            500                 505                 510

Glu Pro Tyr Ile Gln Lys Ala Leu Asp Trp Val Glu Gln His Gln Asn
        515                 520                 525

Pro Asp Gly Gly Trp Gly Glu Asp Cys Arg Ser Tyr Glu Asp Pro Ala
    530                 535                 540

Tyr Ala Gly Lys Gly Ala Ser Thr Pro Ser Gln Thr Ala Trp Ala Leu
545                 550                 555                 560

Met Ala Leu Ile Ala Gly Gly Arg Ala Glu Ser Glu Ala Ala Arg Arg
                565                 570                 575

Gly Val Gln Tyr Leu Val Glu Thr Gln Arg Pro Asp Gly Gly Trp Asp
            580                 585                 590

Glu Pro Tyr Tyr Thr Gly Thr Gly Phe Pro Gly Asp Phe Tyr Leu Gly
        595                 600                 605

Tyr Thr Met Tyr Arg His Val Phe Pro Thr Leu Ala Leu Gly Arg Tyr
    610                 615                 620

Lys Gln Ala Ile Glu Arg Arg
625                 630
```

<210> SEQ ID NO 11
<211> LENGTH: 608
<212> TYPE: PRT
<213> ORGANISM: Zymomonas mobilis

<400> SEQUENCE: 11

```
Met Gly Ile Asp Arg Met Asn Ser Leu Ser Arg Leu Leu Met Lys Lys
```

-continued

```
1               5                   10                  15

Ile Phe Gly Ala Glu Lys Thr Ser Tyr Lys Pro Ala Ser Asp Thr Ile
            20                  25                  30

Ile Gly Thr Asp Thr Leu Lys Arg Pro Asn Arg Arg Pro Glu Pro Thr
        35                  40                  45

Ala Lys Val Asp Lys Thr Ile Phe Lys Thr Met Gly Asn Ser Leu Asn
    50                  55                  60

Asn Thr Leu Val Ser Ala Cys Asp Trp Leu Ile Gly Gln Gln Lys Pro
65                  70                  75                  80

Asp Gly His Trp Val Gly Ala Val Glu Ser Asn Ala Ser Met Glu Ala
                85                  90                  95

Glu Trp Cys Leu Ala Leu Trp Phe Leu Gly Leu Glu Asp His Pro Leu
            100                 105                 110

Arg Pro Arg Leu Gly Asn Ala Leu Leu Glu Met Gln Arg Glu Asp Gly
        115                 120                 125

Ser Trp Gly Val Tyr Phe Gly Ala Gly Asn Gly Asp Ile Asn Ala Thr
    130                 135                 140

Val Glu Ala Tyr Ala Ala Leu Arg Ser Leu Gly Tyr Ser Ala Asp Asn
145                 150                 155                 160

Pro Val Leu Lys Lys Ala Ala Ala Trp Ile Ala Glu Lys Gly Gly Leu
                165                 170                 175

Lys Asn Ile Arg Val Phe Thr Arg Tyr Trp Leu Ala Leu Ile Gly Glu
            180                 185                 190

Trp Pro Trp Glu Lys Thr Pro Asn Leu Pro Pro Glu Ile Ile Trp Phe
        195                 200                 205

Pro Asp Asn Phe Val Phe Ser Ile Tyr Asn Phe Ala Gln Trp Ala Arg
    210                 215                 220

Ala Thr Met Val Pro Ile Ala Ile Leu Ser Ala Arg Arg Pro Ser Arg
225                 230                 235                 240

Pro Leu Arg Pro Gln Asp Arg Leu Asp Glu Leu Phe Pro Glu Gly Arg
                245                 250                 255

Ala Arg Phe Asp Tyr Glu Leu Pro Lys Lys Glu Gly Ile Asp Leu Trp
            260                 265                 270

Ser Gln Phe Phe Arg Thr Thr Asp Arg Gly Leu His Trp Val Gln Ser
        275                 280                 285

Asn Leu Leu Lys Arg Asn Ser Leu Arg Glu Ala Ala Ile Arg His Val
    290                 295                 300

Leu Glu Trp Ile Ile Arg His Gln Asp Ala Asp Gly Gly Trp Gly Gly
305                 310                 315                 320

Ile Gln Pro Pro Trp Val Tyr Gly Leu Met Ala Leu His Gly Glu Gly
                325                 330                 335

Tyr Gln Leu Tyr His Pro Val Met Ala Lys Ala Leu Ser Ala Leu Asp
            340                 345                 350

Asp Pro Gly Trp Arg His Asp Arg Gly Glu Ser Ser Trp Ile Gln Ala
        355                 360                 365

Thr Asn Ser Pro Val Trp Asp Thr Met Leu Ala Leu Met Ala Leu Lys
    370                 375                 380

Asp Ala Lys Ala Glu Asp Arg Phe Thr Pro Glu Met Asp Lys Ala Ala
385                 390                 395                 400

Asp Trp Leu Leu Ala Arg Gln Val Lys Val Lys Gly Asp Trp Ser Ile
                405                 410                 415

Lys Leu Pro Asp Val Glu Pro Gly Gly Trp Ala Phe Glu Tyr Ala Asn
            420                 425                 430
```

-continued

```
Asp Arg Tyr Pro Asp Thr Asp Asp Thr Ala Val Ala Leu Ile Ala Leu
        435                 440                 445

Ser Ser Tyr Arg Asp Lys Glu Glu Trp Gln Lys Lys Gly Val Glu Asp
    450                 455                 460

Ala Ile Thr Arg Gly Val Asn Trp Leu Ile Ala Met Gln Ser Glu Cys
465                 470                 475                 480

Gly Gly Trp Gly Ala Phe Asp Lys Asp Asn Asn Arg Ser Ile Leu Ser
                485                 490                 495

Lys Ile Pro Phe Cys Asp Phe Gly Glu Ser Ile Asp Pro Pro Ser Val
            500                 505                 510

Asp Val Thr Ala His Val Leu Glu Ala Phe Gly Thr Leu Gly Leu Ser
        515                 520                 525

Arg Asp Met Pro Val Ile Gln Lys Ala Ile Asp Tyr Val Arg Ser Glu
    530                 535                 540

Gln Glu Ala Glu Gly Ala Trp Phe Gly Arg Trp Gly Val Asn Tyr Ile
545                 550                 555                 560

Tyr Gly Thr Gly Ala Val Leu Pro Ala Leu Ala Ala Ile Gly Glu Asp
                565                 570                 575

Met Thr Gln Pro Tyr Ile Thr Lys Ala Cys Asp Trp Leu Val Ala His
            580                 585                 590

Gln Gln Glu Asp Gly Gly Trp Gly Glu Ser Cys Ser Ser Tyr Met Glu
        595                 600                 605


<210> SEQ ID NO 12
<211> LENGTH: 658
<212> TYPE: PRT
<213> ORGANISM: Zymomonas mobilis

<400> SEQUENCE: 12

Met Thr Val Ser Thr Ser Ser Ala Phe His His Ser Pro Leu Ser Asp
1               5                   10                  15

Asp Val Glu Pro Ile Ile Gln Lys Ala Thr Arg Ala Leu Leu Glu Lys
            20                  25                  30

Gln Gln Gln Asp Gly His Trp Val Phe Glu Leu Glu Ala Asp Ala Thr
        35                  40                  45

Ile Pro Ala Glu Tyr Ile Leu Leu Lys His Tyr Leu Gly Glu Pro Glu
    50                  55                  60

Asp Leu Glu Ile Glu Ala Lys Ile Gly Arg Tyr Leu Arg Arg Ile Gln
65                  70                  75                  80

Gly Glu His Gly Gly Trp Ser Leu Phe Tyr Gly Gly Asp Leu Asp Leu
                85                  90                  95

Ser Ala Thr Val Lys Ala Tyr Phe Ala Leu Lys Met Ile Gly Asp Ser
            100                 105                 110

Pro Asp Ala Pro His Met Leu Arg Ala Arg Asn Glu Ile Leu Ala Arg
        115                 120                 125

Gly Gly Ala Met Arg Ala Asn Val Phe Thr Arg Ile Gln Leu Ala Leu
    130                 135                 140

Phe Gly Ala Met Ser Trp Glu His Val Pro Gln Met Pro Val Glu Leu
145                 150                 155                 160

Met Leu Met Pro Glu Trp Phe Pro Val His Ile Asn Lys Met Ala Tyr
                165                 170                 175

Trp Ala Arg Thr Val Leu Val Pro Leu Leu Val Leu Gln Ala Leu Lys
            180                 185                 190

Pro Val Ala Arg Asn Arg Arg Gly Ile Leu Val Asp Glu Leu Phe Val
```

-continued

```
        195                 200                 205

Pro Asp Val Leu Pro Thr Leu Gln Glu Ser Gly Asp Pro Ile Trp Arg
    210                 215                 220

Arg Phe Phe Ser Ala Leu Asp Lys Val Leu His Lys Val Glu Pro Tyr
225                 230                 235                 240

Trp Pro Lys Asn Met Arg Ala Lys Ala Ile His Ser Cys Val His Phe
                245                 250                 255

Val Thr Glu Arg Leu Asn Gly Glu Asp Gly Leu Gly Ala Ile Tyr Pro
            260                 265                 270

Ala Ile Ala Asn Ser Val Met Met Tyr Asp Ala Leu Gly Tyr Pro Glu
        275                 280                 285

Asn His Pro Glu Arg Ala Ile Ala Arg Arg Ala Val Glu Lys Leu Met
    290                 295                 300

Val Leu Asp Gly Thr Glu Asp Gln Gly Asp Lys Glu Val Tyr Cys Gln
305                 310                 315                 320

Pro Cys Leu Ser Pro Ile Trp Asp Thr Ala Leu Val Ala His Ala Met
                325                 330                 335

Leu Glu Val Gly Gly Asp Glu Ala Glu Lys Ser Ala Ile Ser Ala Leu
            340                 345                 350

Ser Trp Leu Lys Pro Gln Gln Ile Leu Asp Val Lys Gly Asp Trp Ala
        355                 360                 365

Trp Arg Arg Pro Asp Leu Arg Pro Gly Gly Trp Ala Phe Gln Tyr Arg
    370                 375                 380

Asn Asp Tyr Tyr Pro Asp Val Asp Asp Thr Ala Val Val Thr Met Ala
385                 390                 395                 400

Met Asp Arg Ala Ala Lys Leu Ser Asp Leu His Asp Asp Phe Glu Glu
                405                 410                 415

Ser Lys Ala Arg Ala Met Glu Trp Thr Ile Gly Met Gln Ser Asp Asn
            420                 425                 430

Gly Gly Trp Gly Ala Phe Asp Ala Asn Asn Ser Tyr Thr Tyr Leu Asn
        435                 440                 445

Asn Ile Pro Phe Ala Asp His Gly Ala Leu Leu Asp Pro Pro Thr Val
    450                 455                 460

Asp Val Ser Ala Arg Cys Val Ser Met Met Ala Gln Ala Gly Ile Ser
465                 470                 475                 480

Ile Thr Asp Pro Lys Met Lys Ala Ala Val Asp Tyr Leu Leu Lys Glu
                485                 490                 495

Gln Glu Glu Asp Gly Ser Trp Phe Gly Arg Trp Gly Val Asn Tyr Ile
            500                 505                 510

Tyr Gly Thr Trp Ser Ala Leu Cys Ala Leu Asn Val Ala Ala Leu Pro
        515                 520                 525

His Asp His Leu Ala Val Gln Lys Ala Val Ala Trp Leu Lys Thr Ile
    530                 535                 540

Gln Asn Glu Asp Gly Gly Trp Gly Glu Asn Cys Asp Ser Tyr Ala Leu
545                 550                 555                 560

Asp Tyr Ser Gly Tyr Glu Pro Met Asp Ser Thr Ala Ser Gln Thr Ala
                565                 570                 575

Trp Ala Leu Leu Gly Leu Met Ala Val Gly Glu Ala Asn Ser Glu Ala
            580                 585                 590

Val Thr Lys Gly Ile Asn Trp Leu Ala Gln Asn Gln Asp Glu Glu Gly
        595                 600                 605

Leu Trp Lys Glu Asp Tyr Tyr Ser Gly Gly Gly Phe Pro Arg Val Phe
    610                 615                 620
```

```
Tyr Leu Arg Tyr His Gly Tyr Ser Lys Tyr Phe Pro Leu Trp Ala Leu
625                 630                 635                 640

Ala Arg Tyr Arg Asn Leu Lys Lys Ala Asn Gln Pro Ile Val His Tyr
                645                 650                 655

Gly Met


<210> SEQ ID NO 13
<211> LENGTH: 684
<212> TYPE: PRT
<213> ORGANISM: Bradyrhizobium japonicum

<400> SEQUENCE: 13

Met Thr Val Thr Ser Ser Ala Ser Ala Arg Ala Thr Arg Asp Pro Gly
1               5                   10                  15

Asn Tyr Gln Thr Ala Leu Gln Ser Thr Val Arg Ala Ala Ala Asp Trp
            20                  25                  30

Leu Ile Ala Asn Gln Lys Pro Asp Gly His Trp Val Gly Arg Ala Glu
        35                  40                  45

Ser Asn Ala Cys Met Glu Ala Gln Trp Cys Leu Ala Leu Trp Phe Met
    50                  55                  60

Gly Leu Glu Asp His Pro Leu Arg Lys Arg Leu Gly Gln Ser Leu Leu
65                  70                  75                  80

Asp Ser Gln Arg Pro Asp Gly Ala Trp Gln Val Tyr Phe Gly Ala Pro
                85                  90                  95

Asn Gly Asp Ile Asn Ala Thr Val Glu Ala Tyr Ala Ala Leu Arg Ser
            100                 105                 110

Leu Gly Phe Arg Asp Asp Glu Pro Ala Val Arg Arg Ala Arg Glu Trp
        115                 120                 125

Ile Glu Ala Lys Gly Gly Leu Arg Asn Ile Arg Val Phe Thr Arg Tyr
    130                 135                 140

Trp Leu Ala Leu Ile Gly Glu Trp Pro Trp Glu Lys Thr Pro Asn Ile
145                 150                 155                 160

Pro Pro Glu Val Ile Trp Phe Pro Leu Trp Phe Pro Phe Ser Ile Tyr
                165                 170                 175

Asn Phe Ala Gln Trp Ala Arg Ala Thr Leu Met Pro Ile Ala Val Leu
            180                 185                 190

Ser Ala Arg Arg Pro Ser Arg Pro Leu Pro Pro Glu Asn Arg Leu Asp
        195                 200                 205

Ala Leu Phe Pro His Gly Arg Lys Ala Phe Asp Tyr Glu Leu Pro Val
    210                 215                 220

Lys Ala Gly Ala Gly Gly Trp Asp Arg Phe Phe Arg Gly Ala Asp Lys
225                 230                 235                 240

Val Leu His Lys Leu Gln Asn Leu Gly Asn Arg Leu Asn Leu Gly Leu
                245                 250                 255

Phe Arg Pro Ala Ala Thr Ser Arg Val Leu Glu Trp Met Ile Arg His
            260                 265                 270

Gln Asp Phe Asp Gly Ala Trp Gly Gly Ile Gln Pro Pro Trp Ile Tyr
        275                 280                 285

Gly Leu Met Ala Leu Tyr Ala Glu Gly Tyr Pro Leu Asn His Pro Val
    290                 295                 300

Leu Ala Lys Gly Leu Asp Ala Leu Asn Asp Pro Gly Trp Arg Val Asp
305                 310                 315                 320

Val Gly Asp Ala Thr Tyr Ile Gln Ala Thr Asn Ser Pro Val Trp Asp
                325                 330                 335
```

```
Thr Ile Leu Thr Leu Leu Ala Phe Asp Asp Ala Gly Val Leu Gly Asp
            340                 345                 350

Tyr Pro Glu Ala Val Asp Lys Ala Val Asp Trp Val Leu Gln Arg Gln
        355                 360                 365

Val Arg Val Pro Gly Asp Trp Ser Met Lys Leu Pro His Val Lys Pro
    370                 375                 380

Gly Gly Trp Ala Phe Glu Tyr Ala Asn Asn Tyr Tyr Pro Asp Thr Asp
385                 390                 395                 400

Asp Thr Ala Val Ala Leu Ile Ala Leu Ala Pro Leu Arg His Asp Pro
                405                 410                 415

Lys Trp Lys Ala Lys Gly Ile Asp Glu Ala Ile Gln Leu Gly Val Asp
            420                 425                 430

Trp Leu Ile Gly Met Gln Ser Gln Gly Gly Gly Trp Gly Ala Phe Asp
        435                 440                 445

Lys Asp Asn Asn Gln Lys Ile Leu Thr Lys Ile Pro Phe Cys Asp Tyr
    450                 455                 460

Gly Glu Ala Leu Asp Pro Pro Ser Val Asp Val Thr Ala His Ile Ile
465                 470                 475                 480

Glu Ala Phe Gly Lys Leu Gly Ile Ser Arg Asn His Pro Ser Met Val
                485                 490                 495

Gln Ala Leu Asp Tyr Ile Arg Arg Glu Gln Glu Pro Ser Gly Pro Trp
            500                 505                 510

Phe Gly Arg Trp Gly Val Asn Tyr Val Tyr Gly Thr Gly Ala Val Leu
        515                 520                 525

Pro Ala Leu Ala Ala Ile Gly Glu Asp Met Thr Gln Pro Tyr Ile Gly
    530                 535                 540

Arg Ala Cys Asp Trp Leu Val Ala His Gln Gln Ala Asp Gly Gly Trp
545                 550                 555                 560

Gly Glu Ser Cys Ala Ser Tyr Met Asp Val Ser Ala Val Gly Arg Gly
                565                 570                 575

Thr Thr Thr Ala Ser Gln Thr Ala Trp Ala Leu Met Ala Leu Leu Ala
            580                 585                 590

Ala Asn Arg Pro Gln Asp Lys Asp Ala Ile Glu Arg Gly Cys Met Trp
        595                 600                 605

Leu Val Glu Arg Gln Ser Ala Gly Thr Trp Asp Glu Pro Glu Phe Thr
    610                 615                 620

Gly Thr Gly Phe Pro Gly Tyr Gly Val Gly Gln Thr Ile Lys Leu Asn
625                 630                 635                 640

Asp Pro Ala Leu Ser Gln Arg Leu Met Gln Gly Pro Glu Leu Ser Arg
                645                 650                 655

Ala Phe Met Leu Arg Tyr Gly Met Tyr Arg His Tyr Phe Pro Leu Met
            660                 665                 670

Ala Leu Gly Arg Ala Leu Arg Pro Gln Ser His Ser
        675                 680


<210> SEQ ID NO 14
<211> LENGTH: 685
<212> TYPE: PRT
<213> ORGANISM: Gluconobacter morbifer

<400> SEQUENCE: 14

Met Ser Pro Ala Asp Ile Ser Thr Lys Ser Ser Ser Phe Gln Arg Leu
1               5                   10                  15

Asp Asn Met Leu Pro Glu Ala Val Ser Ser Ala Cys Asp Trp Leu Ile
```

```
            20                  25                  30

Asp Gln Gln Lys Pro Asp Gly His Trp Val Gly Pro Val Glu Ser Asn
        35                  40                  45

Ala Cys Met Glu Ala Gln Trp Cys Leu Ala Leu Trp Phe Leu Gly Gln
    50                  55                  60

Glu Asp His Pro Leu Arg Pro Arg Leu Ala Gln Ala Leu Leu Glu Met
65                  70                  75                  80

Gln Arg Glu Asp Gly Ser Trp Gly Ile Tyr Val Gly Ala Asp His Gly
                85                  90                  95

Asp Ile Asn Thr Thr Val Glu Ala Tyr Ala Ala Leu Arg Ser Met Gly
            100                 105                 110

Tyr Ala Ala Asp Met Pro Ile Met Ala Lys Ser Ala Ala Trp Ile Gln
        115                 120                 125

Gln Lys Gly Gly Leu Arg Asn Val Arg Val Phe Thr Arg Tyr Trp Leu
    130                 135                 140

Ala Leu Ile Gly Glu Trp Pro Trp Asp Lys Thr Pro Asn Leu Pro Pro
145                 150                 155                 160

Glu Ile Ile Trp Leu Pro Asp Asn Phe Ile Phe Ser Ile Tyr Asn Phe
                165                 170                 175

Ala Gln Trp Ala Arg Ala Thr Met Met Pro Leu Thr Ile Leu Ser Ala
            180                 185                 190

Arg Arg Pro Ser Arg Pro Leu Leu Pro Glu Asn Arg Leu Asp Gly Leu
        195                 200                 205

Phe Pro Glu Gly Arg Glu Asn Phe Asp Tyr Glu Leu Pro Val Lys Gly
    210                 215                 220

Glu Glu Asp Leu Trp Gly Arg Phe Phe Arg Ala Ala Asp Lys Gly Leu
225                 230                 235                 240

His Ser Leu Gln Ser Phe Pro Val Arg Arg Phe Val Pro Arg Glu Ala
                245                 250                 255

Ala Ile Arg His Val Ile Glu Trp Ile Ile Arg His Gln Asp Ala Asp
            260                 265                 270

Gly Gly Trp Gly Gly Ile Gln Pro Pro Trp Ile Tyr Gly Leu Met Ala
        275                 280                 285

Leu Ser Val Glu Gly Tyr Pro Leu His His Pro Val Leu Ala Lys Ala
    290                 295                 300

Met Asp Ala Leu Asn Asp Pro Gly Trp Arg Arg Asp Lys Gly Asp Ala
305                 310                 315                 320

Ser Trp Ile Gln Ala Thr Asn Ser Pro Val Trp Asp Thr Met Leu Ala
                325                 330                 335

Val Leu Ala Leu His Asp Ala Gly Ala Glu Asp Arg Tyr Ser Pro Gln
            340                 345                 350

Met Asp Lys Ala Ile Gly Trp Leu Leu Asp Arg Gln Val Arg Val Lys
        355                 360                 365

Gly Asp Trp Ser Ile Lys Leu Pro Asp Thr Glu Pro Gly Gly Trp Ala
    370                 375                 380

Phe Glu Tyr Ala Asn Asp Lys Tyr Pro Asp Thr Asp Asp Thr Ala Val
385                 390                 395                 400

Ala Leu Ile Ala Leu Ala Gly Cys Arg His Arg Pro Glu Trp Arg Glu
                405                 410                 415

Arg Asp Ile Glu Gly Ala Ile Ser Arg Gly Val Asn Trp Leu Leu Ala
            420                 425                 430

Met Gln Ser Ser Ser Gly Gly Trp Gly Ala Phe Asp Lys Asp Asn Asn
        435                 440                 445
```

```
Arg Ser Ile Leu Thr Lys Ile Pro Phe Cys Asp Phe Gly Glu Ala Leu
    450                 455                 460

Asp Pro Pro Ser Val Asp Val Thr Ala His Val Leu Glu Ala Phe Gly
465                 470                 475                 480

Leu Leu Gly Ile Ser Arg Asn His Pro Ser Val Gln Lys Ala Leu Ala
                485                 490                 495

Tyr Ile Arg Ser Glu Gln Glu Arg Asn Gly Ala Trp Phe Gly Arg Trp
            500                 505                 510

Gly Val Asn Tyr Val Tyr Gly Thr Gly Ala Val Leu Pro Ala Leu Ala
        515                 520                 525

Ala Ile Gly Glu Asp Met Thr Gln Pro Tyr Ile Val Arg Ala Cys Asp
    530                 535                 540

Trp Leu Met Ser Val Gln Gln Glu Asn Gly Gly Trp Gly Glu Ser Cys
545                 550                 555                 560

Ala Ser Tyr Met Asp Ile Asn Ala Val Gly His Gly Val Ala Thr Ala
                565                 570                 575

Ser Gln Thr Ala Trp Ala Leu Ile Gly Leu Leu Ala Ala Lys Arg Pro
            580                 585                 590

Lys Asp Arg Glu Ala Ile Ala Arg Gly Cys Gln Phe Leu Ile Glu Arg
        595                 600                 605

Gln Glu Asp Gly Ser Trp Thr Glu Glu Glu Tyr Thr Gly Thr Gly Phe
    610                 615                 620

Pro Gly Tyr Gly Val Gly Gln Ala Ile Lys Leu Asp Asp Pro Ser Leu
625                 630                 635                 640

Pro Asp Arg Leu Leu Gln Gly Ala Glu Leu Ser Arg Ala Phe Met Leu
                645                 650                 655

Arg Tyr Asp Leu Tyr Arg Gln Tyr Phe Pro Val Met Ala Leu Ser Arg
            660                 665                 670

Ala Arg Arg Met Met Lys Glu Asp Ala Ser Ala Ala Ala
        675                 680                 685
```

<210> SEQ ID NO 15
<211> LENGTH: 1896
<212> TYPE: DNA
<213> ORGANISM: Alicyclobacillus acidocaldarius

<400> SEQUENCE: 15

```
atggctgagc agttggtgga agcgccggcc tacgcgcgga cgctggatcg cgcggtggag      60

tatctcctct cctgccaaaa ggacgaaggc tactggtggg ggccgcttct gagcaacgtc     120

acgatggaag cggagtacgt cctcttgtgc cacattctcg atcgcgtcga tcgggatcgc     180

atggagaaga tccggcggta cctgttgcac gagcagcgcg aggacggcac gtgggccctg     240

tacccgggtg ggccgccgga cctcgacacg accatcgagg cgtacgtcgc gctcaagtat     300

atcggcatgt cgcgcgacga ggagccgatg cagaaggcgc tccggttcat tcagagccag     360

ggcgggatcg agtcgtcgcg cgtgttcacg cggatgtggc tggcgctggt gggagaatat     420

ccgtgggaga aggtgcccat ggtcccgccg gagatcatgt tcctcggcaa gcgcatgccg     480

ctcaacatct acgagtttgg ctcgtgggct cgggcgaccg tcgtggcgct ctcgattgtg     540

atgagccgcc agccggtgtt cccgctgccc gagcgggcgc gcgtgcccga gctgtacgag     600

accgacgtgc ctccgcgccg gcgcggtgcc aagggagggg gtgggtggat cttcgacgcg     660

ctcgaccggg cgctgcacgg gtatcagaag ctgtcggtgc acccgttccg ccgcgcggcc     720

gagatccgcg ccttggactg gttgctcgag cgccaggccg gagacggcag ctggggcggg     780
```

attcagccgc cttggtttta cgcgctcatc gcgctcaaga ttctcgacat gacgcagcat 840
ccggcgttca tcaagggctg ggaaggtcta gagctgtacg gcgtggagct ggattacgga 900
ggatggatgt ttcaggcttc catctcgccg gtgtgggaca cgggcctcgc cgtgctcgcg 960
ctgcgcgctg cggggcttcc ggccgatcac gaccgcttgg tcaaggcggg cgagtggctg 1020
ttggaccggc agatcacggt tccgggcgac tgggcggtga agcgcccgaa cctcaagccg 1080
ggcgggttcg cgttccagtt cgacaacgtg tactacccgg acgtggacga cacggccgtc 1140
gtggtgtggg cgctcaacac cctgcgcttg ccggacgagc gccgcaggcg ggacgccatg 1200
acgaagggat tccgctggat tgtcggcatg cagagctcga acggcggttg gggcgcctac 1260
gacgtcgaca acacgagcga tctcccgaac cacatcccgt tctgcgactt cggcgaagtg 1320
accgatccgc cgtcagagga cgtcaccgcc cacgtgctcg agtgtttcgg cagcttcggg 1380
tacgatgacg cctggaaggt catccggcgc gcggtggaat atctcaagcg ggagcagaag 1440
ccggacggca gctggttcgg tcgttggggc gtcaattacc tctacggcac gggcgcggtg 1500
gtgtcggcgc tgaaggcggt cgggatcgac acgcgcgagc cgtacattca aaaggcgctc 1560
gactgggtcg agcagcatca gaacccggac ggcggctggg gcgaggactg ccgctcgtac 1620
gaggatccgg cgtacgcggg taagggcgcg agcaccccgt cgcagacggc ctgggcgctg 1680
atggcgctca tcgcgggcgg cagggcggag tccgaggccg cgcgccgcgg cgtgcaatac 1740
ctcgtggaga cgcagcgccc ggacggcggc tgggatgagc cgtactacac cggcacgggc 1800
ttcccagggg atttctacct cggctacacc atgtaccgcc acgtgtttcc gacgctcgcg 1860
ctcggccgct acaagcaagc catcgagcgc aggtga 1896

<210> SEQ ID NO 16
<211> LENGTH: 1896
<212> TYPE: DNA
<213> ORGANISM: Artificial Sequence
<220> FEATURE:
<223> OTHER INFORMATION: 215G2 SHC enzyme variant

<400> SEQUENCE: 16
atggctgagc agttggtgga agctccggcc tacgcgcgga cgctggatcg cgcggtggag 60
tatctcctct cctgccaaaa ggacgaaggc tactggtggg ggccgcttct gagcaacgtc 120
acgatggaag cggagtacgt cctcttgtgc cacattctcg atcgcgtcga tcgggatcgc 180
atggagaaga tccggcggta cctgttgcac gagcagcgcg aggacggcac gtgggccctg 240
tacccgggtg ggccgccgga cctcgacacg accatcgagg cgtacgtcgc gctcaagtat 300
atcggcatgt cgcgcgacga ggagccgatg cagaaggcgc tccggttcat tcagagccag 360
ggcgggatcg agtcgtcgcg cgtgttcacg cggaggtggc tggcgctggt gggagaatat 420
ccgtgggaga aggtgcccat ggtcccgccg gagatcatgt tcctcggcaa gcgcatgccg 480
ctcaacatct acgagtttgg ctcgtgggct cgggcgaccg tcgtggcgct ctcgattgtg 540
atgagccgcc agccggtgtt cccgctgccc gagcgggcgc gcgtgcccga gctgtacgag 600
accgacgtgc ctccgcgccg gcgcggtgcc aagggagggg gtgggtggat cttcgacgcg 660
ctcgaccggg tgctgcacgg gtatcagaag ctgtcggtgc acccgttccg ccgcgcggcc 720
gagatccgcg ccttggactg gttgctcgag cgccaggccg gagacggcag ctggggcggg 780
attcagccgc cttggtttta cgcgctcatc gcgctcaaga ttctcgacat gacgcagcat 840
ccggcgttca tcaagggctg ggaaggtcta gagctgtacg gcgtggagct ggattacgga 900

-continued

```
ggatggatgt ttcaggcttc catctcgccg gtgtgggaca cgggcctcgc cgtgctcgcg    960

ctgcgcgctg cggggcttcc ggccgatcac gaccgcttgg tcaaggcggg cgagtggctg   1020

ttggaccggc agatcacggt tccgggcgac tgggcggtga agcgcccgaa cctcaagccg   1080

ggcgggttcg cgttccagtt cgacaacgtg tactacccgg acgtggacga cacggccgtc   1140

gtggtgtggg cgctcaacac cctgcgcttg ccggacgagc gccgcaggcg ggacgccatg   1200

acgaagggat tccgctggat tgtcggcatg cagagctcga acggcggttg ggcgcctac    1260

gacgtcgaca acacgagcga tctcccgaac cacaccccgt tctgcgactt cggcgaagtg   1320

accgatccgc cgtcagagga cgtcaccgcc cacgtgctcg agtgtttcgg cagcttcggg   1380

tacgatgacg cctggaaggt catccggcgc gcggtggaat atctcaagcg ggagcagaag   1440

ccggacggca gctggttcgg tcgttggggc gtcaattacc tctacggcac gggcgcggtg   1500

gtgtcggcgc tgaaggcggt cgggatcgac acgcgcgagc cgtacattca aaaggcgctc   1560

gactgggtcg agcagcatca gaacccggac ggcggctggg gcgaggactg ccgctcgtac   1620

gaggatccgg cgtacgcggg taagggcgcg agcaccccgt cgcagacggc ctgggcgctg   1680

atggcgctca tcgcgggcgg cagggcggag tccgaggccg cgcgccgcgg cgtgcaatac   1740

ctcgtggaga cgcagcgccc ggacggcggc tgggatgagc cgtactacac cggcacgggc   1800

ttcccagggg atttctacct cggctacacc atgtaccgcc acgtgtttcc gacgctcgcg   1860

ctcggccgct acaagcaagc catcgagcgc aggtga                              1896
```

<210> SEQ ID NO 17
<211> LENGTH: 631
<212> TYPE: PRT
<213> ORGANISM: Artificial Sequence
<220> FEATURE:
<223> OTHER INFORMATION: SHC enzyme variant #90C7

<400> SEQUENCE: 17

```
Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
            20                  25                  30

Trp Gly Pro Leu Leu Ser Asn Val Thr Met Glu Ala Glu Tyr Val Leu
        35                  40                  45

Leu Cys His Ile Leu Asp Arg Val Asp Arg Asp Arg Met Glu Lys Ile
    50                  55                  60

Arg Arg Tyr Leu Leu His Glu Gln Arg Glu Asp Gly Thr Trp Ala Leu
65                  70                  75                  80

Tyr Pro Gly Gly Pro Pro Asp Leu Asp Ala Thr Ile Glu Ala Tyr Val
                85                  90                  95

Ala Leu Lys Tyr Ile Gly Met Ser Arg Asp Glu Glu Pro Met Gln Lys
            100                 105                 110

Ala Leu Arg Phe Ile Gln Ser Gln Gly Gly Ile Glu Ser Ser Arg Val
        115                 120                 125

Phe Thr Arg Arg Trp Leu Ala Leu Val Gly Glu Tyr Pro Trp Glu Lys
    130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
                165                 170                 175

Leu Ser Ile Val Met Ser Arg Gln Pro Val Phe Pro Leu Pro Glu Arg
            180                 185                 190
```

-continued

```
Ala Arg Val Pro Glu Leu Tyr Glu Thr Asp Val Pro Pro Arg Arg Arg
        195                 200                 205

Gly Ala Lys Gly Gly Gly Gly Trp Ile Phe Asp Ala Leu Asp Arg Val
    210                 215                 220

Leu His Gly Tyr Gln Lys Leu Ser Val His Pro Phe Arg Arg Ala Ala
225                 230                 235                 240

Glu Ile Arg Ala Leu Asp Trp Leu Leu Glu Arg Gln Ala Gly Asp Gly
                245                 250                 255

Ser Trp Gly Gly Ile Gln Pro Pro Trp Phe Tyr Ala Leu Ile Ala Leu
            260                 265                 270

Lys Ile Leu Asp Met Thr Gln His Pro Ala Phe Ile Lys Gly Trp Glu
        275                 280                 285

Gly Leu Glu Leu Tyr Gly Val Glu Leu Asp Tyr Gly Gly Trp Met Phe
    290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
        355                 360                 365

Asn Val Tyr Tyr Pro Asp Val Asp Asp Thr Ala Val Val Val Trp Ala
    370                 375                 380

Leu Asn Thr Leu Arg Leu Pro Asp Glu Arg Arg Arg Arg Asp Ala Met
385                 390                 395                 400

Thr Lys Gly Phe Arg Trp Ile Val Gly Met Gln Ser Ser Asn Gly Gly
                405                 410                 415

Trp Gly Ala Tyr Asp Val Asp Asn Thr Ser Asp Leu Pro Asn His Thr
            420                 425                 430

Pro Phe Cys Asp Phe Gly Glu Val Thr Asp Pro Pro Ser Glu Asp Val
        435                 440                 445

Thr Ala His Val Leu Glu Cys Phe Gly Ser Phe Gly Tyr Asp Asp Ala
    450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                485                 490                 495

Thr Gly Ala Val Val Ser Ala Leu Lys Ala Val Gly Ile Asp Thr Arg
            500                 505                 510

Glu Pro Tyr Ile Gln Lys Ala Leu Asp Trp Val Glu Gln His Gln Asn
        515                 520                 525

Pro Asp Gly Gly Trp Gly Glu Asp Cys Arg Ser Tyr Glu Asp Pro Ala
    530                 535                 540

Tyr Ala Gly Lys Gly Ala Ser Thr Pro Ser Gln Thr Ala Trp Ala Leu
545                 550                 555                 560

Met Ala Leu Ile Ala Gly Gly Arg Ala Glu Ser Glu Ala Ala Arg Arg
                565                 570                 575

Gly Val Gln Tyr Leu Val Glu Thr Gln Arg Pro Asp Gly Gly Trp Asp
            580                 585                 590

Glu Pro Tyr Tyr Thr Gly Thr Gly Phe Pro Gly Asp Phe Tyr Leu Gly
        595                 600                 605
```

```
Tyr Thr Met Tyr Ser His Val Phe Pro Thr Leu Ala Leu Gly Arg Tyr
    610                 615                 620

Lys Gln Ala Ile Glu Arg Arg
625                 630


<210> SEQ ID NO 18
<211> LENGTH: 631
<212> TYPE: PRT
<213> ORGANISM: Artificial Sequence
<220> FEATURE:
<223> OTHER INFORMATION: SHC enzyme variant #115A7

<400> SEQUENCE: 18

Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
            20                  25                  30

Trp Gly Pro Leu Leu Ser Asn Val Thr Met Glu Ala Glu Tyr Val Leu
        35                  40                  45

Leu Cys His Ile Leu Asp Arg Val Asp Arg Asp Arg Met Glu Lys Ile
    50                  55                  60

Arg Arg Tyr Leu Leu His Glu Gln Arg Glu Asp Gly Thr Trp Ala Leu
65                  70                  75                  80

Tyr Pro Gly Gly Pro Pro Asp Leu Asp Thr Thr Ile Glu Ala Tyr Val
                85                  90                  95

Ala Leu Lys Tyr Ile Gly Met Ser Arg Asp Glu Glu Pro Met Gln Lys
            100                 105                 110

Ala Leu Arg Phe Ile Gln Ser Gln Gly Gly Ile Glu Ser Ser Arg Val
        115                 120                 125

Phe Thr Arg Arg Trp Leu Ala Leu Val Gly Glu Tyr Pro Trp Glu Lys
    130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Thr Thr Val Val Ala
                165                 170                 175

Leu Ser Ile Val Met Ser Arg Gln Pro Val Phe Pro Leu Pro Glu Arg
            180                 185                 190

Ala Arg Val Pro Glu Leu Tyr Glu Thr Asp Val Pro Pro Arg Arg Arg
        195                 200                 205

Gly Ala Lys Gly Gly Gly Gly Trp Ile Phe Asp Ala Leu Asp Arg Val
    210                 215                 220

Leu His Gly Tyr Gln Lys Leu Ser Val His Pro Phe Arg Arg Ala Ala
225                 230                 235                 240

Glu Ile Arg Ala Leu Asp Trp Leu Leu Glu Arg Gln Ala Gly Asp Gly
                245                 250                 255

Ser Trp Gly Gly Ile Gln Pro Pro Trp Phe Tyr Ala Leu Ile Ala Leu
            260                 265                 270

Lys Ile Leu Asp Lys Thr Gln His Pro Ala Phe Ile Lys Gly Trp Glu
        275                 280                 285

Gly Leu Glu Leu Tyr Gly Val Glu Leu Asp Tyr Gly Gly Trp Met Phe
    290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335
```

-continued

Gly Glu Trp Leu Leu Asp Arg Gln Ile Thr Val Pro Gly Asp Trp Ala
340 345 350

Val Lys Arg Pro Asn Leu Lys Pro Gly Gly Phe Ala Phe Gln Phe Asp
355 360 365

Asn Val Tyr Tyr Pro Asp Val Asp Asp Thr Ala Val Val Val Trp Ala
370 375 380

Leu Asn Thr Leu Arg Leu Pro Asp Glu Arg Arg Arg Arg Asp Ala Met
385 390 395 400

Thr Lys Gly Phe Arg Trp Ile Val Gly Met Gln Ser Ser Asn Gly Gly
405 410 415

Trp Gly Ala Tyr Asp Val Asp Asn Thr Ser Asp Leu Pro Asn His Thr
420 425 430

Pro Phe Cys Asp Phe Gly Glu Val Thr Asp Pro Pro Ser Glu Asp Val
435 440 445

Thr Ala His Val Leu Glu Cys Phe Gly Ser Phe Gly Tyr Asp Asp Ala
450 455 460

Trp Lys Val Ile Arg Arg Ala Val Glu Tyr Leu Lys Arg Glu Gln Lys
465 470 475 480

Pro Asp Gly Ser Trp Phe Gly Arg Trp Gly Val Asn Tyr Leu Tyr Gly
485 490 495

Thr Gly Ala Val Val Ser Ala Leu Lys Ala Val Gly Ile Asp Thr Arg
500 505 510

Glu Pro Tyr Ile Gln Lys Ala Leu Asp Trp Val Glu Gln His Gln Asn
515 520 525

Pro Asp Gly Gly Trp Gly Glu Asp Cys Arg Ser Tyr Glu Asp Pro Ala
530 535 540

Tyr Ala Gly Lys Gly Ala Ser Thr Pro Ser Gln Thr Ala Trp Ala Leu
545 550 555 560

Met Ala Leu Ile Ala Gly Gly Arg Ala Glu Ser Glu Ala Ala Arg Arg
565 570 575

Gly Val Gln Tyr Leu Val Glu Thr Gln Arg Pro Asp Gly Gly Trp Asp
580 585 590

Glu Pro Tyr Tyr Thr Gly Thr Gly Phe Pro Gly Asp Phe Tyr Leu Gly
595 600 605

Tyr Thr Met Tyr Arg His Val Phe Pro Thr Leu Ala Leu Gly Arg Tyr
610 615 620

Lys Gln Ala Ile Glu Arg Arg
625 630

<210> SEQ ID NO 19
<211> LENGTH: 642
<212> TYPE: PRT
<213> ORGANISM: Thermosynechococcus elongatus

<400> SEQUENCE: 19

Met Pro Thr Ser Leu Ala Thr Ala Ile Asp Pro Lys Gln Leu Gln Gln
1 5 10 15

Ala Ile Arg Ala Ser Gln Asp Phe Leu Phe Ser Gln Gln Tyr Ala Glu
20 25 30

Gly Tyr Trp Trp Ala Glu Leu Glu Ser Asn Val Thr Met Thr Ala Glu
35 40 45

Val Ile Leu Leu His Lys Ile Trp Gly Thr Glu Gln Arg Leu Pro Leu
50 55 60

Ala Lys Ala Glu Gln Tyr Leu Arg Asn His Gln Arg Asp His Gly Gly
65 70 75 80

-continued

```
Trp Glu Leu Phe Tyr Gly Asp Gly Gly Asp Leu Ser Thr Ser Val Glu
                85                  90                  95

Ala Tyr Met Gly Leu Arg Leu Leu Gly Val Pro Glu Thr Asp Pro Ala
            100                 105                 110

Leu Val Lys Ala Arg Gln Phe Ile Leu Ala Arg Gly Gly Ile Ser Lys
        115                 120                 125

Thr Arg Ile Phe Thr Lys Leu His Leu Ala Leu Ile Gly Cys Tyr Asp
    130                 135                 140

Trp Arg Gly Ile Pro Ser Leu Pro Pro Trp Ile Met Leu Leu Pro Glu
145                 150                 155                 160

Gly Ser Pro Phe Thr Ile Tyr Glu Met Ser Ser Trp Ala Arg Ser Ser
                165                 170                 175

Thr Val Pro Leu Leu Ile Val Met Asp Arg Lys Pro Val Tyr Gly Met
            180                 185                 190

Asp Pro Pro Ile Thr Leu Asp Glu Leu Tyr Ser Glu Gly Arg Ala Asn
        195                 200                 205

Val Val Trp Glu Leu Pro Arg Gln Gly Asp Trp Arg Asp Val Phe Ile
    210                 215                 220

Gly Leu Asp Arg Val Phe Lys Leu Phe Glu Thr Leu Asn Ile His Pro
225                 230                 235                 240

Leu Arg Glu Gln Gly Leu Lys Ala Ala Glu Glu Trp Val Leu Glu Arg
                245                 250                 255

Gln Glu Ala Ser Gly Asp Trp Gly Gly Ile Ile Pro Ala Met Leu Asn
            260                 265                 270

Ser Leu Leu Ala Leu Arg Ala Leu Asp Tyr Ala Val Asp Asp Pro Ile
        275                 280                 285

Val Gln Arg Gly Met Ala Ala Val Asp Arg Phe Ala Ile Glu Thr Glu
    290                 295                 300

Thr Glu Tyr Arg Val Gln Pro Cys Val Ser Pro Val Trp Asp Thr Ala
305                 310                 315                 320

Leu Val Met Arg Ala Met Val Asp Ser Gly Val Ala Pro Asp His Pro
                325                 330                 335

Ala Leu Val Lys Ala Gly Glu Trp Leu Leu Ser Lys Gln Ile Leu Asp
            340                 345                 350

Tyr Gly Asp Trp His Ile Lys Asn Lys Lys Gly Arg Pro Gly Gly Trp
        355                 360                 365

Ala Phe Glu Phe Glu Asn Arg Phe Tyr Pro Asp Val Asp Asp Thr Ala
    370                 375                 380

Val Val Val Met Ala Leu His Ala Val Thr Leu Pro Asn Glu Asn Leu
385                 390                 395                 400

Lys Arg Arg Ala Ile Glu Arg Ala Val Ala Trp Ile Ala Ser Met Gln
                405                 410                 415

Cys Arg Pro Gly Gly Trp Ala Ala Phe Asp Val Asp Asn Asp Gln Asp
            420                 425                 430

Trp Leu Asn Gly Ile Pro Tyr Gly Asp Leu Lys Ala Met Ile Asp Pro
        435                 440                 445

Asn Thr Ala Asp Val Thr Ala Arg Val Leu Glu Met Val Gly Arg Cys
    450                 455                 460

Gln Leu Ala Phe Asp Arg Val Ala Leu Asp Arg Ala Leu Ala Tyr Leu
465                 470                 475                 480

Arg Asn Glu Gln Glu Pro Glu Gly Cys Trp Phe Gly Arg Trp Gly Val
                485                 490                 495
```

```
Asn Tyr Leu Tyr Gly Thr Ser Gly Val Leu Thr Ala Leu Ser Leu Val
            500                 505                 510

Ala Pro Arg Tyr Asp Arg Trp Arg Ile Arg Arg Ala Ala Glu Trp Leu
        515                 520                 525

Met Gln Cys Gln Asn Ala Asp Gly Gly Trp Gly Glu Thr Cys Trp Ser
    530                 535                 540

Tyr His Asp Pro Ser Leu Lys Gly Lys Gly Asp Ser Thr Ala Ser Gln
545                 550                 555                 560

Thr Ala Trp Ala Ile Ile Gly Leu Leu Ala Ala Gly Asp Ala Thr Gly
                565                 570                 575

Asp Tyr Ala Thr Glu Ala Ile Glu Arg Gly Ile Ala Tyr Leu Leu Glu
            580                 585                 590

Thr Gln Arg Pro Asp Gly Thr Trp His Glu Asp Tyr Phe Thr Gly Thr
        595                 600                 605

Gly Phe Pro Cys His Phe Tyr Leu Lys Tyr His Tyr Tyr Gln Gln His
    610                 615                 620

Phe Pro Leu Thr Ala Leu Gly Arg Tyr Ala Arg Trp Arg Asn Leu Leu
625                 630                 635                 640

Ala Thr


<210> SEQ ID NO 20
<211> LENGTH: 720
<212> TYPE: PRT
<213> ORGANISM: Acetobacter pasteurianus

<400> SEQUENCE: 20

Met Asn Met Ala Ser Arg Phe Ser Leu Lys Lys Ile Leu Arg Ser Gly
1               5                   10                  15

Ser Asp Thr Gln Gly Thr Asn Val Asn Thr Leu Ile Gln Ser Gly Thr
            20                  25                  30

Ser Asp Ile Val Arg Gln Lys Pro Ala Pro Gln Glu Pro Ala Asp Leu
        35                  40                  45

Ser Ala Leu Lys Ala Met Gly Asn Ser Leu Thr His Thr Leu Ser Ser
    50                  55                  60

Ala Cys Glu Trp Leu Met Lys Gln Gln Lys Pro Asp Gly His Trp Val
65                  70                  75                  80

Gly Ser Val Gly Ser Asn Ala Ser Met Glu Ala Glu Trp Cys Leu Ala
                85                  90                  95

Leu Trp Phe Leu Gly Leu Glu Asp His Pro Leu Arg Pro Arg Leu Gly
            100                 105                 110

Lys Ala Leu Leu Glu Met Gln Arg Pro Asp Gly Ser Trp Gly Thr Tyr
        115                 120                 125

Tyr Gly Ala Gly Ser Gly Asp Ile Asn Ala Thr Val Glu Ser Tyr Ala
    130                 135                 140

Ala Leu Arg Ser Leu Gly Tyr Ala Glu Asp Asp Pro Ala Val Ser Lys
145                 150                 155                 160

Ala Ala Ala Trp Ile Ile Ser Lys Gly Gly Leu Lys Asn Val Arg Val
                165                 170                 175

Phe Thr Arg Tyr Trp Leu Ala Leu Ile Gly Glu Trp Pro Trp Glu Lys
            180                 185                 190

Thr Pro Asn Leu Pro Pro Glu Ile Ile Trp Phe Pro Asp Asn Phe Val
        195                 200                 205

Phe Ser Ile Tyr Asn Phe Ala Gln Trp Ala Arg Ala Thr Met Met Pro
    210                 215                 220
```

-continued

```
Leu Ala Ile Leu Ser Ala Arg Arg Pro Ser Arg Pro Leu Arg Pro Gln
225                 230                 235                 240

Asp Arg Leu Asp Ala Leu Phe Pro Gly Gly Arg Ala Asn Phe Asp Tyr
                245                 250                 255

Glu Leu Pro Thr Lys Glu Gly Arg Asp Val Ile Ala Asp Phe Phe Arg
            260                 265                 270

Leu Ala Asp Lys Gly Leu His Trp Leu Gln Ser Ser Phe Leu Lys Arg
        275                 280                 285

Ala Pro Ser Arg Glu Ala Ala Ile Lys Tyr Val Leu Glu Trp Ile Ile
    290                 295                 300

Trp His Gln Asp Ala Asp Gly Gly Trp Gly Gly Ile Gln Pro Pro Trp
305                 310                 315                 320

Val Tyr Gly Leu Met Ala Leu His Gly Glu Gly Tyr Gln Phe His His
                325                 330                 335

Pro Val Met Ala Lys Ala Leu Asp Ala Leu Asn Asp Pro Gly Trp Arg
            340                 345                 350

His Asp Lys Gly Asp Ala Ser Trp Ile Gln Ala Thr Asn Ser Pro Val
        355                 360                 365

Trp Asp Thr Met Leu Ser Leu Met Ala Leu His Asp Ala Asn Ala Glu
    370                 375                 380

Glu Arg Phe Thr Pro Glu Met Asp Lys Ala Leu Asp Trp Leu Leu Ser
385                 390                 395                 400

Arg Gln Val Arg Val Lys Gly Asp Trp Ser Val Lys Leu Pro Asn Thr
                405                 410                 415

Glu Pro Gly Gly Trp Ala Phe Glu Tyr Ala Asn Asp Arg Tyr Pro Asp
            420                 425                 430

Thr Asp Asp Thr Ala Val Ala Leu Ile Ala Ile Ala Ser Cys Arg Asn
        435                 440                 445

Arg Pro Glu Trp Gln Ala Lys Gly Val Glu Glu Ala Ile Gly Arg Gly
    450                 455                 460

Val Arg Trp Leu Val Ala Met Gln Ser Ser Cys Gly Gly Trp Gly Ala
465                 470                 475                 480

Phe Asp Lys Asp Asn Asn Lys Ser Ile Leu Ala Lys Ile Pro Phe Cys
                485                 490                 495

Asp Phe Gly Glu Ala Leu Asp Pro Pro Ser Val Asp Val Thr Ala His
            500                 505                 510

Val Leu Glu Ala Phe Gly Leu Leu Gly Leu Pro Arg Asp Leu Pro Cys
        515                 520                 525

Ile Gln Arg Gly Leu Ala Tyr Ile Arg Lys Glu Gln Asp Pro Thr Gly
    530                 535                 540

Pro Trp Phe Gly Arg Trp Gly Val Asn Tyr Leu Tyr Gly Thr Gly Ala
545                 550                 555                 560

Val Leu Pro Ala Leu Ala Ala Leu Gly Glu Asp Met Thr Gln Pro Tyr
                565                 570                 575

Ile Ser Lys Ala Cys Asp Trp Leu Ile Asn Cys Gln Gln Glu Asn Gly
            580                 585                 590

Gly Trp Gly Glu Ser Cys Ala Ser Tyr Met Glu Val Ser Ser Ile Gly
        595                 600                 605

His Gly Ala Thr Thr Pro Ser Gln Thr Ala Trp Ala Leu Met Gly Leu
    610                 615                 620

Ile Ala Ala Asn Arg Pro Gln Asp Tyr Glu Ala Ile Ala Lys Gly Cys
625                 630                 635                 640

Arg Tyr Leu Ile Asp Leu Gln Glu Glu Asp Gly Ser Trp Asn Glu Glu
```

```
                645                 650                 655

Glu Phe Thr Gly Thr Gly Phe Pro Gly Tyr Gly Val Gly Gln Thr Ile
            660                 665                 670

Lys Leu Asp Asp Pro Ala Ile Ser Lys Arg Leu Met Gln Gly Ala Glu
        675                 680                 685

Leu Ser Arg Ala Phe Met Leu Arg Tyr Asp Leu Tyr Arg Gln Leu Phe
    690                 695                 700

Pro Ile Ile Ala Leu Ser Arg Ala Ser Arg Leu Ile Lys Leu Gly Asn
705                 710                 715                 720


<210> SEQ ID NO 21
<211> LENGTH: 685
<212> TYPE: PRT
<213> ORGANISM: Artificial Sequence
<220> FEATURE:
<223> OTHER INFORMATION: GmoSHC variant

<400> SEQUENCE: 21

Met Ser Pro Ala Asp Ile Ser Thr Lys Ser Ser Ser Phe Gln Arg Leu
1               5                   10                  15

Asp Asn Met Leu Pro Glu Ala Val Ser Ser Ala Cys Asp Trp Leu Ile
            20                  25                  30

Asp Gln Gln Lys Pro Asp Gly His Trp Val Gly Pro Leu Glu Ser Asn
        35                  40                  45

Ala Cys Met Glu Ala Glu Trp Cys Leu Ala Leu Trp Phe Leu Gly Gln
    50                  55                  60

Glu Asp His Pro Leu Arg Pro Arg Leu Ala Gln Ala Leu Leu Glu Met
65                  70                  75                  80

Gln Arg Glu Asp Gly Ser Trp Gly Ile Tyr Val Gly Ala Asp His Gly
                85                  90                  95

Asp Ile Asn Thr Thr Val Glu Ala Tyr Ala Ala Leu Arg Ser Met Gly
            100                 105                 110

Tyr Ala Ala Asp Met Pro Ile Met Ala Lys Ser Ala Ala Trp Ile Gln
        115                 120                 125

Gln Lys Gly Gly Leu Arg Asn Val Arg Val Phe Thr Arg Tyr Trp Leu
    130                 135                 140

Ala Leu Ile Gly Glu Trp Pro Trp Asp Lys Thr Pro Asn Leu Pro Pro
145                 150                 155                 160

Glu Ile Ile Trp Leu Pro Asp Asn Phe Ile Phe Ser Ile Tyr Asn Phe
                165                 170                 175

Ala Gln Trp Ala Arg Ala Thr Ile Met Pro Leu Thr Ile Leu Ser Ala
            180                 185                 190

Arg Arg Pro Ser Arg Pro Leu Leu Pro Glu Asn Arg Leu Asp Gly Leu
        195                 200                 205

Phe Pro Glu Gly Arg Glu Asn Phe Asp Tyr Glu Leu Pro Val Lys Gly
    210                 215                 220

Glu Glu Asp Leu Trp Gly Arg Phe Phe Arg Ala Ala Asp Lys Gly Leu
225                 230                 235                 240

His Ser Leu Gln Ser Phe Pro Val Arg Arg Phe Val Pro Arg Glu Ala
                245                 250                 255

Ala Ile Arg His Val Ile Glu Trp Ile Ile Arg His Gln Asp Ala Asp
            260                 265                 270

Gly Gly Trp Gly Gly Ile Gln Pro Pro Trp Ile Tyr Gly Leu Met Ala
        275                 280                 285

Leu Ser Val Glu Gly Tyr Pro Leu His His Pro Val Leu Ala Lys Ala
```

```
    290                 295                 300

Met Asp Ala Leu Asn Asp Pro Gly Trp Arg Arg Asp Lys Gly Asp Ala
305                 310                 315                 320

Ser Trp Ile Gln Ala Ser Asn Ser Pro Val Trp Asp Thr Met Leu Ala
                325                 330                 335

Val Leu Ala Leu His Asp Ala Gly Ala Glu Asp Arg Tyr Ser Pro Gln
            340                 345                 350

Met Asp Lys Ala Ile Gly Trp Leu Leu Asp Arg Gln Val Arg Val Lys
        355                 360                 365

Gly Asp Trp Ser Ile Lys Leu Pro Asp Thr Glu Pro Gly Gly Trp Ala
    370                 375                 380

Phe Glu Tyr Ala Asn Asp Lys Tyr Pro Asp Thr Asp Asp Thr Ala Val
385                 390                 395                 400

Ala Leu Ile Ala Leu Ala Gly Cys Arg His Arg Pro Glu Trp Arg Glu
                405                 410                 415

Arg Asp Ile Glu Gly Ala Ile Ser Arg Gly Val Asn Trp Leu Leu Ala
            420                 425                 430

Met Gln Ser Ser Ser Gly Gly Trp Gly Ala Phe Asp Lys Asp Asn Asn
        435                 440                 445

Arg Ser Ile Leu Thr Lys Ile Pro Phe Cys Asp Phe Gly Glu Ala Leu
    450                 455                 460

Asp Pro Pro Ser Val Asp Val Thr Ala His Val Leu Glu Ala Phe Gly
465                 470                 475                 480

Leu Leu Gly Ile Ser Arg Asn His Pro Ser Val Gln Lys Ala Leu Ala
                485                 490                 495

Tyr Ile Arg Ser Glu Gln Glu Arg Asn Gly Ala Trp Phe Gly Arg Trp
            500                 505                 510

Gly Val Asn Tyr Val Tyr Gly Thr Gly Ala Val Leu Pro Ala Leu Ala
        515                 520                 525

Ala Ile Gly Glu Asp Met Thr Gln Pro Tyr Ile Val Arg Ala Cys Asp
    530                 535                 540

Trp Leu Met Ser Val Gln Gln Glu Asn Gly Gly Trp Gly Glu Ser Cys
545                 550                 555                 560

Ala Ser Tyr Met Asp Ile Asn Ala Val Gly His Gly Val Ala Thr Ala
                565                 570                 575

Ser Gln Thr Ala Trp Ala Leu Ile Gly Leu Leu Ala Ala Lys Arg Pro
            580                 585                 590

Lys Asp Arg Glu Ala Ile Ala Arg Gly Cys Gln Phe Leu Ile Glu Arg
        595                 600                 605

Gln Glu Asp Gly Ser Trp Thr Glu Glu Glu Tyr Thr Gly Thr Gly Tyr
    610                 615                 620

Pro Gly Tyr Gly Val Gly Gln Ala Ile Lys Leu Asp Asp Pro Ser Leu
625                 630                 635                 640

Pro Asp Arg Leu Leu Gln Gly Ala Glu Leu Ser Arg Ala Phe Met Leu
                645                 650                 655

Arg Tyr Asp Leu Tyr Arg Gln Tyr Phe Pro Val Met Ala Leu Ser Arg
            660                 665                 670

Ala Arg Arg Met Met Lys Glu Asp Ala Ser Ala Ala Ala
        675                 680                 685
```

<210> SEQ ID NO 22
<211> LENGTH: 1896
<212> TYPE: DNA
<213> ORGANISM: Artificial Sequence
<220> FEATURE:
<223> OTHER INFORMATION: SHC enzyme variant #90C7

<400> SEQUENCE: 22

```
atggctgagc agttggtgga agctccggcc tacgcgcgga cgctggatcg cgcggtggag      60
tatctcctct cctgccaaaa ggacgaaggc tactggtggg ggccgcttct gagcaacgtc     120
acgatggaag cggagtacgt cctcttgtgc cacattctcg atcgcgtcga tcgggatcgc     180
atggagaaga tccggcggta cctgttgcac gagcagcgcg aggacggcac gtgggccctg     240
tacccgggtg ggccgccgga cctcgacgcg accatcgagg cgtacgtcgc gctcaagtat     300
atcggcatgt cgcgcgacga ggagccgatg cagaaggcgc tccggttcat tcagagccag     360
ggcgggatcg agtcgtcgcg cgtgttcacg cggaggtggc tggcgctggt gggagaatat     420
ccgtgggaga aggtgcccat ggtcccgccg gagatcatgt tcctcggcaa gcgcatgccg     480
ctcaacatct acgagtttgg ctcgtgggct cgggcgaccg tcgtggcgct ctcgattgtg     540
atgagccgcc agccggtgtt cccgctgccc gagcgggcgc gcgtgcccga gctgtacgag     600
accgacgtgc ctccgcgccg gcgcggtgcc aagggagggg gtgggtggat cttcgacgcg     660
ctcgaccggg tgctgcacgg gtatcagaag ctgtcggtgc acccgttccg ccgcgcggcc     720
gagatccgcg ccttggactg gttgctcgag cgccaggccg gagacggcag ctggggcggg     780
attcagccgc cttggtttta cgcgctcatc gcgctcaaga ttctcgacat gacgcagcat     840
ccggcgttca tcaagggctg ggaaggtcta gagctgtacg gcgtggagct ggattacgga     900
ggatggatgt ttcaggcttc catctcgccg gtgtgggaca cgggcctcgc cgtgctcgcg     960
ctgcgcgctg cggggcttcc ggccgatcac gaccgcttgg tcaaggcggg cgagtggctg    1020
ttggaccggc agatcacggt tccgggcgac tgggcggtga agcgcccgaa cctcaagccg    1080
ggcgggttcg cgttccagtt cgacaacgtg tactacccgg acgtggacga cacggccgtc    1140
gtggtgtggg cgctcaacac cctgcgcttg ccggacgagc gccgcaggcg ggacgccatg    1200
acgaagggat tccgctggat tgtcggcatg cagagctcga acggcggttg ggcgcctac     1260
gacgtcgaca acacgagcga tctcccgaac cacaccccgt tctgcgactt cggcgaagtg    1320
accgatccgc cgtcagagga cgtcaccgcc cacgtgctcg agtgtttcgg cagcttcggg    1380
tacgatgacg cctggaaggt catccggcgc gcggtggaat atctcaagcg ggagcagaag    1440
ccggacggca gctggttcgg tcgttggggc gtcaattacc tctacggcac gggcgcggtg    1500
gtgtcggcgc tgaaggcggt cgggatcgac acgcgcgagc cgtacattca aaaggcgctc    1560
gactgggtcg agcagcatca gaacccggac ggcggctggg gcgaggactg ccgctcgtac    1620
gaggatccgg cgtacgcggg taagggcgcg agcaccccgt cgcagacggc ctgggcgctg    1680
atggcgctca tcgcgggcgg cagggcggag tccgaggccg cgcgccgcgg cgtgcaatac    1740
ctcgtggaga cgcagcgccc ggacggcggc tgggatgagc cgtactacac cggcacgggc    1800
ttcccagggg atttctacct cggctacacc atgtacagcc acgtgtttcc gacgctcgcg    1860
ctcggccgct acaagcaagc catcgagcgc aggtga                              1896
```

<210> SEQ ID NO 23
<211> LENGTH: 1896
<212> TYPE: DNA
<213> ORGANISM: Artificial Sequence
<220> FEATURE:
<223> OTHER INFORMATION: SHC enzyme variant #115A7

<400> SEQUENCE: 23
atggctgagc agttggtgga agctccggcc tacgcgcgga cgctggatcg cgcggtggag 60
tatctcctct cctgccaaaa ggacgaaggc tactggtggg ggccgcttct gagcaacgtc 120
acgatggaag cggagtacgt cctcttgtgc cacattctcg atcgcgtcga tcgggatcgc 180
atggagaaga tccggcggta cctgttgcac gagcagcgcg aggacggcac gtgggccctg 240
tacccgggtg ggccgccgga cctcgacacg accatcgagg cgtacgtcgc gctcaagtat 300
atcggcatgt cgcgcgacga ggagccgatg cagaaggcgc tccggttcat tcagagccag 360
ggcgggatcg agtcgtcgcg cgtgttcacg cggaggtggc tggcgctggt gggagaatat 420
ccgtgggaga aggtgcccat ggtcccgccg gagatcatgt tcctcggcaa gcgcatgccg 480
ctcaacatct acgagtttgg ctcgtgggct cggacgaccg tcgtggcgct ctcgattgtg 540
atgagccgcc agccggtgtt cccgctgccc gagcgggcgc gcgtgcccga gctgtacgag 600
accgacgtgc ctccgcgccg gcgcggtgcc aagggagggg gtgggtggat cttcgacgcg 660
ctcgaccggg tgctgcacgg gtatcagaag ctgtcggtgc acccgttccg ccgcgcggcc 720
gagatccgcg ccttggactg gttgctcgag cgccaggccg gagacggcag ctggggcggg 780
attcagccgc cttggtttta cgcgctcatc gcgctcaaga ttctcgacaa gacgcagcat 840
ccggcgttca tcaagggctg ggaaggtcta gagctgtacg gcgtggagct ggattacgga 900
ggatggatgt ttcaggcttc catctcgccg gtgtgggaca cgggcctcgc cgtgctcgcg 960
ctgcgcgctg cggggcttcc ggccgatcac gaccgcttgg tcaaggcggg cgagtggctg 1020
ttggaccggc agatcacggt tccgggcgac tgggcggtga agcgcccgaa cctcaagccg 1080
ggcgggttcg cgttccagtt cgacaacgtg tactacccgg acgtggacga cacggccgtc 1140
gtggtgtggg cgctcaacac cctgcgcttg ccggacgagc gccgcaggcg ggacgccatg 1200
acgaagggat tccgctggat tgtcggcatg cagagctcga acggcggttg gggcgcctac 1260
gacgtcgaca acacgagcga tctcccgaac cacacccgt tctgcgactt cggcgaagtg 1320
accgatccgc cgtcagagga cgtcaccgcc cacgtgctcg agtgtttcgg cagcttcggg 1380
tacgatgacg cctggaaggt catccggcgc gcggtggaat atctcaagcg ggagcagaag 1440
ccggacggca gctggttcgg tcgttggggc gtcaattacc tctacggcac gggcgcggtg 1500
gtgtcggcgc tgaaggcggt cgggatcgac acgcgcgagc cgtacattca aaaggcgctc 1560
gactgggtcg agcagcatca gaacccggac ggcggctggg gcgaggactg ccgctcgtac 1620
gaggatccgg cgtacgcggg taagggcgcg agcaccccgt cgcagacggc ctgggcgctg 1680
atggcgctca tcgcgggcgg cagggcggag tccgaggccg cgcgccgcgg cgtgcaatac 1740
ctcgtggaga cgcagcgccc ggacggcggc tgggatgagc cgtactacac cggcacgggc 1800
ttcccagggg atttctacct cggctacacc atgtaccgcc acgtgtttcc gacgctcgcg 1860
ctcggccgct acaagcaagc catcgagcgc aggtga 1896